US012054534B2

(12) United States Patent
Cardoso et al.

(10) Patent No.: US 12,054,534 B2
(45) Date of Patent: Aug. 6, 2024

(54) PROSTATE SPECIFIC MEMBRANE ANTIGEN BINDING FIBRONECTIN TYPE III DOMAINS

(71) Applicant: Janssen Biotech, Inc., Horsham, PA (US)

(72) Inventors: Rosa Cardoso, Spring House, PA (US); Michael Diem, Spring House, PA (US); Shalom Goldberg, Spring House, PA (US); Linus Hyun, Spring House, PA (US); Steven Jacobs, Spring House, PA (US); Donna Klein, Spring House, PA (US); Karyn O'Neil, Spring House, PA (US); Tracy Spinka-Doms, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 802 days.

(21) Appl. No.: 16/949,078

(22) Filed: Oct. 13, 2020

(65) Prior Publication Data

US 2021/0147510 A1 May 20, 2021

Related U.S. Application Data

(63) Continuation of application No. 15/148,312, filed on May 6, 2016, now Pat. No. 10,844,111.

(60) Provisional application No. 62/157,772, filed on May 6, 2015.

(51) Int. Cl.

| | |
|---|---|
| ***G01N 33/574*** | (2006.01) |
| ***A61K 51/08*** | (2006.01) |
| ***C07K 14/78*** | (2006.01) |
| *A61K 38/00* | (2006.01) |

(52) U.S. Cl.

CPC .............. *C07K 14/78* (2013.01); *A61K 51/08* (2013.01); *G01N 33/57434* (2013.01); *A61K 38/00* (2013.01); *G01N 2333/705* (2013.01)

(58) Field of Classification Search

CPC ...... G01N 33/574; G01N 33/53; A61K 38/00; A61K 38/16; A61K 33/574

See application file for complete search history.

(56) References Cited

U.S. PATENT DOCUMENTS

| | | | |
|---|---|---|---|
| 5,223,409 | A | 6/1993 | Ladner |
| 5,635,483 | A | 6/1997 | Pettit |
| 5,780,588 | A | 7/1998 | Pettit |
| 5,856,456 | A | 1/1999 | Whitlow |
| 5,981,209 | A | 11/1999 | Slusher |
| 6,172,197 | B1 | 1/2001 | McCafferty |
| 6,472,147 | B1 | 10/2002 | Janda |
| 6,582,915 | B1 | 6/2003 | Griffiths |
| 6,673,901 | B2 | 1/2004 | Koide |
| 6,969,108 | B2 | 11/2005 | Fukumoto |
| 7,842,476 | B2 | 11/2010 | McGregor |
| 8,278,419 | B2 | 10/2012 | Jacobs |
| 8,569,227 | B2 | 10/2013 | Jacobs |
| 2006/0009525 | A1 | 1/2006 | Tsukamoto |
| 2010/0216708 | A1 | 8/2010 | Jacobs |
| 2011/0118144 | A1 | 5/2011 | Hyun |
| 2011/0274623 | A1 | 11/2011 | Jacobs |
| 2013/0079243 | A1 | 3/2013 | Diem |
| 2013/0226834 | A1 | 8/2013 | Gannalo, II |
| 2014/0199294 | A1 | 7/2014 | Mimoto |

FOREIGN PATENT DOCUMENTS

| | | | |
|---|---|---|---|
| WO | 0232925 | A2 | 4/2002 |
| WO | 2002088172 | A2 | 11/2002 |
| WO | 2008066752 | A2 | 6/2008 |
| WO | 2009085462 | A1 | 7/2009 |
| WO | 2010051274 | A2 | 5/2010 |
| WO | 2011137319 | A2 | 11/2011 |
| WO | 2012162418 | A1 | 11/2012 |
| WO | 2013049275 | A1 | 4/2013 |
| WO | 2014081944 | A2 | 5/2014 |
| WO | 2015089073 | A2 | 6/2015 |

OTHER PUBLICATIONS

Redman et al. (Mol. Immunol. Oct. 2015; 67 (2 Pt A): 28-45).*
Lipovšek et al. (Protein Eng. Des. Sel. Jan. 2011; 24 (1-2): 3-9).*
Nováková et al. (Prostate. May 2017; 77 (7): 749-764; author manuscript; pp. 1-28).*
Jacobs, Steven A. et al. "Design of novel FN3 domains with high stability by a consensus sequence approach," Protein Engineering, Design & Selection, vol. 25, No. 3 (Jan. 12, 2012) pp. 107-117.
William Olson et al, "Antibody-drug conjugates targeting prostate-specific membrane antigen", Frontiers in Bioscience, vol. 19, No. 1, pp. 12-33, (2014).
Jacobs, et al., "FN3 Domain Engineering," Protein Engineering, pp. 145-162 (2012).
Goldberg et al., "Engineering a targeted delivery platform using Centyrins", Protein Engineering, Design & Selection, vol. 29, No. 12, pp. 563-572, 2016.
Alfthan, et al., "Properties of a single-chain antibody containing different linker peptides, "Protein Engineering, 8(7): 725-731 (1995).
Baccala et al., "Expression of Prostate-Specific Membrane Antigen in Tumor-Associated Neovasculature of Renal Neoplasms," Urology, vol. 70, pp. 385-390 (2007).

(Continued)

*Primary Examiner* — Stephen L Rawlings
(74) *Attorney, Agent, or Firm* — Ice Miller LLP

(57) ABSTRACT

PSMA binding FN3 domains, their conjugates, isolated nucleotides encoding the molecules, vectors, host cells, and methods of making thereof are useful in the generation of therapeutic molecules and treatment and diagnosis of diseases and disorders.

14 Claims, 14 Drawing Sheets

Specification includes a Sequence Listing.

(56) References Cited

OTHER PUBLICATIONS

Binz et al., "High-affinity binders selected from designed ankyrin repeat protein libraries," Nature Biotechnology, vol. 22, No. 5, pp. 575-585 (May 2004).
Birtalan et al., "The Intrinsic Contributions of Tyrosine, Serine, Glycine and Arginine to the Affinity and Specificity of Antibodies", Journal of Molecular Biology, vol. 377, Issue 5, pp. 1518-1528, Apr. 2008.
Bork et al., "Proposed acquisition of an animal protein domain by bacteria", Proc. Natl. Acad, Sci, vol. 89, pp. 8990-8994, Oct. 1992.
Bostwick et al., "Prostate Specific Membrane Antigen Expression in Prostatic Intraepithelial Neoplasia and Adenocarcinoma," Cancer, vol. 82, No. 11, pp. 2256-2261 (Jun. 1, 1998).
Boyton et al., "Natural Killer cells, killer immunoglobulin-like receptors and human leucocyte antigen class I in disease," British Society for Immunology, Clinical and Experimental Immunology, vol. 149, pp. 1-8 (2007).
Brinkley et al., "A Brief Survey of Methods for Preparing Protein Conjugates with Dyes, Haptens, and Cross-Linking Reagents," Bioconjugate Chem., vol. 3, No. 1, pp. 2-13 (1992).
Chang et al., "Prostate-specific Membrane Antigen Is Produced in Tumor-associated Neovasculature," Clinical Cancer Research, vol. 5, pp. 2674-2681 (Oct. 1999).
Chen et al., "A general strategy for the evolution of bond-forming enzymes using yeast display," PNAS, vol. 108, No. 28, pp. 11399-11404 (Jul. 12, 2011).
Galsky et al., "Phase I Trial of the Prostate-Specific Membrane Antigen-Directed Immunoconjugate MLN2704 in Patients With Progressive Metastatic Castration-Resistant Prostate Cancer," Journal of Clinical Oncology, vol. 26, No. 13, pp. 2147-2154 (May 1, 2008).
Hallewell et al., "Genetically engineered Polymers of Human CuZn Superoxide Dismutase", Journal of Biological Chemistry, vol. 264, No. 9, pp. 5260-5268, 1989.
Hanes et al., "In vitro selection and evolution of the functional proteins by using ribosome display", Proc Natl. Acad. Sci,. USA, vol. 94, pp. 4937-4942, May 1997.
Kawakami et al., "Enhanced Expression of Prostate-specific Membrane Antigen Gene in pro Cancer as Revealed by in Situ Hybridization," Cancer Research, vol. 57, pp. 2321-2324 (Jun. 15, 1997).
Koide et al., "High-affinity single-domain binding proteins with a binary-code interface," PNAS, vol. 104, No. 16, pp. 6632-6637 (Apr. 17, 2007).
Lehmann et al., "Engineering proteins for theromostability: the use of sequence alignments versus rational design and directed evolution", Current Opinion in Biotechnology, vol. 12, pp. 371-375, 2001.
Liu et al., "Monoclonal Antibodies to the Extracellular Domain of Prostat-specific Membrane Antigen Also React with Tumor Vascular Endothelium 1," Cancer Research, vol. 57, pp. 3629-3634 (Sep. 1, 1997).
Ljunggren et al., "Prospects for the use of NK cells in immunotherapy of human cancer," Immunology, vol. 7, pp. 329-339 (May 2007).
Meinke, et al., "Cellulose-Binding Polypeptides from Cellulomonas fimi: Endoglucanase D (CenD), a Family A β-1,4-Glucanase," Journal of Bacteriology, 175(7): 1910-1918 (1993).
Milowsky et al., "Vascular Targeted Therapy With Anti-Prostate-Specific Membrane Antigen Monoclonal Antibody J591 in Advanced Solid Tumors," Journal of Clinical Oncology, vol. 25, No. 5, pp. 540-547 (Feb. 10, 2007).
Morris et al., "Phase I Evaluation of J591 as a Vascular Targeting Agent in Progressive Solid Tumors," Clinical Cancer Research, vol. 13, No. 9, pp. 2707-2713 (May 1, 2007).
Odegrip et al., "CIS display: In vitro selection of peptides from libraries of protein-DNA complexes", Proc Natl Acad Sci USA, vol. 101, No. 9, pp. 2806-2810, Mar. 2004.
Olson et al., "Design, expression, and stability of a diverse protein library based on the human fibronectin type III domain", Protein Science, vol. 16, No. 3, pp. 476-484, 2007.
Roberts et al., "RNA-peptide fusions for the in vitro selection of peptides and proteins", Proc. Natl. Acad Sci, USA. vol. 94, pp. 12297-12302, Nov. 1997.
Robinson, et al., "Covalent Attachment of Arc Repressor Subunits by a Peptide Linker Enhances Affinity for Operator DNA," Biochemistry, 35: 109-116 (1996).
Silver et al., "Prostate-specific membrane antigen expression in normal and malignant human tissues," Clinical Cancer Research, vol. 3, pp. 81-85 (1997).
Strohl, William R., "Optimization of Fc-mediated effector functions of monoclonal antibodies," Current Opinion in Biotechnology, vol. 20, pp. 685-691 (2009).
Su et al., "Alternatively Spliced Variants fo Prostate-specific Membrane Antigen RNA: Ratio of Expression as a Potential Measurement of Progression 1," Cancer Research, vol. 55, pp. 1441-1443 (Apr. 1, 1995).
Therasse et al., "New Guidelines to Evaluate the Response to Treatment in Solid Tumors," Journal of the National Cancer Institute, vol. 92, No. 3, pp. 205-216 (Feb. 2, 2000).
Ton-That et al., "Purification and characterization of sortase, the transpeptidase that cleaves surface proteins of *Staphylococcus aureus* at the LPXTG motif," PNAS, vol. 96, No. 22, pp. 12424-12429, 1999.
Watanabe, et al., "Gene Cloning of Chitinase A1 from Bacillus circulans WL-12 Revealed Its Evolutionary Relationship to Serratia Chitinase and to the Type III Homology United of Fibronectin," The Journal of Biological Chemistry, 265 (26): 15659-15665, 1990.
Woyke et al., "In Vitro Activities and Postantifungal Effects of the Potent Dolastatin 10 Derivative Auristatin PHE," Antimicrobial Agents and Chemotherapy, vol. 45, No. 12, pp. 3580-3584 (Dec. 2001).
Wright et al., "Upregulation of Prostate-Specific Membrane Antigen after Androgen-Deprivation Therapy," Urology, vol. 48, No. 2, pp. 326-334 (1996).
Natarajan et al., "A Novel Engineered Anti-CD20 Tracer Enables Early Time PET Imaging in a Humanized Transgenic Mouse Model of B-Cell Non-Hodgkins Lymphoma," Clin. Cancer Res. 19(24): 6820-9, (2013).
Diem et al., "Selection of high-affinity Centyrin FN3 domains from a simple library diversified at a combination of strand and loop positions", Protein Engineering, Design and Selection, vol. 27, No. 10, pp. 419-429, (2014).

* cited by examiner

Figure 4A.

h KSSNEATNITPKHNMKAFLDELKAENIKKFLYNFTQIPHLAGTEQNFQLA
c KSSSEATNITPKHNMKAFLDELKAENIKKFLHNFTQIPHLAGTEQNFQLA h KQIQSQWKEFGLDSVELAHYDVLLSYPNKTHPNYISIINEDGNEIFNTSL
c KQIQSQWKEFGLDSVELTHYDVLLSYPNKTHPNYISIINEDGNEIFNTSL h FEPPPPGYENVSDIVPPFSAFSPQGMPEGDLVYVNYARTEDFFKLERDMK
c FEPPPAGYENVSDIVPPFSAFSPQGMPEGDLVYVNYARTEDFFKLERDMK h INCSGKIVIARYGKVFRGNKVKNAQLAGAKGVILYSDPADYFAPGVKSYP
c INCSGKIVIARYGKVFRGNKVKNAQLAGATGVILYSDPDDYFAPGVKSYP h DGWNLPGGGVQRGNILNLNGAGDPLTPGYPANEYAYRRGIAEAVGLPSIP
c DGWNLPGGGVQRGNILNLNGAGDPLTPGYPANEYAYRRGMAEAVGLPSIP h VHPIGYYDAQKLLEKMGGSAPPDSSWRGSLKVPYNVGPGFTGNFSTQKVK
c VHPIGYYDAQKLLEKMGGSASPDSSWRGSLKVPYNVGPGFTGNFSTQKVK h MHIHSTNEVTRIYNVIGTLRGAVEPDRYVILGGHRDSWVFGGIDPQSGAA
c MHIHSTSEVTRIYNVIGTLRGAVEPDRYVILGGHRDSWVFGGIDPQSGAA h VVHEIVRSFGTLKKEGWRPRRTILFASWDAEEFGLLGSTEWAEENSRLLQ
c VVHEIVRSFGMLKKEGWRPRRTILFASWDAEEFGLLGSTEWAEENSRLLQ h ERGVAYINADSSIEGNYTLRVDCTPLMYSLVHNLTKELKSPDEGFEGKSL
c ERGVAYINADSSIEGNYTLRVDCTPLMYSLVYNLTKELESPDEGFEGKSL h YESWTKKSPSPEFSGMPRISKLGSGNDFEVFFQRLGIASGRARYTKNWET
c YESWTKKSPSPEFSGMPRISKLGSGNDFEVFFQRLGIASGRARYTKNWET h NKFSGYPLYHSVYETYELVEKFYDPMFKYHLTVAQVRGGMVFELANSIVL
c NKFSSYPLYHSVYETYELVEKFYDPMFKYHLTVAQVRGGMVFELANSVVL h PFDCRDYAVVLRKYADKIYSISMKHPQEMKTYSVSFDSLFSAVKNFTEIA
c PFDCRDYAVVLRKYADKIYNISMKHPQEMKTYSVSFDSLFSAVKNFTEIA h SKFSERLQDFDKSNPIVLRMMNDQLMFLERAFIDPLGLPDRPFYRHVIYA
c SKFSERLRDFDKSNPILLRMMNDQLMFLERAFIDPLGLPDRPFYRHVIYA h PSSHNKYAGESFPGIYDALFDIESKVDPSKAWGEVKRQIYVAAFTVQAAA
c PSSHNKYAGESFPGIYDALFDIESKVDPSQAWGEVKRQISIATFTVQAAA h ETLSEVA
c ETLSEVA

Figure 4B.

```
1                                                    50
LPAPKNLVVSRVTEDSARLSWTAPDAAFDSFAIGYWEWDDDGEAIVLTVP

51                                    89
GSERSYDLTGLKPGTEYPVYIAGVKGGQWSFPLSAIFTT
```

C. PC3 (PSMA- Cell line)

0% of cells are positive for PSMA

SEQUENCE LISTING

```
<160> NUMBER OF SEQ ID NOS: 160

<210> SEQ ID NO 1
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85


<210> SEQ ID NO 2
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(86)
<223> OTHER INFORMATION: Any amino acid
<220> FEATURE:
<221> NAME/KEY: MISC_FEATURE
<222> LOCATION: (75)..(86)
<223> OTHER INFORMATION: This region may encompass 7-12 residues

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Pro Leu Ser Ala Glu Phe Thr Thr
                85                  90


<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(27)
```

<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (28)..(28)
<223> OTHER INFORMATION: Phe, Ile, Leu, Val or Tyr
<220> FEATURE:
<221> NAME/KEY: MOD_RES
<222> LOCATION: (29)..(29)
<223> OTHER INFORMATION: Asp, Glu or Thr
<220> FEATURE:
<221> NAME/KEY: MOD_RES
<222> LOCATION: (75)..(79)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (81)..(82)
<223> OTHER INFORMATION: Ala, Arg, Asn, Asp, Glu, Gln, Gly, His, Ile,
      Leu, Lys, Phe, Pro, Ser, Thr, Trp, Tyr or Val

<400> SEQUENCE: 3

```
Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Ser
65                  70                  75                  80

Xaa Xaa Leu Ser Ala Glu Phe Thr Thr
                85
```

<210> SEQ ID NO 4
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85
```

<210> SEQ ID NO 5
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

```
<221> NAME/KEY: MOD_RES
<222> LOCATION: (22)..(30)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MISC_FEATURE
<222> LOCATION: (22)..(30)
<223> OTHER INFORMATION: This region may encompass 6-9 residues
<220> FEATURE:
<221> NAME/KEY: MOD_RES
<222> LOCATION: (78)..(87)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MISC_FEATURE
<222> LOCATION: (78)..(87)
<223> OTHER INFORMATION: This region may encompass 7-9 residues

<400> SEQUENCE: 5

Leu Pro Ala Pro Lys Asn Leu Val Val Ser Arg Val Thr Glu Asp Ser
1               5                   10                  15

Ala Arg Leu Ser Trp Xaa Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Xaa Xaa Xaa
65                  70                  75                  80

Xaa Xaa Xaa Xaa Xaa Xaa Xaa Ser Asn Pro Leu Ser Ala Ile Phe Thr
                85                  90                  95

Thr


<210> SEQ ID NO 6
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(86)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (75)..(86)
<223> OTHER INFORMATION: This region may encompass 7-12 residues

<400> SEQUENCE: 6

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95
```

```
<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (34)..(34)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (36)..(36)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (38)..(41)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (68)..(68)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (70)..(70)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (72)..(72)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (78)..(79)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (81)..(81)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85


<210> SEQ ID NO 8
<211> LENGTH: 89
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (34)..(34)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (36)..(36)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (38)..(41)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (46)..(46)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (48)..(48)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (68)..(68)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (70)..(70)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (72)..(72)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (78)..(79)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (81)..(81)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (84)..(84)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (86)..(86)
<223> OTHER INFORMATION: Ala, Asp, Glu, Phe, Gly, His, Ile, Lys, Leu,
      Asn, Pro, Gln, Arg, Ser, Thr, Val, Tyr or Trp

<400> SEQUENCE: 8

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
        35                  40                  45
```

```
Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
                85


<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

gtgacacggc ggttagaac                                                19


<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

gcctttggga agcttctaag                                               20


<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

cggcggttag aacgcggcta caattaatac                                    30


<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

catgattacg ccaagctcag aa                                            22


<210> SEQ ID NO 13
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(224)
<223> OTHER INFORMATION: a, c, t, g, unknown or other

<400> SEQUENCE: 13

gtgacacggc ggttagaacg cggctacaat taatacataa ccccatcccc ctgttgacaa     60

ttaatcatcg gctcgtataa tgtgtggaat tgtgagcgga taacaatttc acacaggaaa    120
```

```
caggatctac catgctgccg gcgccgaaaa acctggttgt ttctgaagtt accgaagact    180

ctctgcgtct gtcttggnnn nnnnnnnnnn nnnnnnnnnn nnnnttygac tctttcctga    240

tccagtacca ggaatctgaa aaagttggtg aagcgatcaa cctgaccgtt ccgggttctg    300

aacgttctta cgacctgacc ggtctgaaac cgggtaccga atacaccgtt tctatctacg    360

gtgttcttag aagcttccca aaggc                                          385
```

<210> SEQ ID NO 14
<211> LENGTH: 382
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (198)..(221)
<223> OTHER INFORMATION: a, c, t, g, unknown or other

<400> SEQUENCE: 14

```
gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctgaagtt accgaagact    180

ctctgcgtct gtcttggnnn nnnnnnnnnn nnnnnnnnnn nttygactct ttcctgatcc    240

agtaccagga atctgaaaaa gttggtgaag cgatcaacct gaccgttccg ggttctgaac    300

gttcttacga cctgaccggt ctgaaaccgg gtaccgaata caccgtttct atctacggtg    360

ttcttagaag cttcccaaag gc                                             382
```

<210> SEQ ID NO 15
<211> LENGTH: 379
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (198)..(218)
<223> OTHER INFORMATION: a, c, t, g, unknown or other

<400> SEQUENCE: 15

```
gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctgaagtt accgaagact    180

ctctgcgtct gtcttggnnn nnnnnnnnnn nnnnnnnntt ygactctttc ctgatccagt    240

accaggaatc tgaaaaagtt ggtgaagcga tcaacctgac cgttccgggt tctgaacgtt    300

cttacgacct gaccggtctg aaaccgggta ccgaatacac cgtttctatc tacggtgttc    360

ttagaagctt cccaaaggc                                                 379
```

<210> SEQ ID NO 16
<211> LENGTH: 376
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (198)..(215)
<223> OTHER INFORMATION: a, c, t, g, unknown or other

<400> SEQUENCE: 16
gtgacacggc ggttagaacg cggctacaat taatacataa ccccatcccc ctgttgacaa 60
ttaatcatcg gctcgtataa tgtgtggaat tgtgagcgga taacaatttc acacaggaaa 120
caggatctac catgctgccg gcgccgaaaa acctggttgt ttctgaagtt accgaagact 180
ctctgcgtct gtcttggnnn nnnnnnnnnn nnnnnttyga ctctttcctg atccagtacc 240
aggaatctga aaaagttggt gaagcgatca acctgaccgt tccgggttct gaacgttctt 300
acgacctgac cggtctgaaa ccgggtaccg aatacaccgt ttctatctac ggtgttctta 360
gaagcttccc aaaggc 376

<210> SEQ ID NO 17
<211> LENGTH: 131
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17
cggcggttag aacgcggcta caattaatac ataaccccat ccccctgttg acaattaatc 60
atcggctcgt ataatgtgtg gaattgtgag cggataacaa tttcacacag gaaacaggat 120
ctaccatgct g 131

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
cggcggttag aacgcggcta caattaatac 30

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
ccaagacaga cgggcagagt cttcggtaac gcgagaaaca accaggtttt tcggcgccgg 60
cagcatggta gatcctgttt c 81

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ccgaagactc tgcccgtctg tcttgg 26

<210> SEQ ID NO 21

<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
cagtggtctc acggattcct ggtactggat caggaaagag tcgaa 45

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
catgcggtct cttccgaaaa agttggtgaa gcgatcgtcc tgaccgttcc gggt 54

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
ggtggtgaag atcgcagaca gcgggttag 29

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
cggcggttag aacgcggcta c 21

<210> SEQ ID NO 25
<211> LENGTH: 61
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
aagatcagtt gcggccgcta gactagaacc gctgccaccg ccggtggtga agatcgcaga 60
c 61

<210> SEQ ID NO 26
<211> LENGTH: 485
<212> TYPE: DNA
<213> ORGANISM: Artificial Sequence
<220> FEATURE:
<223> OTHER INFORMATION: Description of Artificial Sequence: Synthetic
polynucleotide
<220> FEATURE:
<221> NAME/KEY: modified_base
<222> LOCATION: (357)..(392)
<223> OTHER INFORMATION: a, c, t, g, unknown or other

<400> SEQUENCE: 26

```
gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctcgcgtt accgaagact    180

ctgcgcgtct gtcttggacc gcgccggacg cggcgttcga ctctttcctg atccagtacc    240

aggaatctga aaaagttggt gaagcgatcg tgctgaccgt tccgggttct gaacgttctt    300

acgacctgac cggtctgaaa ccgggtaccg aatacaccgt ttctatctac ggtgttnnnn    360

nnnnnnnnnn nnnnnnnnnn nnnnnnnnnn nntctaaccc gctgtctgcg atcttcacca    420

ccggcggtca ccatcaccat caccatggca gcggttctag tctagcggcc gcaactgatc    480

ttggc                                                                485
```

<210> SEQ ID NO 27
<211> LENGTH: 482
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (357)..(389)
<223> OTHER INFORMATION: a, c, t, g, unknown or other

<400> SEQUENCE: 27

```
gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctcgcgtt accgaagact    180

ctgcgcgtct gtcttggacc gcgccggacg cggcgttcga ctctttcctg atccagtacc    240

aggaatctga aaaagttggt gaagcgatcg tgctgaccgt tccgggttct gaacgttctt    300

acgacctgac cggtctgaaa ccgggtaccg aatacaccgt ttctatctac ggtgttnnnn    360

nnnnnnnnnn nnnnnnnnnn nnnnnnnnnt ctaacccgct gtctgcgatc ttcaccaccg    420

gcggtcacca tcaccatcac catggcagcg gttctagtct agcggccgca actgatcttg    480

gc                                                                   482
```

<210> SEQ ID NO 28
<211> LENGTH: 479
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (357)..(386)
<223> OTHER INFORMATION: a, c, t, g, unknown or other

<400> SEQUENCE: 28

```
gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctcgcgtt accgaagact    180

ctgcgcgtct gtcttggacc gcgccggacg cggcgttcga ctctttcctg atccagtacc    240

aggaatctga aaaagttggt gaagcgatcg tgctgaccgt tccgggttct gaacgttctt    300

acgacctgac cggtctgaaa ccgggtaccg aatacaccgt ttctatctac ggtgttnnnn    360
```

```
nnnnnnnnnn nnnnnnnnnn nnnnnntcta acccgctgtc tgcgatcttc accaccggcg    420

gtcaccatca ccatcaccat ggcagcggtt ctagtctagc ggccgcaact gatcttggc     479


<210> SEQ ID NO 29
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(383)
<223> OTHER INFORMATION: a, c, t, g, unknown or other

<400> SEQUENCE: 29

gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctcgcgtt accgaagact    180

ctgcgcgtct gtcttggacc gcgccggacg cggcgttcga ctctttcctg atccagtacc    240

aggaatctga aaaagttggt gaagcgatcg tgctgaccgt tccgggttct gaacgttctt    300

acgacctgac cggtctgaaa ccgggtaccg aatacaccgt ttctatctac ggtgttnnnn    360

nnnnnnnnnn nnnnnnnnnn nnntctaacc cgctgtctgc gatcttcacc accggcggtc    420

accatcacca tcaccatggc agcggttcta gtctagcggc cgcaactgat cttggc        476


<210> SEQ ID NO 30
<211> LENGTH: 473
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(380)
<223> OTHER INFORMATION: a, c, t, g, unknown or other

<400> SEQUENCE: 30

gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctcgcgtt accgaagact    180

ctgcgcgtct gtcttggacc gcgccggacg cggcgttcga ctctttcctg atccagtacc    240

aggaatctga aaaagttggt gaagcgatcg tgctgaccgt tccgggttct gaacgttctt    300

acgacctgac cggtctgaaa ccgggtaccg aatacaccgt ttctatctac ggtgttnnnn    360

nnnnnnnnnn nnnnnnnnnn tctaacccgc tgtctgcgat cttcaccacc ggcggtcacc    420

atcaccatca ccatggcagc ggttctagtc tagcggccgc aactgatctt ggc           473


<210> SEQ ID NO 31
<211> LENGTH: 470
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(377)
<223> OTHER INFORMATION: a, c, t, g, unknown or other
```

-continued

<400> SEQUENCE: 31

```
gtgacacggc ggttagaacg cggctacaat taatacataa ccccatcccc ctgttgacaa     60

ttaatcatcg gctcgtataa tgtgtggaat tgtgagcgga taacaatttc acacaggaaa    120

caggatctac catgctgccg gcgccgaaaa acctggttgt ttctcgcgtt accgaagact    180

ctgcgcgtct gtcttggacc gcgccggacg cggcgttcga ctctttcctg atccagtacc    240

aggaatctga aaaagttggt gaagcgatcg tgctgaccgt tccgggttct gaacgttctt    300

acgacctgac cggtctgaaa ccgggtaccg aatacaccgt ttctatctac ggtgttnnnn    360

nnnnnnnnnn nnnnnnntct aacccgctgt ctgcgatctt caccaccggc ggtcaccatc    420

accatcacca tggcagcggt tctagtctag cggccgcaac tgatcttggc               470
```

<210> SEQ ID NO 32
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Lys Ser Ser Ser Glu Ala Thr Asn Ile Thr Pro Lys His Asn Met Lys
1               5                   10                  15

Ala Phe Leu Asp Glu Leu Lys Ala Glu Asn Ile Lys Lys Phe Leu His
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Thr His Tyr Asp Val Leu Leu Ser Tyr Pro Asn Lys Thr
65                  70                  75                  80

His Pro Asn Tyr Ile Ser Ile Ile Asn Glu Asp Gly Asn Glu Ile Phe
                85                  90                  95

Asn Thr Ser Leu Phe Glu Pro Pro Pro Ala Gly Tyr Glu Asn Val Ser
            100                 105                 110

Asp Ile Val Pro Pro Phe Ser Ala Phe Ser Pro Gln Gly Met Pro Glu
        115                 120                 125

Gly Asp Leu Val Tyr Val Asn Tyr Ala Arg Thr Glu Asp Phe Phe Lys
    130                 135                 140

Leu Glu Arg Asp Met Lys Ile Asn Cys Ser Gly Lys Ile Val Ile Ala
145                 150                 155                 160

Arg Tyr Gly Lys Val Phe Arg Gly Asn Lys Val Lys Asn Ala Gln Leu
                165                 170                 175

Ala Gly Ala Thr Gly Val Ile Leu Tyr Ser Asp Pro Asp Asp Tyr Phe
            180                 185                 190

Ala Pro Gly Val Lys Ser Tyr Pro Asp Gly Trp Asn Leu Pro Gly Gly
        195                 200                 205

Gly Val Gln Arg Gly Asn Ile Leu Asn Leu Asn Gly Ala Gly Asp Pro
    210                 215                 220

Leu Thr Pro Gly Tyr Pro Ala Asn Glu Tyr Ala Tyr Arg Arg Gly Met
225                 230                 235                 240

Ala Glu Ala Val Gly Leu Pro Ser Ile Pro Val His Pro Ile Gly Tyr
                245                 250                 255

Tyr Asp Ala Gln Lys Leu Leu Glu Lys Met Gly Gly Ser Ala Ser Pro
            260                 265                 270
```

-continued

```
Asp Ser Ser Trp Arg Gly Ser Leu Lys Val Pro Tyr Asn Val Gly Pro
        275                 280                 285

Gly Phe Thr Gly Asn Phe Ser Thr Gln Lys Val Lys Met His Ile His
    290                 295                 300

Ser Thr Ser Glu Val Thr Arg Ile Tyr Asn Val Ile Gly Thr Leu Arg
305                 310                 315                 320

Gly Ala Val Glu Pro Asp Arg Tyr Val Ile Leu Gly Gly His Arg Asp
                325                 330                 335

Ser Trp Val Phe Gly Gly Ile Asp Pro Gln Ser Gly Ala Ala Val Val
            340                 345                 350

His Glu Ile Val Arg Ser Phe Gly Met Leu Lys Lys Glu Gly Trp Arg
        355                 360                 365

Pro Arg Arg Thr Ile Leu Phe Ala Ser Trp Asp Ala Glu Glu Phe Gly
    370                 375                 380

Leu Leu Gly Ser Thr Glu Trp Ala Glu Glu Asn Ser Arg Leu Leu Gln
385                 390                 395                 400

Glu Arg Gly Val Ala Tyr Ile Asn Ala Asp Ser Ser Ile Glu Gly Asn
                405                 410                 415

Tyr Thr Leu Arg Val Asp Cys Thr Pro Leu Met Tyr Ser Leu Val Tyr
            420                 425                 430

Asn Leu Thr Lys Glu Leu Glu Ser Pro Asp Glu Gly Phe Glu Gly Lys
        435                 440                 445

Ser Leu Tyr Glu Ser Trp Thr Lys Lys Ser Pro Ser Pro Glu Phe Ser
    450                 455                 460

Gly Met Pro Arg Ile Ser Lys Leu Gly Ser Gly Asn Asp Phe Glu Val
465                 470                 475                 480

Phe Phe Gln Arg Leu Gly Ile Ala Ser Gly Arg Ala Arg Tyr Thr Lys
                485                 490                 495

Asn Trp Glu Thr Asn Lys Phe Ser Ser Tyr Pro Leu Tyr His Ser Val
            500                 505                 510

Tyr Glu Thr Tyr Glu Leu Val Glu Lys Phe Tyr Asp Pro Met Phe Lys
        515                 520                 525

Tyr His Leu Thr Val Ala Gln Val Arg Gly Gly Met Val Phe Glu Leu
    530                 535                 540

Ala Asn Ser Val Val Leu Pro Phe Asp Cys Arg Asp Tyr Ala Val Val
545                 550                 555                 560

Leu Arg Lys Tyr Ala Asp Lys Ile Tyr Asn Ile Ser Met Lys His Pro
                565                 570                 575

Gln Glu Met Lys Thr Tyr Ser Val Ser Phe Asp Ser Leu Phe Ser Ala
            580                 585                 590

Val Lys Asn Phe Thr Glu Ile Ala Ser Lys Phe Ser Glu Arg Leu Arg
        595                 600                 605

Asp Phe Asp Lys Ser Asn Pro Ile Leu Leu Arg Met Met Asn Asp Gln
    610                 615                 620

Leu Met Phe Leu Glu Arg Ala Phe Ile Asp Pro Leu Gly Leu Pro Asp
625                 630                 635                 640

Arg Pro Phe Tyr Arg His Val Ile Tyr Ala Pro Ser Ser His Asn Lys
                645                 650                 655

Tyr Ala Gly Glu Ser Phe Pro Gly Ile Tyr Asp Ala Leu Phe Asp Ile
            660                 665                 670

Glu Ser Lys Val Asp Pro Ser Gln Ala Trp Gly Glu Val Lys Arg Gln
        675                 680                 685
```

```
Ile Ser Ile Ala Thr Phe Thr Val Gln Ala Ala Ala Glu Thr Leu Ser
    690                 695                 700

Glu Val Ala
705


<210> SEQ ID NO 33
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Ser Ser Asn Glu Ala Thr Asn Ile Thr Pro Lys His Asn Met Lys
1               5                   10                  15

Ala Phe Leu Asp Glu Leu Lys Ala Glu Asn Ile Lys Lys Phe Leu Tyr
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Ala His Tyr Asp Val Leu Leu Ser Tyr Pro Asn Lys Thr
65                  70                  75                  80

His Pro Asn Tyr Ile Ser Ile Ile Asn Glu Asp Gly Asn Glu Ile Phe
                85                  90                  95

Asn Thr Ser Leu Phe Glu Pro Pro Pro Pro Gly Tyr Glu Asn Val Leu
            100                 105                 110

Asp Ile Val Pro Pro Phe Ser Ala Phe Ser Pro Gln Gly Met Pro Glu
        115                 120                 125

Gly Asp Leu Val Tyr Val Asn Tyr Ala Arg Thr Glu Asp Phe Phe Lys
    130                 135                 140

Leu Glu Arg Asp Met Lys Ile Asn Cys Ser Gly Lys Ile Val Ile Ala
145                 150                 155                 160

Arg Tyr Gly Lys Val Phe Arg Gly Asn Lys Val Lys Asn Ala Gln Leu
                165                 170                 175

Ala Gly Ala Lys Gly Val Ile Leu Tyr Ser Asp Pro Ala Asp Tyr Phe
            180                 185                 190

Ala Pro Gly Val Lys Ser Tyr Pro Asp Gly Trp Asn Leu Pro Gly Gly
        195                 200                 205

Gly Val Gln Arg Gly Asn Ile Leu Asn Leu Asn Gly Ala Gly Asp Pro
    210                 215                 220

Leu Thr Pro Gly Tyr Pro Ala Asn Glu Tyr Ala Tyr Arg His Gly Ile
225                 230                 235                 240

Ala Glu Ala Val Gly Leu Pro Ser Ile Pro Val His Pro Ile Gly Tyr
                245                 250                 255

Tyr Asp Ala Gln Lys Leu Leu Glu Lys Met Gly Gly Ser Ala Pro Pro
            260                 265                 270

Asp Ser Ser Trp Arg Gly Ser Leu Lys Val Pro Tyr Asn Val Gly Pro
        275                 280                 285

Gly Phe Thr Gly Asn Phe Ser Thr Gln Lys Val Lys Met His Ile His
    290                 295                 300

Ser Thr Asn Glu Val Thr Arg Ile Tyr Asn Val Ile Gly Thr Leu Arg
305                 310                 315                 320

Gly Ala Val Glu Pro Asp Arg Tyr Val Ile Leu Gly Gly His Arg Asp
                325                 330                 335
```

```
Ser Trp Val Phe Gly Gly Ile Asp Pro Gln Ser Gly Ala Ala Val Val
            340                 345                 350

His Glu Ile Val Arg Ser Phe Gly Thr Leu Lys Lys Glu Gly Trp Arg
        355                 360                 365

Pro Arg Arg Thr Ile Leu Phe Ala Ser Trp Asp Ala Glu Glu Phe Gly
    370                 375                 380

Leu Leu Gly Ser Thr Glu Trp Ala Glu Glu Asn Ser Arg Leu Leu Gln
385                 390                 395                 400

Glu Arg Gly Val Ala Tyr Ile Asn Ala Asp Ser Ser Ile Glu Gly Asn
                405                 410                 415

Tyr Thr Leu Arg Val Asp Cys Thr Pro Leu Met Tyr Ser Leu Val Tyr
            420                 425                 430

Asn Leu Thr Lys Glu Leu Lys Ser Pro Asp Glu Gly Phe Glu Gly Lys
        435                 440                 445

Ser Leu Tyr Glu Ser Trp Thr Lys Lys Ser Pro Ser Pro Glu Phe Ser
    450                 455                 460

Gly Met Pro Arg Ile Ser Lys Leu Gly Ser Gly Asn Asp Phe Glu Val
465                 470                 475                 480

Phe Phe Gln Arg Leu Gly Ile Ala Ser Gly Arg Ala Arg Tyr Thr Lys
                485                 490                 495

Asn Trp Glu Thr Asn Lys Phe Ser Gly Tyr Pro Leu Tyr His Ser Val
            500                 505                 510

Tyr Glu Thr Tyr Glu Leu Val Glu Lys Phe Tyr Asp Pro Met Phe Lys
        515                 520                 525

Tyr His Leu Thr Val Ala Gln Val Arg Gly Gly Met Val Phe Glu Leu
    530                 535                 540

Ala Asn Ser Ile Val Leu Pro Phe Asp Cys Arg Asp Tyr Ala Val Val
545                 550                 555                 560

Leu Arg Lys Tyr Ala Asp Lys Ile Tyr Asn Ile Ser Met Lys His Pro
                565                 570                 575

Gln Glu Met Lys Thr Tyr Ser Val Ser Phe Asp Ser Leu Phe Ser Ala
            580                 585                 590

Val Lys Asn Phe Thr Glu Ile Ala Ser Lys Phe Thr Glu Arg Leu Gln
        595                 600                 605

Asp Phe Asp Lys Ser Asn Pro Ile Leu Leu Arg Met Met Asn Asp Gln
    610                 615                 620

Leu Met Phe Leu Glu Arg Ala Phe Ile Asp Pro Leu Gly Leu Pro Asp
625                 630                 635                 640

Arg Pro Phe Tyr Arg His Val Ile Tyr Ala Pro Ser Ser His Asn Lys
                645                 650                 655

Tyr Ala Gly Glu Ser Phe Pro Gly Ile Tyr Asp Ala Leu Phe Asp Ile
            660                 665                 670

Glu Ser Lys Val Asp Pro Ser Lys Ala Trp Gly Asp Val Lys Arg Gln
        675                 680                 685

Ile Ser Val Ala Ala Phe Thr Val Gln Ala Ala Ala Glu Thr Leu Ser
    690                 695                 700

Glu Val Ala
705
```

<210> SEQ ID NO 34
<211> LENGTH: 6
<212> TYPE: PRT
<213> ORGANISM: Artificial Sequence
<220> FEATURE:

<223> OTHER INFORMATION: Description of Artificial Sequence:
hexahistidine tag

<400> SEQUENCE: 34

His His His His His His
1 5

<210> SEQ ID NO 35
<211> LENGTH: 91
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 35

Leu Pro Ala Pro Lys Asn Leu Val Val Ser Arg Val Thr Glu Asp Ser
1 5 10 15

Ala Arg Leu Ser Trp Asp Ile Asp Glu Gln Arg Asp Trp Phe Asp Ser
20 25 30

Phe Leu Ile Gln Tyr Gln Glu Ser Glu Lys Val Gly Glu Ala Ile Val
35 40 45

Leu Thr Val Pro Gly Ser Glu Arg Ser Tyr Asp Leu Thr Gly Leu Lys
50 55 60

Pro Gly Thr Glu Tyr Thr Val Ser Ile Tyr Gly Val Tyr His Val Tyr
65 70 75 80

Arg Ser Asn Pro Leu Ser Ala Ile Phe Thr Thr
85 90

<210> SEQ ID NO 36
<211> LENGTH: 91
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 36

Leu Pro Ala Pro Lys Asn Leu Val Val Ser Arg Val Thr Glu Asp Ser
1 5 10 15

Ala Arg Leu Ser Trp Thr Ile Asp Glu Gln Arg Asp Trp Phe Asp Ser
20 25 30

Phe Leu Ile Gln Tyr Gln Glu Ser Glu Lys Val Gly Glu Ala Ile Val
35 40 45

Leu Thr Val Pro Gly Ser Glu Arg Ser Tyr Asp Leu Thr Gly Leu Lys
50 55 60

Pro Gly Thr Glu Tyr Thr Val Ser Ile Tyr Gly Val Tyr His Val Tyr
65 70 75 80

Arg Ser Asn Pro Leu Ser Ala Ile Phe Thr Thr
85 90

<210> SEQ ID NO 37
<211> LENGTH: 91
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 37

Leu Pro Ala Pro Lys Asn Leu Val Val Ser Arg Val Thr Glu Asp Ser
1 5 10 15

Ala Arg Leu Ser Trp Val Ile Asp Glu Gln Arg Asp Trp Phe Asp Ser
20 25 30

Phe Leu Ile Gln Tyr Gln Glu Ser Glu Lys Val Gly Glu Ala Ile Val
35 40 45

Leu Thr Val Pro Gly Ser Glu Arg Ser Tyr Asp Leu Thr Gly Leu Lys
50 55 60

Pro Gly Thr Glu Tyr Thr Val Ser Ile Tyr Gly Val Tyr His Val Tyr
65 70 75 80

Arg Ser Asn Pro Leu Ser Ala Ile Phe Thr Thr
85 90

<210> SEQ ID NO 38
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 38

Leu Pro Ala Pro Lys Asn Leu Val Val Ser Arg Val Thr Glu Asp Ser
1 5 10 15

Ala Arg Leu Ser Trp Thr Ile Asp Glu Gln Arg Asp Trp Phe Glu Ser
20 25 30

Phe Leu Ile Gln Tyr Gln Glu Ser Glu Lys Val Gly Glu Ala Ile Val
35 40 45

Leu Thr Val Pro Gly Ser Glu Arg Ser Tyr Asp Leu Thr Gly Leu Lys
50 55 60

Pro Gly Thr Glu Tyr Thr Val Ser Ile Tyr Gly Val Tyr His Val Tyr
65 70 75 80

Arg Ser Asn Pro Leu Ser Ala Ile Phe Thr Thr
85 90

<210> SEQ ID NO 39
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

Leu Pro Ala Pro Lys Asn Leu Val Val Ser Arg Val Thr Glu Asp Ser
1 5 10 15

Ala Arg Leu Ser Trp Ala Ile Asp Glu Gln Arg Asp Trp Phe Glu Ser
20 25 30

Phe Leu Ile Gln Tyr Gln Glu Ser Glu Lys Val Gly Glu Ala Ile Val
35 40 45

Leu Thr Val Pro Gly Ser Glu Arg Ser Tyr Asp Leu Thr Gly Leu Lys
50 55 60

Pro Gly Thr Glu Tyr Thr Val Ser Ile Tyr Gly Val Tyr His Val Tyr
65 70 75 80

Arg Ser Asn Pro Leu Ser Ala Ile Phe Thr Thr
85 90

<210> SEQ ID NO 40
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90
```

<210> SEQ ID NO 41
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 42
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Gly Tyr Trp Glu Trp Asp Asp Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80
```

Phe Pro Leu Ser Ala Ile Phe Thr Thr
85

<210> SEQ ID NO 43
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Pro
20 25 30

Ile Gly Tyr Trp Glu Trp Asp Asp Asp Gly Glu Ala Ile Val Leu Thr
35 40 45

Val Pro Gly Ser Glu Arg Ser Tyr Asp Leu Thr Gly Leu Lys Pro Gly
50 55 60

Thr Glu Tyr His Val Tyr Ile Ala Gly Val Lys Gly Gly Gln Trp Ser
65 70 75 80

Phe Pro Leu Ser Ala Ile Phe Thr Thr
85

<210> SEQ ID NO 44
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Pro
20 25 30

Ile Gly Tyr Trp Glu Trp Asp Asp Asp Gly Glu Ala Ile Val Leu Thr
35 40 45

Val Pro Gly Ser Glu Arg Ser Tyr Asp Leu Thr Gly Leu Lys Pro Gly
50 55 60

Thr Glu Tyr Trp Val Tyr Ile Ala Gly Val Lys Gly Gly Gln Trp Ser
65 70 75 80

Phe Pro Leu Ser Ala Ile Phe Thr Thr
85

<210> SEQ ID NO 45
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Leu Pro Ala Pro Lys Asn Leu Val Val Ser Arg Val Thr Glu Asp Ser
1 5 10 15

Ala Arg Leu Ser Trp Gly Glu Gln Phe Thr Ile Phe Asp Ser Phe Leu
20 25 30

Ile Gln Tyr Gln Glu Ser Glu Lys Val Gly Glu Ala Ile Val Leu Thr 35 40 45

Val Pro Gly Ser Glu Arg Ser Tyr Asp Leu Thr Gly Leu Lys Pro Gly
50 55 60

Thr Glu Tyr Thr Val Ser Ile Tyr Gly Ala Ser Gly Tyr Glu Trp Phe
65 70 75 80

His Ala Phe Gly Ser Ser Asn Pro Leu Ser Ala Ile Phe Thr Thr
85 90 95

<210> SEQ ID NO 46
<211> LENGTH: 95
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

Leu Pro Ala Pro Lys Asn Leu Val Val Ser Arg Val Thr Glu Asp Ser
1 5 10 15

Ala Arg Leu Ser Trp Glu Trp Trp Val Ile Pro Gly Asp Phe Asp Ser
20 25 30

Phe Leu Ile Gln Tyr Gln Glu Ser Glu Lys Val Gly Glu Ala Ile Val
35 40 45

Leu Thr Val Pro Gly Ser Glu Arg Ser Tyr Asp Leu Thr Gly Leu Lys
50 55 60

Pro Gly Thr Glu Tyr Thr Val Ser Ile Tyr Gly Val Val Asn Ser Gly
65 70 75 80

Gln Trp Asn Asp Thr Ser Asn Pro Leu Ser Ala Ile Phe Thr Thr
85 90 95

<210> SEQ ID NO 47
<211> LENGTH: 90
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Glu Arg Ser Tyr Asp Leu Thr Gly Leu Lys Pro Gly
50 55 60

Thr Glu Tyr Pro Val Tyr Ile Ala Gly Val Lys Gly Gly Gln Trp Ser
65 70 75 80

Phe Pro Leu Ser Ala Ile Phe Thr Thr Cys
85 90

<210> SEQ ID NO 48
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Glu Arg Ser Tyr Asp Leu Thr Gly Leu Cys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 49
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 50
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Pro Ala Pro Lys Asn Leu Val Val Ser Cys Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 51
```

<211> LENGTH: 97
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 51

```
Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Cys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr Gly Gly His His His His His
                85                  90                  95

His
```

<210> SEQ ID NO 52
<211> LENGTH: 199
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

```
Met Ser His His His His His His Ser Ser Gly Glu Asn Leu Tyr Phe
1               5                   10                  15

Gln Ser Lys Pro His Ile Asp Asn Tyr Leu His Asp Lys Asp Lys Asp
            20                  25                  30

Glu Lys Ile Glu Gln Tyr Asp Lys Asn Val Lys Glu Gln Ala Ser Lys
        35                  40                  45

Asp Lys Lys Gln Gln Ala Lys Pro Gln Ile Pro Lys Asp Lys Ser Lys
    50                  55                  60

Val Ala Gly Tyr Ile Glu Ile Pro Asp Ala Asp Ile Lys Glu Pro Val
65                  70                  75                  80

Tyr Pro Gly Pro Ala Thr Arg Glu Gln Leu Asn Arg Gly Val Ser Phe
                85                  90                  95

Ala Glu Glu Asn Glu Ser Leu Asp Asp Gln Asn Ile Ser Ile Ala Gly
            100                 105                 110

His Thr Phe Ile Asp Arg Pro Asn Tyr Gln Phe Thr Asn Leu Lys Ala
        115                 120                 125

Ala Lys Lys Gly Ser Met Val Tyr Phe Lys Val Gly Asn Glu Thr Arg
    130                 135                 140

Lys Tyr Lys Met Thr Ser Ile Arg Asn Val Lys Pro Thr Ala Val Glu
145                 150                 155                 160

Val Leu Asp Glu Gln Lys Gly Lys Asp Lys Gln Leu Thr Leu Ile Thr
                165                 170                 175

Cys Asp Asp Tyr Asn Glu Glu Thr Gly Val Trp Glu Thr Arg Lys Ile
            180                 185                 190

Phe Val Ala Thr Glu Val Lys
        195
```

<210> SEQ ID NO 53
<211> LENGTH: 182
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

```
Ser Lys Pro His Ile Asp Asn Tyr Leu His Asp Lys Asp Lys Asp Glu
1               5                   10                  15

Lys Ile Glu Gln Tyr Asp Lys Asn Val Lys Glu Gln Ala Ser Lys Asp
            20                  25                  30

Lys Lys Gln Gln Ala Lys Pro Gln Ile Pro Lys Asp Lys Ser Lys Val
        35                  40                  45

Ala Gly Tyr Ile Glu Ile Pro Asp Ala Asp Ile Lys Glu Pro Val Tyr
    50                  55                  60

Pro Gly Pro Ala Thr Arg Glu Gln Leu Asn Arg Gly Val Ser Phe Ala
65                  70                  75                  80

Glu Glu Asn Glu Ser Leu Asp Asp Gln Asn Ile Ser Ile Ala Gly His
                85                  90                  95

Thr Phe Ile Asp Arg Pro Asn Tyr Gln Phe Thr Asn Leu Lys Ala Ala
            100                 105                 110

Lys Lys Gly Ser Met Val Tyr Phe Lys Val Gly Asn Glu Thr Arg Lys
        115                 120                 125

Tyr Lys Met Thr Ser Ile Arg Asn Val Lys Pro Thr Ala Val Glu Val
    130                 135                 140

Leu Asp Glu Gln Lys Gly Lys Asp Lys Gln Leu Thr Leu Ile Thr Cys
145                 150                 155                 160

Asp Asp Tyr Asn Glu Glu Thr Gly Val Trp Glu Thr Arg Lys Ile Phe
                165                 170                 175

Val Ala Thr Glu Val Lys
            180
```

<210> SEQ ID NO 54
<211> LENGTH: 7
<212> TYPE: PRT
<213> ORGANISM: Unknown
<220> FEATURE:
<223> OTHER INFORMATION: Description of Unknown: TEV protease cleavage
site peptide

<400> SEQUENCE: 54

```
Glu Asn Leu Tyr Phe Gln Ser
1               5
```

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

```
Lys Gly Gly His Arg Ser Asn
1               5
```

<210> SEQ ID NO 56
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 56

Asp Ile Asp Glu Gln Arg Asp Trp
1 5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Thr Ile Asp Glu Gln Arg Asp Trp
1 5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Val Ile Asp Glu Gln Arg Asp Trp
1 5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Ala Ile Asp Glu Gln Arg Asp Trp
1 5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Glu Trp Trp Val Ile Pro Gly Asp
1 5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Glu Gln Phe Thr Ile
1 5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Thr Ala Pro Asp Ala Ala
1 5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Phe Asp Ser Phe Leu Ile Gln Tyr Gln Glu
1 5 10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Phe Glu Ser Phe Leu Ile Gln Tyr Gln Glu
1 5 10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 65

Phe Asp Ser Phe Ala Ile Gly Tyr Trp Glu
1 5 10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Phe Asp Ser Phe Pro Ile Gly Tyr Trp Glu
1 5 10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Phe Asp Ser Phe Thr Ile Gly Tyr Trp Glu
1 5 10

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Ser Glu Lys Val Gly Glu
1 5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Trp Asp Asp Asp Gly Glu
1 5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Thr Glu Tyr Thr Val Ser Ile Tyr Gly Val
1 5 10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Thr Glu Tyr Thr Val Ser Ile Tyr Gly
1 5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Thr Glu Tyr Pro Val Tyr Ile Ala Gly Val
1 5 10

<210> SEQ ID NO 73
<211> LENGTH: 10

<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

```
Thr Glu Tyr Trp Val Tyr Ile Ala Gly Val
1               5                   10
```

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

```
Thr Glu Tyr His Val Tyr Ile Ala Gly Val
1               5                   10
```

<210> SEQ ID NO 75
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 75

```
Leu Pro Ala Pro Lys Asn Leu Val Val Ser Arg Val Thr Glu Asp Ser
1               5                   10                  15

Ala Arg Leu Ser Trp Ala Ala Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90
```

<210> SEQ ID NO 76
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 76

```
Leu Pro Ala Pro Lys Asn Leu Val Val Ser Arg Val Thr Glu Asp Ser
1               5                   10                  15

Ala Arg Leu Ser Trp Ala Ile Ala Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80
```

```
Arg Ser Asn Pro Leu Ser Ala Ile Phe Thr Thr
                85                  90


<210> SEQ ID NO 77
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Pro Ala Pro Lys Asn Leu Val Val Ser Arg Val Thr Glu Asp Ser
1               5                   10                  15

Ala Arg Leu Ser Trp Ala Ile Asp Ala Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 78
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Leu Pro Ala Pro Lys Asn Leu Val Val Ser Arg Val Thr Glu Asp Ser
1               5                   10                  15

Ala Arg Leu Ser Trp Ala Ile Asp Glu Ala Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 79
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Leu Pro Ala Pro Lys Asn Leu Val Val Ser Arg Val Thr Glu Asp Ser
1               5                   10                  15

Ala Arg Leu Ser Trp Ala Ile Asp Glu Gln Ala Asp Trp Phe Glu Ser
            20                  25                  30
```

-continued

```
Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 80
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Ala Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 81
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Ala Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 82
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 82

Leu Pro Ala Pro Lys Asn Leu Val Val Ser Arg Val Thr Glu Asp Ser
1 5 10 15

Ala Arg Leu Ser Trp Ala Ile Asp Glu Gln Arg Asp Trp Phe Glu Ser
20 25 30

Phe Leu Ile Gln Tyr Gln Glu Ser Glu Lys Val Gly Glu Ala Ile Val
35 40 45

Leu Thr Val Pro Gly Ser Cys Arg Ser Tyr Asp Leu Thr Gly Leu Lys
50 55 60

Pro Gly Thr Glu Tyr Thr Val Ser Ile Tyr Gly Val Ala His Val Tyr
65 70 75 80

Arg Ser Asn Pro Leu Ser Ala Ile Phe Thr Thr
85 90

<210> SEQ ID NO 83
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Leu Pro Ala Pro Lys Asn Leu Val Val Ser Arg Val Thr Glu Asp Ser
1 5 10 15

Ala Arg Leu Ser Trp Ala Ile Asp Glu Gln Arg Asp Trp Phe Glu Ser
20 25 30

Phe Leu Ile Gln Tyr Gln Glu Ser Glu Lys Val Gly Glu Ala Ile Val
35 40 45

Leu Thr Val Pro Gly Ser Cys Arg Ser Tyr Asp Leu Thr Gly Leu Lys
50 55 60

Pro Gly Thr Glu Tyr Thr Val Ser Ile Tyr Gly Val Tyr Ala Val Tyr
65 70 75 80

Arg Ser Asn Pro Leu Ser Ala Ile Phe Thr Thr
85 90

<210> SEQ ID NO 84
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

Leu Pro Ala Pro Lys Asn Leu Val Val Ser Arg Val Thr Glu Asp Ser
1 5 10 15

Ala Arg Leu Ser Trp Ala Ile Asp Glu Gln Arg Asp Trp Phe Glu Ser
20 25 30

Phe Leu Ile Gln Tyr Gln Glu Ser Glu Lys Val Gly Glu Ala Ile Val
35 40 45

Leu Thr Val Pro Gly Ser Cys Arg Ser Tyr Asp Leu Thr Gly Leu Lys
50 55 60

Pro Gly Thr Glu Tyr Thr Val Ser Ile Tyr Gly Val Tyr His Ala Tyr
65 70 75 80

Arg Ser Asn Pro Leu Ser Ala Ile Phe Thr Thr
85 90

<210> SEQ ID NO 85
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Ala
65                  70                  75                  80

Arg Ser Asn Pro Leu Ser Ala Ile Phe Thr Thr
                85                  90
```

<210> SEQ ID NO 86
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Ala Ser Asn Pro Leu Ser Ala Ile Phe Thr Thr
                85                  90
```

<210> SEQ ID NO 87
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Ala Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60
```

```
Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 88
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 89
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 90
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Leu Pro Ala Pro Lys Asn Leu Val Val Ser Arg Val Thr Glu Asp Ser
1               5                   10                  15
```

-continued

```
Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90


<210> SEQ ID NO 91
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90


<210> SEQ ID NO 92
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90


<210> SEQ ID NO 93
<211> LENGTH: 92
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 93

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90
```

<210> SEQ ID NO 94
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Arg Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 95
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Lys Val Tyr Ile Ala Gly Val Lys Gly Gly Gln Trp Ser
65                  70                  75                  80

Phe Pro Leu Ser Ala Ile Phe Thr Thr
```

85

<210> SEQ ID NO 96
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Glu Val Tyr Ile Ala Gly Val Lys Gly Gly Gln Trp Ser
65 70 75 80

Phe Pro Leu Ser Ala Ile Phe Thr Thr
85

<210> SEQ ID NO 97
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr His Val Tyr Ile Ala Gly Val Lys Gly Gly Gln Trp Ser
65 70 75 80

Phe Pro Leu Ser Ala Ile Phe Thr Thr
85

<210> SEQ ID NO 98
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

```
Val Pro Gly Ser Cys Arg Ser Tyr Asp Leu Thr Gly Leu Lys Pro Gly
    50                  55                  60

Thr Glu Tyr Asp Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 99
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Ala Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 100
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Gly Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 101
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101
```

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Val Val Tyr Ile Ala Gly Val Lys Gly Gly Gln Trp Ser
65 70 75 80

Phe Pro Leu Ser Ala Ile Phe Thr Thr
85

<210> SEQ ID NO 102
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Leu Val Tyr Ile Ala Gly Val Lys Gly Gly Gln Trp Ser
65 70 75 80

Phe Pro Leu Ser Ala Ile Phe Thr Thr
85

<210> SEQ ID NO 103
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Ile Val Tyr Ile Ala Gly Val Lys Gly Gly Gln Trp Ser
65 70 75 80

Phe Pro Leu Ser Ala Ile Phe Thr Thr
85

<210> SEQ ID NO 104
<211> LENGTH: 89

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Phe Val Tyr Ile Ala Gly Val Lys Gly Gly Gln Trp Ser
65 70 75 80

Phe Pro Leu Ser Ala Ile Phe Thr Thr
85

<210> SEQ ID NO 105
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Trp Val Tyr Ile Ala Gly Val Lys Gly Gly Gln Trp Ser
65 70 75 80

Phe Pro Leu Ser Ala Ile Phe Thr Thr
85

<210> SEQ ID NO 106
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Asn Val Tyr Ile Ala Gly Val Lys Gly Gly Gln Trp Ser 65 70 75 80

Phe Pro Leu Ser Ala Ile Phe Thr Thr
85

<210> SEQ ID NO 107
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Gln Val Tyr Ile Ala Gly Val Lys Gly Gly Gln Trp Ser
65 70 75 80

Phe Pro Leu Ser Ala Ile Phe Thr Thr
85

<210> SEQ ID NO 108
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Ser Val Tyr Ile Ala Gly Val Lys Gly Gly Gln Trp Ser
65 70 75 80

Phe Pro Leu Ser Ala Ile Phe Thr Thr
85

<210> SEQ ID NO 109
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Thr Val Tyr Ile Ala Gly Val Lys Gly Gly Gln Trp Ser
65 70 75 80

Phe Pro Leu Ser Ala Ile Phe Thr Thr
85

<210> SEQ ID NO 110
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Tyr Val Tyr Ile Ala Gly Val Lys Gly Gly Gln Trp Ser
65 70 75 80

Phe Pro Leu Ser Ala Ile Phe Thr Thr
85

<210> SEQ ID NO 111
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 111

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Ala Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Pro Val Tyr Ile Ala Gly Val Lys Gly Gly Gln Trp Ser
65 70 75 80

Phe Pro Leu Ser Ala Ile Phe Thr Thr
85

<210> SEQ ID NO 112
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ser Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 113
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Thr Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 114
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Ser Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 115
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Tyr Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 116
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 116

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Phe Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 117
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Leu Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
```

50 55 60

Thr Glu Tyr Pro Val Tyr Ile Ala Gly Val Lys Gly Gly Gln Trp Ser
65 70 75 80

Phe Pro Leu Ser Ala Ile Phe Thr Thr
85

<210> SEQ ID NO 118
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Tyr Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Pro Val Tyr Ile Ala Gly Val Lys Gly Gly Gln Trp Ser
65 70 75 80

Phe Pro Leu Ser Ala Ile Phe Thr Thr
85

<210> SEQ ID NO 119
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 119

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Phe Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Pro Val Tyr Ile Ala Gly Val Lys Gly Gly Gln Trp Ser
65 70 75 80

Phe Pro Leu Ser Ala Ile Phe Thr Thr
85

<210> SEQ ID NO 120
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Leu Pro Ala Pro Lys Asn Leu Val Val Ser Arg Val Thr Glu Asp Ser
1 5 10 15

```
Ala Arg Leu Ser Trp Thr Ala Pro Asp Ala Ala Phe Asp Ser Phe Ala
            20                  25                  30

Ile Gly Tyr Trp Glu Leu Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 121
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Tyr Ser
65                  70                  75                  80

Phe Pro Leu Ser Ala Ile Phe Thr Thr
                85
```

<210> SEQ ID NO 122
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Phe Ser
65                  70                  75                  80

Phe Pro Leu Ser Ala Ile Phe Thr Thr
                85
```

<210> SEQ ID NO 123
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 123

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Ala
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr Pro Val Tyr Ile Ala Gly Val Lys Gly Gly Gln Leu Ser
65 70 75 80

Phe Pro Leu Ser Ala Ile Phe Thr Thr
85

<210> SEQ ID NO 124
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 124

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Arg
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr His Val Tyr Ile Ala Gly Val Lys Gly Gly Gln Trp Ser
65 70 75 80

Phe Pro Leu Ser Ala Ile Phe Thr Thr
85

<210> SEQ ID NO 125
<211> LENGTH: 89
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 125

Leu Pro Ala Pro Lys Asn Leu Val Val Ser Arg Val Thr Glu Asp Ser
1 5 10 15

Ala Arg Leu Ser Trp Thr Ala Pro Asp Ala Ala Phe Asp Ser Phe Lys
20 25 30

Ile Gly Tyr Trp Glu Trp Asp Asp Asp Gly Glu Ala Ile Val Leu Thr
35 40 45

Val Pro Gly Ser Cys Arg Ser Tyr Asp Leu Thr Gly Leu Lys Pro Gly
50 55 60

Thr Glu Tyr His Val Tyr Ile Ala Gly Val Lys Gly Gly Gln Trp Ser
65 70 75 80

```
Phe Pro Leu Ser Ala Ile Phe Thr Thr
                85


<210> SEQ ID NO 126
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 127
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 128
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Gly Tyr Trp Glu Trp Asp Asp Asp Gly Glu Ala Ile Val Leu Thr
```

```
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 129
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 130
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 131
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131
```

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 132
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 133
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 134
```

<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 135
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 136
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60
```

```
Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 137
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 138
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 139
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
```

```
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 140
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85


<210> SEQ ID NO 141
<211> LENGTH: 700
<212> TYPE: PRT
<213> ORGANISM: Macaca fascicularis

<400> SEQUENCE: 141

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Ser Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Ala Gly Tyr Glu Asn Val Ser Asp Ile Val Pro Pro
```

```
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Thr Gly
    210                 215                 220

Val Ile Leu Tyr Ser Asp Pro Asp Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Met Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Ser Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Ser Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Met Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val Tyr Asn Leu Thr Lys Glu
465                 470                 475                 480

Leu Glu Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Ser Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575
```

```
Ala Gln Val Arg Gly Gly Met Val Phe Glu Leu Ala Asn Ser Val Val
            580                 585                 590

Leu Pro Phe Asp Cys Arg Asp Tyr Ala Val Val Leu Arg Lys Tyr Ala
        595                 600                 605

Asp Lys Ile Tyr Asn Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Arg Asp Phe Asp Lys Ser
                645                 650                 655

Asn Pro Ile Leu Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr
    690                 695                 700


<210> SEQ ID NO 142
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25


<210> SEQ ID NO 143
<211> LENGTH: 707
<212> TYPE: PRT
<213> ORGANISM: Homo sapiens

<400> SEQUENCE: 143

Lys Ser Ser Asn Glu Ala Thr Asn Ile Thr Pro Lys His Asn Met Lys
1               5                   10                  15

Ala Phe Leu Asp Glu Leu Lys Ala Glu Asn Ile Lys Lys Phe Leu Tyr
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Ala His Tyr Asp Val Leu Leu Ser Tyr Pro Asn Lys Thr
65                  70                  75                  80

His Pro Asn Tyr Ile Ser Ile Ile Asn Glu Asp Gly Asn Glu Ile Phe
                85                  90                  95

Asn Thr Ser Leu Phe Glu Pro Pro Pro Pro Gly Tyr Glu Asn Val Ser
            100                 105                 110

Asp Ile Val Pro Pro Phe Ser Ala Phe Ser Pro Gln Gly Met Pro Glu
        115                 120                 125

Gly Asp Leu Val Tyr Val Asn Tyr Ala Arg Thr Glu Asp Phe Phe Lys
    130                 135                 140

Leu Glu Arg Asp Met Lys Ile Asn Cys Ser Gly Lys Ile Val Ile Ala
145                 150                 155                 160
```

```
Arg Tyr Gly Lys Val Phe Arg Gly Asn Lys Val Lys Asn Ala Gln Leu
                165                 170                 175

Ala Gly Ala Lys Gly Val Ile Leu Tyr Ser Asp Pro Ala Asp Tyr Phe
            180                 185                 190

Ala Pro Gly Val Lys Ser Tyr Pro Asp Gly Trp Asn Leu Pro Gly Gly
        195                 200                 205

Gly Val Gln Arg Gly Asn Ile Leu Asn Leu Asn Gly Ala Gly Asp Pro
    210                 215                 220

Leu Thr Pro Gly Tyr Pro Ala Asn Glu Tyr Ala Tyr Arg Arg Gly Ile
225                 230                 235                 240

Ala Glu Ala Val Gly Leu Pro Ser Ile Pro Val His Pro Ile Gly Tyr
                245                 250                 255

Tyr Asp Ala Gln Lys Leu Leu Glu Lys Met Gly Gly Ser Ala Pro Pro
            260                 265                 270

Asp Ser Ser Trp Arg Gly Ser Leu Lys Val Pro Tyr Asn Val Gly Pro
        275                 280                 285

Gly Phe Thr Gly Asn Phe Ser Thr Gln Lys Val Lys Met His Ile His
    290                 295                 300

Ser Thr Asn Glu Val Thr Arg Ile Tyr Asn Val Ile Gly Thr Leu Arg
305                 310                 315                 320

Gly Ala Val Glu Pro Asp Arg Tyr Val Ile Leu Gly Gly His Arg Asp
                325                 330                 335

Ser Trp Val Phe Gly Gly Ile Asp Pro Gln Ser Gly Ala Ala Val Val
            340                 345                 350

His Glu Ile Val Arg Ser Phe Gly Thr Leu Lys Lys Glu Gly Trp Arg
        355                 360                 365

Pro Arg Arg Thr Ile Leu Phe Ala Ser Trp Asp Ala Glu Glu Phe Gly
    370                 375                 380

Leu Leu Gly Ser Thr Glu Trp Ala Glu Glu Asn Ser Arg Leu Leu Gln
385                 390                 395                 400

Glu Arg Gly Val Ala Tyr Ile Asn Ala Asp Ser Ser Ile Glu Gly Asn
                405                 410                 415

Tyr Thr Leu Arg Val Asp Cys Thr Pro Leu Met Tyr Ser Leu Val His
            420                 425                 430

Asn Leu Thr Lys Glu Leu Lys Ser Pro Asp Glu Gly Phe Glu Gly Lys
        435                 440                 445

Ser Leu Tyr Glu Ser Trp Thr Lys Lys Ser Pro Ser Pro Glu Phe Ser
    450                 455                 460

Gly Met Pro Arg Ile Ser Lys Leu Gly Ser Gly Asn Asp Phe Glu Val
465                 470                 475                 480

Phe Phe Gln Arg Leu Gly Ile Ala Ser Gly Arg Ala Arg Tyr Thr Lys
                485                 490                 495

Asn Trp Glu Thr Asn Lys Phe Ser Gly Tyr Pro Leu Tyr His Ser Val
            500                 505                 510

Tyr Glu Thr Tyr Glu Leu Val Glu Lys Phe Tyr Asp Pro Met Phe Lys
        515                 520                 525

Tyr His Leu Thr Val Ala Gln Val Arg Gly Gly Met Val Phe Glu Leu
    530                 535                 540

Ala Asn Ser Ile Val Leu Pro Phe Asp Cys Arg Asp Tyr Ala Val Val
545                 550                 555                 560

Leu Arg Lys Tyr Ala Asp Lys Ile Tyr Ser Ile Ser Met Lys His Pro
                565                 570                 575
```

Gln Glu Met Lys Thr Tyr Ser Val Ser Phe Asp Ser Leu Phe Ser Ala
580 585 590

Val Lys Asn Phe Thr Glu Ile Ala Ser Lys Phe Ser Glu Arg Leu Gln
595 600 605

Asp Phe Asp Lys Ser Asn Pro Ile Val Leu Arg Met Met Asn Asp Gln
610 615 620

Leu Met Phe Leu Glu Arg Ala Phe Ile Asp Pro Leu Gly Leu Pro Asp
625 630 635 640

Arg Pro Phe Tyr Arg His Val Ile Tyr Ala Pro Ser Ser His Asn Lys
645 650 655

Tyr Ala Gly Glu Ser Phe Pro Gly Ile Tyr Asp Ala Leu Phe Asp Ile
660 665 670

Glu Ser Lys Val Asp Pro Ser Lys Ala Trp Gly Glu Val Lys Arg Gln
675 680 685

Ile Tyr Val Ala Ala Phe Thr Val Gln Ala Ala Ala Glu Thr Leu Ser
690 695 700

Glu Val Ala
705

<210> SEQ ID NO 144
<211> LENGTH: 750
<212> TYPE: PRT
<213> ORGANISM: Homo sapiens

<400> SEQUENCE: 144

Met Trp Asn Leu Leu His Glu Thr Asp Ser Ala Val Ala Thr Ala Arg
1 5 10 15

Arg Pro Arg Trp Leu Cys Ala Gly Ala Leu Val Leu Ala Gly Gly Phe
20 25 30

Phe Leu Leu Gly Phe Leu Phe Gly Trp Phe Ile Lys Ser Ser Asn Glu
35 40 45

Ala Thr Asn Ile Thr Pro Lys His Asn Met Lys Ala Phe Leu Asp Glu
50 55 60

Leu Lys Ala Glu Asn Ile Lys Lys Phe Leu Tyr Asn Phe Thr Gln Ile
65 70 75 80

Pro His Leu Ala Gly Thr Glu Gln Asn Phe Gln Leu Ala Lys Gln Ile
85 90 95

Gln Ser Gln Trp Lys Glu Phe Gly Leu Asp Ser Val Glu Leu Ala His
100 105 110

Tyr Asp Val Leu Leu Ser Tyr Pro Asn Lys Thr His Pro Asn Tyr Ile
115 120 125

Ser Ile Ile Asn Glu Asp Gly Asn Glu Ile Phe Asn Thr Ser Leu Phe
130 135 140

Glu Pro Pro Pro Pro Gly Tyr Glu Asn Val Ser Asp Ile Val Pro Pro
145 150 155 160

Phe Ser Ala Phe Ser Pro Gln Gly Met Pro Glu Gly Asp Leu Val Tyr
165 170 175

Val Asn Tyr Ala Arg Thr Glu Asp Phe Phe Lys Leu Glu Arg Asp Met
180 185 190

Lys Ile Asn Cys Ser Gly Lys Ile Val Ile Ala Arg Tyr Gly Lys Val
195 200 205

Phe Arg Gly Asn Lys Val Lys Asn Ala Gln Leu Ala Gly Ala Lys Gly
210 215 220

Val Ile Leu Tyr Ser Asp Pro Ala Asp Tyr Phe Ala Pro Gly Val Lys
225 230 235 240

```
Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
    450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
    530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
    610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655
```

-continued

```
Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
        675                 680                 685

His Val Ile Tyr Ala Pro Ser Ser His Asn Lys Tyr Ala Gly Glu Ser
    690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750


<210> SEQ ID NO 145
<211> LENGTH: 88
<212> TYPE: PRT
<213> ORGANISM: Unknown
<220> FEATURE:
<223> OTHER INFORMATION: Description of Unknown:
      3rd FN3 domain of tenascin C polypeptide

<400> SEQUENCE: 145

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85


<210> SEQ ID NO 146
<211> LENGTH: 89
<212> TYPE: PRT
<213> ORGANISM: Unknown
<220> FEATURE:
<223> OTHER INFORMATION: Description of Unknown:
      Fibcon polypeptide

<400> SEQUENCE: 146

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85


<210> SEQ ID NO 147
<211> LENGTH: 94
```

<212> TYPE: PRT
<213> ORGANISM: Unknown
<220> FEATURE:
<223> OTHER INFORMATION: Description of Unknown:
10th FN3 domain of fibronectin polypeptide

<400> SEQUENCE: 147

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90
```

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 148

```
Gly Ser Gly Ser
1
```

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 149

```
Gly Gly Gly Ser Gly Gly Gly Ser
1               5
```

<210> SEQ ID NO 150
<211> LENGTH: 25
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 150

```
Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25
```

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 151

Ala Pro Ala Pro
1

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Ala Pro Ala Pro Ala Pro Ala Pro Ala Pro
1 5 10

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Ala Pro Ala Pro Ala Pro Ala Pro Ala Pro Ala Pro Ala Pro Ala Pro
1 5 10 15

Ala Pro Ala Pro
20

<210> SEQ ID NO 154
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Ala Pro Ala Pro Ala Pro Ala Pro Ala Pro Ala Pro Ala Pro Ala Pro
1 5 10 15

Ala Pro Ala Pro Ala Pro Ala Pro Ala Pro Ala Pro Ala Pro Ala Pro
20 25 30

Ala Pro Ala Pro Ala Pro Ala Pro
35 40

<210> SEQ ID NO 155
<211> LENGTH: 585
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

Asp Ala His Lys Ser Glu Val Ala His Arg Phe Lys Asp Leu Gly Glu
1 5 10 15

Glu Asn Phe Lys Ala Leu Val Leu Ile Ala Phe Ala Gln Tyr Leu Gln
20 25 30

Gln Ser Pro Phe Glu Asp His Val Lys Leu Val Asn Glu Val Thr Glu
35 40 45

Phe Ala Lys Thr Cys Val Ala Asp Glu Ser Ala Glu Asn Cys Asp Lys
50 55 60

-continued

```
Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480
```

-continued

```
Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585


<210> SEQ ID NO 156
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156

ctgccagccc cgaagaattt ggtcgtttcc cgtgtcactg aggactctgc acgtctgagc     60

tggaccgcac cggacgcggc gttcgacagc tttgcaatcg gctactggga gtgggatgat    120

gacggcgagg ccattgtgct gaccgttccg ggtagcgagc gcagctacga tctgaccggt    180

ctgaagccgg gtacggaata tccggtgtat attgcgggcg tgaagggtgg ccagtggagc    240

ttcccgctga gcgcgatctt taccacc                                        267


<210> SEQ ID NO 157
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157

ctgccggctc cgaaaaacct ggtcgtttcc cgtgtcactg aagattctgc acgcttgagc     60

tgggcgatcg acgagcagcg tgactggttt gagagcttcc tgattcagta tcaagaatcg    120

gaaaaagttg gcgaggccat cgtgctgacc gttccgggta gcgagcgcag ctatgatctg    180

acgggtctga agccaggcac cgagtatacg gtgagcattt acggtgtcta ccatgtgtac    240

cgtagcaatc cgctgagcgc gatcttcacc acc                                 273


<210> SEQ ID NO 158
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158

ctgccagccc cgaaaaactt agttgtctcc cgcgtgaccg aagattctgc tcgtctgagc     60

tggactgcac cggacgcggc gttcgacagc tttccgattg gctactggga gtgggatgat    120

gacggtgaag cgatcgtgct gaccgttccg ggtagcgagc gtagctatga cctgacgggt    180
```

-continued

```
ttgaaacctg gtaccgagta tcacgtttac attgcgggcg tcaagggtgg ccagtggtcg    240

ttcccgctga gcgcaatctt tacgacc                                        267


<210> SEQ ID NO 159
<211> LENGTH: 16
<212> TYPE: PRT
<213> ORGANISM: Unknown
<220> FEATURE:
<223> OTHER INFORMATION: Description of Unknown:
      PSMA epitope peptide

<400> SEQUENCE: 159

Lys Lys Ser Pro Ser Pro Glu Phe Ser Gly Met Pro Arg Ile Ser Lys
1               5                   10                  15


<210> SEQ ID NO 160
<211> LENGTH: 7
<212> TYPE: PRT
<213> ORGANISM: Unknown
<220> FEATURE:
<223> OTHER INFORMATION: Description of Unknown:
      PSMA epitope peptide

<400> SEQUENCE: 160

Asn Trp Glu Thr Asn Lys Phe
1               5
```

PROSTATE SPECIFIC MEMBRANE ANTIGEN BINDING FIBRONECTIN TYPE III DOMAINS

This application is a continuation of U.S. application Ser. No. 15/148,312, filed May 6, 2016, now U.S. Pat. No. 10,844,111, issued Nov. 24, 2020, which claims priority to and the benefit of U.S. Provisional Application No. 62/157,772, filed May 6, 2015, the entire contents of each are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "065768_10UD3_Sequence_Listing" and a creation date of Oct. 6, 2020, and having a size of 634 kb. The sequence listing submitted via EFS-Web is part of the specification and is herein incorporated by reference in its entirety.

FIELD OF THE INVENTION

The present invention relates to prostate specific membrane antigen binding molecules and methods of making and using the molecules.

BACKGROUND OF THE INVENTION

Prostate specific membrane antigen (PSMA), also known as glutamate carboxypeptidase II or N-acetylated alpha-linked acidic dipeptidase 1, is a dimeric type 2 transmembrane glycoprotein. PSMA cleaves several substrates, including folate and N-acetyl-L-aspartyl-L-glutamate, and is expressed in a number of tissues with highest expression in prostate, and to a lesser extent in the small intestine, central and peripheral nervous system, kidney and lung. PSMA is constitutively internalized through clathrin coated pits.

PSMA is a well-established prostate-cancer related cell membrane antigen frequently overexpressed in prostatic intraepithelial neoplasia (PIN), a condition in which some prostate cells have begun to look and behave abnormally, primary and metastatic prostate cancers and the neovasculature of other solid tumors, (e.g. breast, lung, bladder, kidney) (Chang et al., Clin Cancer Res 5: 2674-2681, 1999, Liu et al., Cancer Res 57: 3629-3634, 1997, Silver et al., Clin Cancer Res 3: 81-85, 1997; Bostwick et al., Cancer 82:2256-2261, 1998). PSMA expression correlates with disease progression and Gleason score. PSMA expression is increased in metastatic disease, hormone refractory cases, and higher-grade lesions, and it is further upregulated in androgen-insensitive tumors (Su et al., Cancer Res 55: 1441-1443, 1995, Kawakami et al., 57:2321-2324, 1997, Wright et al., Urology 48: 326-334, 1996).

Prostate cancer is the leading cause of cancer among males, and the 2$^{nd}$ leading cause of cancer-induced death. Globally, there are approximately 1,100,000 new cases and 300,000 mortalities every year, translating to about 4% of all cancer deaths. It is estimated that 1 in every 6 men will be diagnosed with the disease. In the U.S., more than 90% of prostate cancers are found in local or regional stages. At these early stages, the 5-year survival rate is close to 100%. When the cancer has metastasized, however, the 5-year survival rate is reduced to about 28%. Localized prostate cancer can often be controlled by hormone deprivation.

Current treatments for prostate cancer include surgery, radiation and hormone therapies. However, tumor cells often become androgen insensitive, and limited treatment options remain. Typically, the cancer vaccine sipuleucel-T, a radiopharmaceutical agent (such as radium-223 chloride), secondary hormone therapies (such as abiraterone or enzalutamide), and/or chemotherapies (docetaxel and cabazitaxel) are added to the hormonal therapy in sequence.

Monoclonal antibodies targeting PSMA have been evaluated in the clinic as both diagnostic imaging agents and antibody-drug conjugates. The most extensively evaluated antibody-drug conjugates (ADCs) targeting PSMA utilize the same humanized/de-immunized anti-PSMA mAb, J591. At least three different ADCs utilizing J591 have been evaluated in clinical trials, utilizing various linkers and warheads. Millenium Pharmaceuticals completed Phase 1 clinical trials evaluating MLN2704, an anti-PSMA mAb conjugated to a disulfide linked maytansine; Progenics utilized Seattle Genetics technology to link J591 to MMAE using a valine-citrulline linker, and ADCT is initiating clinical trials for a PBD-conjugated to J591. To date, limited clinical efficacy has been coupled with serious toxicities and short serum half-lives, likely due to significant liver uptake (Morris et al., Clin Cancer Res 13: 2707-2713, 2007). Nonetheless, in two separate clinical studies, there was evidence of decreased PSA/CTC levels following repeat treatment with anti-PSMA ADCs, particularly at the higher doses (D Petrylak, Genitourinary Cancers Symposium, 2014, Galsky et al., J Clin Oncol 26: 2147-2154, 2008, D Petrylak, ASCO 2014). In the case of Progenics, two dose-limiting toxicities resulted in death following sepsis due to neutropenia (D Petrylak, ASCO 2014).

While each of these treatments can delay growth of the cancer for several months and palliate symptoms produced by the disease, the disease ultimately becomes resistant to them.

Therefore, there is a need for additional and improved therapeutics to treat prostate cancer and other cancers over-expressing PSMA.

SUMMARY OF THE INVENTION

One embodiment of the invention is an isolated FN3 domain that specifically binds human prostate specific membrane antigen (PSMA) of SEQ ID NO: 144.

Another embodiment of the invention is an isolated FN3 domain that specifically binds human PSMA of SEQ ID NO: 144, wherein the FN3 domain cross-reacts with *Macaca fascicularis* PSMA of SEQ ID NO: 32 or with Pan troglodytes PSMA of SEQ ID NO: 33.

Another embodiment of the invention is an isolated FN3 domain that specifically binds human PSMA of SEQ ID NO: 144, wherein the FN3 domain comprises an amino acid sequence that is 89% identical to the amino acid sequence of SEQ ID NO: 41, or that has 1, 2, 3, 4, 5, 6, 7, 8, 9, 10 or 11 substitutions when compared to the amino acid sequence of SEQ ID NO: 41.

Another embodiment of the invention is an isolated FN3 domain that specifically binds human PSMA of SEQ ID NO: 144, wherein the FN3 domain comprises the amino acid sequence of SEQ ID NOs: 35, 36, 37, 38, 39, 40, 41, 42, 43, 44, 45, 46, 47, 48, 49, 50, 51, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140.

One embodiment of the invention is an isolated FN3 domain that specifically binds human prostate specific membrane antigen (PSMA) of SEQ ID NO: 144 conjugated to a cytotoxic agent or a detectable label.

Another embodiment of the invention is an isolated polynucleotide encoding the FN3 domain of the invention.

Another embodiment of the invention is a vector comprising the polynucleotide of the invention.

Another embodiment of the invention is a host cell comprising the vector of the invention.

Another embodiment of the invention is a method of producing the FN3 domain of the invention, comprising culturing the isolated host cell of the invention under conditions such that the FN3 domain of the invention is expressed, and purifying the FN3 domain.

Another embodiment of the invention is a pharmaceutical composition comprising the FN3 domain of the invention and a pharmaceutically acceptable carrier.

Another embodiment of the invention is a method of treating a subject having cancer characterized by overexpression of PSMA, comprising administering a therapeutically effective amount of the FN3 domain of the invention conjugated to a cytotoxic agent to a patient in need thereof for a time sufficient to treat the cancer.

Another embodiment of the invention is a diagnostic kit comprising the FN3 domain of the invention. Another embodiment of the invention is a cancer diagnostic or capture agent comprising the FN3 domain of the invention.

Another embodiment of the invention is a method of detecting PSMA-expressing cells in a biological sample comprising treating the biological sample with a diagnostic agent comprising the FN3 domain of the invention and evaluating the binding of the biological sample to such diagnostic agent comprising the FN3 domain of the invention.

Another embodiment of the invention is a method of isolating PSMA expressing cells in a biological sample comprising treating the biological sample with a capture agent comprising the FN3 domain of the invention and isolating the portion of the biological sample which binds to such capture agent comprising the FN3 domain.

Another embodiment of the invention is a method of detecting PSMA-expressing tumor cells in a subject, comprising administering to the subject the FN3 domain of the invention, and detecting binding of the FN3 domain to PSMA-expressing tumor cells in the subject.

Another embodiment of the invention is a method of delivering a therapeutic molecule to PSMA-expressing tumor cells, comprising administering the FN3 domain of the invention to a subject having PSMA-expressing tumor.

BRIEF DESCRIPTION OF THE DRAWINGS

FIG. 4A shows the amino acid sequence alignment between human (h) and cynomolgous (c) PSMA extracellular domains. The H10 contact residues are underlined and in bold. The residues that differ between human and cynomolgus PSMA are shaded. All cyno PSMA residues interacting with H10 are conserved in human PSMA except for N613. Human PSMA ECD; SEQ ID NO: 143. Cyno PSMA ECD: SEQ ID NO: 32

FIG. 4B shows the H10 FN3 domain residues in contact with cynomolgous PSMA. The contact residues are underlined and in bold. H10 amino acid sequence is shown in SEQ ID NO: 41.

DETAILED DESCRIPTION OF THE INVENTION

Figure 1:
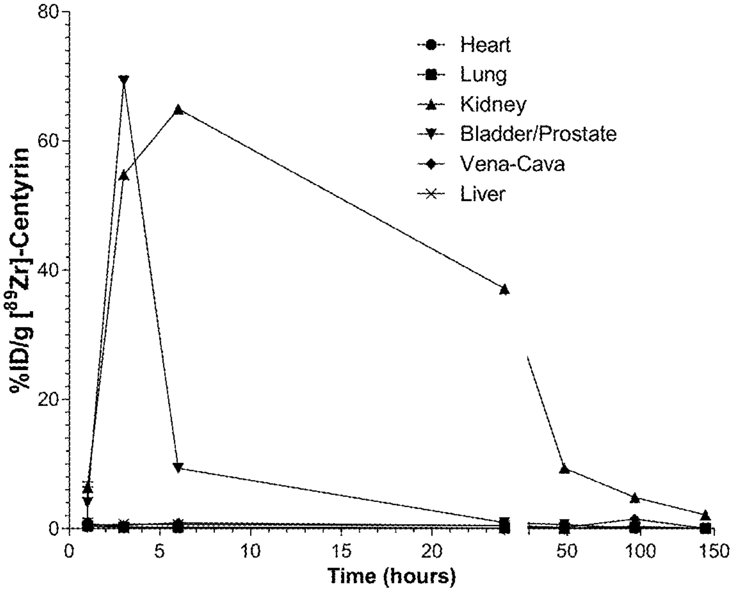
FIG. 1 shows biodistribution of untargeted $^{89}$Zr-labeled Centyrin following intravenous injection in male NSG mice.

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the 3$^{rd}$ FN3 domain of tenascin (TN3), or the 10$^{th}$ FN3 domain of fibronectin (FN10).

"Centyrin" as used herein refers to a FN3 domain that is based on the consensus sequence of the 15 different FN3 domains present in human tenascin C.

The term "capture agent" refers to substances that bind to a particular type of cells and enable the isolation of that cell from other cells. Examples of capture agents include but are not limited to magnetic beads, ferrofluids, encapsulating reagents and the like.

The term "biological sample" refers to blood, tissue, marrow, sputum and the like.

The term "diagnostic reagent" refers to any substance that may be used to analyze a biological sample, whether or not such substance is distributed as a single substance or in a combination with other substances in a diagnostic kit.

The term "substituting" or "substituted" or "mutating" or "mutated" as used herein refers to altering, deleting of inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a predetermined antigen with a dissociation constant ($K_D$) of about $1\times10^{-6}$ M or less, for example about $1\times10^{-7}$ M or less, about $1\times10^{-8}$M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Typically the FN3 domain of the invention binds to a predetermined antigen (i.e. human PSMA) with a $K_D$ that is at least ten fold less than its $K_D$ for a nonspecific antigen (for example BSA or casein) as measured by surface plasmon resonance using for example a Proteon Instrument (BioRad). The isolated FN3 domain of the invention that specifically binds to human PSMA may, however, have cross-reactivity to other related antigens, for example to the same predetermined antigen from other species (homologs), such as *Macaca fascicularis* (cynomolgous monkey, cyno) or Pan troglodytes (chimpanzee).

The term "epitope" as used herein means a portion of an antigen to which an FN3 domain of the invention specifically binds. Epitopes usually consist of chemically active (such as polar, non-polar or hydrophobic) surface groupings of moieties such as amino acids or polysaccharide side chains and can have specific three-dimensional structural characteristics, as well as specific charge characteristics. An epitope can be composed of contiguous and/or discontiguous amino acids that form a conformational spatial unit. For a discontiguous epitope, amino acids from differing portions of the linear sequence of the antigen come in close proximity in 3-dimensional space through the folding of the protein molecule.

The term "library" refers to a collection of variants. The library may be composed of polypeptide or polynucleotide variants.

The term "stability" as used herein refers to the ability of a molecule to maintain a folded state under physiological conditions such that it retains at least one of its normal functional activities, for example, binding to a predetermined antigen such as human PSMA.

Human PSMA as used herein refers to the well known type II glycoprotein of about 100 kD with a short intracellular domain (residues 1-18), a transmembrane domain (residues 19-43) and an extracellular domain (reisudes 44-750). The amino acid sequence of the mature human PSMA is shown in SEQ ID NO: 144.

"Overexpress", "overexpressed" and "overexpressing" as used herein interchangeably refer to a cancer or malignant cell that has measurably higher levels of PSMA on the surface compared to a normal cell of the same tissue type. Such overexpression may be caused by gene amplification or by increased transcription or translation. PSMA overexpression can be measured using well know assays using for example ELISA, immunofluorescence, flow cytometry or radioimmunoassay on live or lysed cells. Alternatively, or additionally, levels of PSMA nucleic acid molecules may be measured in the cell for example using fluorescent in situ hybridization, Southern blotting, or PCR techniques. PSMA is overexpressed when the level of PSMA on the surface of the cell is at least 1.5-fold higher when compared to the normal cell.

"Tencon" as used herein refers to the synthetic fibronectin type III (FN3) domain having the sequence shown in SEQ ID NO: 1 and described in U.S. Pat. Publ. No. US2010/0216708.

A "cancer cell" or a "tumor cell" as used herein refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Inhibits growth" (e.g. referring to cells, such as tumor cells) refers to a measurable decrease in the cell growth in vitro or in vivo when contacted with a therapeutic or a combination of therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100%. Inhibition of cell growth may occur by a variety of mechanisms, for example by apoptosis, necrosis, or by inhibition of cell proliferation, or lysis of cells.

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "polypeptide" or "protein" means a molecule that comprises at least two amino acid residues linked by a peptide bond to form a polypeptide. Small polypeptides of less than about 50 amino acids may be referred to as "peptides".

"Valent" as used herein refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

The term "in combination with" as used herein means that two or more therapeutics can be administered to a subject together in a mixture, concurrently as single agents or sequentially as single agents in any order.

"Synergy", "synergism" or "synergistic" mean more than the expected additive effect of a combination.

Compositions of Matter

The present invention provides human PSMA binding FN3 domains and PSMA binding FN3 domains conjugated to toxins or detectable labels. The present invention provides polynucleotides encoding the FN3 domains of the invention or complementary nucleic acids thereof, vectors, host cells, and methods of making and using them.

PSMA Binding Molecules

The present invention provides fibronectin type III (FN3) domains that bind specifically to human prostate specific membrane antigen (PSMA), optionally conjugated to a toxin or a detectable label. These molecules may be widely used in therapeutic and diagnostic applications. The present invention provides polynucleotides encoding the FN3 domains of the invention or complementary nucleic acids thereof, vectors, host cells, and methods of making and using them.

The FN3 domains of the invention bind PSMA with high affinity and are internalized into PSMA expressing cells, thereby providing an efficient way to deliver therapeutic drugs into tumor cells.

One embodiment of the invention an isolated FN3 domain that specifically binds human prostate specific membrane antigen (PSMA) of SEQ ID NO: 144.

In some embodiment of the invention described herein, the FN3 domain of the invention cross-reacts with *Macaca fascicularis* PSMA of SEQ ID NO: 32 or with Pan troglodytes PSMA of SEQ ID NO: 33.

The FN3 domain of the invention may bind human, *Macaca fascicularis* and/or Pan troglodytes PSMA with a dissociation constant ($K_D$) of less than about $1\times10^{-7}$ M, for example less than about $1\times10^{-8}$ M, less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffer described herein.

In some embodiments, the PSMA binding FN3 domains comprises an initiator methionine (Met) linked to the N-terminus of the molecule.

In some embodiments, the PSMA binding FN3 domains comprise a cysteine (Cys) linked to a C-terminus of the FN3 domain.

The addition of the N-terminal Met and/or the C-terminal Cys may facilitate expression and/or conjugation of half-life extending molecules.

Another embodiment of the invention is an isolated isolated FN3 domain that specifically binds human PSMA, wherein the FN3 domain inhibits human PSMA enzymatic activity. PSMA enzymatic activity may be measured using standard methods. For example, hydrolysis of a detectable or labeled PSMA substrate of PSMA may be used. Exemplary PSMA substrates that may be used are N-Acetyl Aspartyl Glutamate (NAAG), folate polyglutamate, methotrexate tri-gamma glutamate, methotrexate di-gamma glutamate, pteroylpentaglutamate and derivatives thereof. The substrate may be labeled, for example, with a radioactive marker, chemiluminescent marker, enzymatic marker, chromogenic marker, or other detectable marker. Suitable methods for detecting PSMA activity are described, for example, in U.S. Pat. No. 5,981,209 or U.S. Pat. Publ. No. 2006/0009525. The isolated PSMA binding FN3 domain of the invention inhibits human PSMA enzymatic activity when the molecule inhibits human PSMA activity more than about 20%, 30%, 40%, 50%, 60%, 70%, 80%, 90%, or more when compared to a sample without the FN3 domain.

In some embodiments of the invention described herein, the isolated FN3 domain comprises the amino acid sequence of SEQ ID NOs: 35, 36, 37, 38, 39, 40, 41, 42, 43, 44, 45, 46, 47, 48, 49, 50, 51, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140.

In some embodiments of the invention described herein, the isolated FN3 domain comprises an amino acid sequence that is 89% identical to the amino acid sequence of SEQ ID NO: 41.

In some embodiments of the invention described herein, the isolated FN3 domain comprises an amino acid sequence that has 1, 2, 3, 4, 5, 6, 7, 8, 9, 10 or 11 substitutions when compared to the amino acid sequence of SEQ ID NO: 41.

In some embodiments of the invention described herein, the isolated FN3 domain that specifically binds human PSMA comprises a cysteine residue in at least one residue position corresponding to residue positions 6, 11, 22, 25, 26, 52, 53, 61 of SEQ ID NO 1, or at a C-terminus.

Substitutions resulting in introduction of cysteine into a protein sequence may be utilized to chemically conjugate small molecules such as cytotoxic agents, detectable labels, polyethylene glycol and/or nucleic acids to the FN3 domain using standard chemistry.

In some embodiments, the FN3 domain specifically binding human PSMA competes for binding to human PSMA with the FN3 domain of SEQ ID NO: 41.

In some embodiments, the FN3 domain specifically binding human PSMA binds to the region KKSPSPEFSGMPRISK (SEQ ID NO: 159) and NWETNKF (SEQ ID NO: 160) of human PSMA.

The human PSMA epitope bound by the FN3 domain of the invention includes some or all of the residues within the amin oasequences shown in SEQ ID NO: 159 or SEQ ID NO: 160. In some embodiments disclosed herein, the epitope bound by the FN3 domain of the invention comprises at least one amino acid in the region KKSPSPEFSGMPRISK (SEQ ID NO: 159) and NWETNKF (SEQ ID NO: 160) of human PSMA (SEQ ID NO: 144). In some embodiments disclosed herein, the epitope bound by the FN3 domain of the invention comprises at least two, three, four, five, six or seven amino acids in the region KKSPSPEFSGMPRISK (SEQ ID NO: 159) and at least two, three, four, five or six amino acids in the region NWETNKF (SEQ ID NO: 160) of human PSMA (SEQ ID NO: 144).

In some embodiments disclosed herein, the FN3 domain of the invention binds human PSMA at residues K499, K500, S501, P502, P504, R511, K514, N540, W541, E542, N544, K545 and F546 (residue numbering according to SEQ ID NO: 144).

In some embodiments disclosed herein, the FN3 domain of the invention further binds human PSMA at residues R181, Y460, F488, K610 and/or 1614.

The crystal structure of the FN3 domain P233FR9_H10 was solved in complex with cynoPSMA. As the contact residues between human and cyno PSMA are identical except for one residue, it is expected that P233FR9_H10 will bind human PSMA at the same epitope residues than what it binds cyno PSMA.

FN3 domains may be evaluated for ther competition with a reference molecule for binding human PSMA using well known in vitro methods. In an exemplary method, CHO cells recombinantly expressing human PSMA may be incubated with unlabeled reference molecule for 15 min at 4° C., followed by incubation with an excess of fluorescently labeled test FN3 domain for 45 min at 4° C. After washing in PBS/BSA, fluorescence may be measured by flow cytometry using standard methods. In another exemplary method, extracellular portion of human PSMA may be coated on the surface of an ELISA plate. Excess of unlabelled reference molecule may be added for about 15 minutes and subsequently biotinylated test FN3 domains may be added. After washes in PBS/Tween, binding of the test biotinylated FN3 domain may be detected using horseradish peroxidase (HRP)-conjugated streptavidine and the signal detected using standard methods. It is readily apparent that in the competition assays, reference molecule may be labelled and the test FN3 domain unlabeled. The test FN3 domain competes with the reference molecule when the reference molecule inhibits binding of the test FN3 domain, or the test FN3 domain inhibits binding of the reference molecule by 20%, 30%, 40%, 50%, 60%, 70%, 80%, 85%, 90%, 95% or 100%. The epitope of the test FN3 domain may further be defined for example by peptide mapping or hydrogen/deuterium protection assays using known methods, or by crystal structure determination. An exemplary reference FN3 domain is the domain comprising the amino acid sequence of SEQ ID NO: 41.

FN3 domains binding to the same region on human PSMA as the FN3 domain of SEQ ID NO: 41 may be generated for example by immunizing mice with peptides having the amino acid sequences shown in SEQ ID NOs: 159 and 160 using standard methods and as described herein. FN3 domains may be further evaluated for example by assaying competition between the FN3 domain of SEQ ID NO: 41 and a test FN3 domain for binding to human PSMA using well known in vitro methods and as described above.

In some embodiments, the isolated FN3 domain that specifically binds human PSMA of the invention is conjugated to a detectable label.

Detectable label includes compositions that when conjugated to the FN3 domain of the invention renders the latter detectable, via spectroscopic, photochemical, biochemical, immunochemical, or chemical means. Exemplary labels include radioactive isotopes, magnetic beads, metallic beads, colloidal particles, fluorescent dyes, electron-dense reagents, enzymes (for example, as commonly used in an ELISA), biotin, digoxigenin, or haptens. Specific radioactive labels include most common commercially available isotopes including, for example, $^{3}$H, $^{8}$C, $^{13}$C, $^{15}$N, $^{18}$F, $^{19}$F, $^{123}$I, $^{124}$I, $^{125}$I, $^{131}$I, $^{86}$Y, $^{89}$Zr, $^{U1}$In, $^{94m}$Tc $^{99m}$Tc, $^{64}$Cu and $^{68}$Ga. Suitable dyes include any commercially available dyes such as, for example, 5(6)-carboxyfluorescein, IRDye 680RD maleimide or IRDye 800CW, ruthenium polypyridyl dyes, and the like.

The FN3 domains that specifically binds human PSMA conjugated to a detectable label may be used as an imaging agent to evaluate tumor distribution, diagnosis for the presence of tumor cells and/or recurrence of tumor.

In some embodiments, the FN3 domains specifically binding human PSMA of the invention is conjugated to a cytotoxic agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains specifically binding human PSMA conjugated to a cytotoxic agent may be used in the targeted delivery of the cytotoxic agent to PSMA expressing tumor cell, and intracellular accumulation therein, wherein systemic administration of these unconjugated cytotoxic agents may result in unacceptable levels of toxicity to normal cells.

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elict their cytotoxic and cytostatic effects by mechanisms including tubulin binding, DNA binding, or topoisomerase inhibition.

In some embodiments, the cytotoxic agent is an enzymatically active toxins such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}{}_{Bi}$, $^{131}$I, $^{131}$In, $^{90}$Y, and $^{186}$Rc.

Conjugates of the FN3 domains of the invention and the cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, the cytotoxic agent is dolastatins or dolostatin peptidic analogs and derivatives, auristatin or monomethyl auristatin phenylalanine Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the FN3 domain containing molecule of the invention through the N (amino) terminus or the C (carboxyl) terminus of the peptidic drug moiety (WO 02/088172), or via any cysteine engineered into the FN3 domain.

In some embodiment, the FN3 domain specifically binding human PSMA is removed from the blood via renal clearance.

Isolation of PSMA Binding FN3 Domains From a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind PSMA. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is is described in U.S. Pat. Publ. No. US2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

TABLE 1

| FN3 domain | Tencon (SEQ ID NO: 1) |
|---|---|
| A strand | 1-12 |
| AB loop | 13-16 |

TABLE 1-continued

| FN3 domain | Tencon (SEQ ID NO: 1) |
|---|---|
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well known IUB code.

The FN3 domains specifically binding human PSMA of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to PSMA by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains specifically binding PSMA are further characterized for their inhibition of PSMA activity, internalization, stability, and other desired characteristics.

The FN3 domains specifically binding human PSMA of the invention may be generated using any FN3 domain as a template to generate a library and screening the library for molecules specifically binding human PSMA using methods provided within. Exemplar FN3 domains that may be used are the 3rd FN3 domain of tenascin C (TN3) (SEQ ID NO: 145), Fibcon (SEQ ID NO: 146), and the $10^{th}$ FN3 domain of fibronectin (FN10) (SEQ ID NO: 147). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472,147).

In some embodiments of the invention described herein, the FN3 domain specifically binding human PSMA is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

The FN3 domains specifically binding human PSMA of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domain specifically binding human PSMA of the invention may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phosopholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain of the invention may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 148), $(GGGS)_2$ (SEQ ID NO: 149), $(GGGGS)_5$ (SEQ ID NO: 150), $(AP)_2$ (SEQ ID NO: 151), $(AP)_5$ (SEQ ID NO: 152), $(AP)_{10}$ (SEQ ID NO: 153), $(AP)_{20}$ (SEQ ID NO: 154) and $A(EAAAK)_5AAA$ (SEQ ID NO: 142). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Half-Life Extending Moieties

The FN3 domain specifically binding human PSMA of the invention may incorporate other subunits for example via covalent interaction. In one aspect of the invention, the FN3 domain of the invention further comprises a half-life extending moiety. Exemplary half-life extending moieties are albumin, albumin variants, albumin-binding proteins and/or domains, transferrin and fragments and analogues thereof, and Fc regions. An exemplary albumin variant is shown in SEQ ID NO: 155. Amino acid sequences of the human Fc regions are well known, and include IgG1, IgG2, IgG3, IgG4, IgM, IgA and IgE Fc regions.

All or a portion of an antibody constant region may be attached to the FN3 domain of the invention to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, *Curr Opin Biotechnol.* 20, 685-691, 2009).

Additional moieties may be incorporated into the FN3 domain of the invention such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the FN3 domain of the invention by incorporating a cysteine residue to the C-terminus of the molecule, or engineering cysteines into residue positions that face away from the human PSMA binding face of the molecule, and attaching a pegyl group to the cysteine using well known methods.

FN3 domain of the invention incorporating additional moieties may be compared for functionality by several well known assays. For example, altered properties due to incorporation of Fc domains and/or Fc domain variants may be assayed in Fc receptor binding assays using soluble forms of the receptors, such as the FcγR1, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention provides for nucleic acids encoding the FN3 domains specifically binding human PSMA of the invention as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains of the invention are also within the scope of the invention.

One embodiment of the invention is an isolated polynucleotide encoding the FN3 domain specifically binding human PSMA comprising the amino acid sequence of SEQ ID NOs: 35, 36, 37, 38, 39, 40, 41, 42, 43, 44, 45, 46, 47, 48, 49, 50, 51, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140.

One embodiment of the invention is an isolated polynucleotide comprising the polynucleotide sequence of SEQ ID NOs: 156, 157, 158 or 159.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the invention is a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

Another embodiment of the invention is a host cell comprising the vector of the invention. The FN3 domain specifically binding human PSMA of the invention may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, NY (1989); Colligan, et al., eds., Current Protocols in Immunology, John Wiley & Sons, Inc., N.Y. (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

Another embodiment of the invention is a method of producing the isolated FN3 domain specifically binding human PSMA of the invention, comprising culturing the isolated host cell of the invention under conditions such that the isolated FN3 domain specifically binding human PSMA is expressed, and purifying the FN3 domain.

The FN3 domain specifically binding human PSMA may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Uses of Human PSMA Binding FN3 Domains of the Invention

The FN3 domains specifically binding human PSMA of the invention may be used to diagnose, monitor, modulate, treat, alleviate, help prevent the incidence of, or reduce the symptoms of human disease or specific pathologies in cells, tissues, organs, fluid, or, generally, a host. The methods of the invention may be used to treat an animal patient belonging to any classification. Examples of such animals include mammals such as humans, rodents, dogs, cats and farm animals.

One embodiment of the invention is a method of treating a subject having cancer characterized by overexpression of PSMA, comprising administering to the subject a FN3 domain specifically binding human PSMA of the invention conjugated to a cytotoxic agent for a time sufficient to treat the subject.

In some embodiments, the cancer is prostate cancer, colorectal cancer, gastric cancer, clear cell renal carcinoma, bladder cancer, lung cancer or kidney cancer.

In some embodiments, the cancer is solid tumor.

In some embodiments, the cancer is a prostate disorder such as, for example, prostate cancer or benign prostatic hyperplasia (BPH).

In some embodiments, the cancer is prostate cancer.

In some embodiments, the cancer is colorectal cancer.

In some embodiments, the cancer is gastric cancer.

In some embodiments, the cancer is clear cell renal carcinoma.

In some embodiments, the cancer is bladder cancer.

In some embodiments, the cancer is kidney cancer.

In some embodiments, the cancer is a neovascular disorder such as, for example, a cancer characterized by solid tumor growth. Exemplary cancers with tumor vasculatures characterized by PSMA overexpression and amenable to treatment in accordance with the present invention include, for example, clear cell renal carcinoma (CCRCC), colorectal cancer, breast cancer, bladder cancer, lung cancer, and pancreatic cancer (see, e.g., Baccala et al., *Urology* 70:385.390, 2007 (expression of PSMA in CCRCC); Liu et al., *Cancer Res.* 57:3629-3634, 1997 (expression of PSMA in various non-prostate cancers, including renal, urothelial, lung, colon, breast, and adenocarcinaoma to the liver); and Milowsky et al., *J. Clin. Oncol.* 25:540-547, 2007.

One embodiment of the invention is a method of treating a subject having prostate cancer characterized by overexpression of PSMA, comprising administering to the subject the FN3 domain specifically binding human PSMA of the invention conjugated of a cytotoxic agent for a time sufficient to treat the subject.

Subjects for administration of the FN3 domain specifically binding human PSMA of the invention as described herein include patients at high risk for developing a particular disorder characterized by PSMA overexpression as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder).

In prophylactic applications, pharmaceutical compositions or medicants are administered to a patient susceptible to, or otherwise at risk of, a particular disorder in an amount sufficient to eliminate or reduce the risk or delay the onset of the disorder. In therapeutic applications, compositions or medicants are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

To identify subject patients for treatment according to the methods of the invention, accepted screening methods may be employed to determine risk factors associated with specific disorders or to determine the status of an existing disorder identified in a subject. Such methods can include, for example, determining whether an individual has relatives who have been diagnosed with a particular disorder. Screening methods may also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, PSMA-expressing cells can be implemented as an independent treatment program or as a follow-up, adjunct, or coordinate treatment regimen to other treatments.

In some methods described herein, the FN3 domains specifically binding human PSMA of the invention conjugated to a cytotoxic agent may be used to treat a subject with prostate cancer in combination with a second therapeutic.

In some methods described herein, the FN3 domains specifically binding human PSMA of the invention conjugated to a cytotoxic agent may be used to treat a subject who is resistant or has acquired resistance to a treatment with a second therapeutic.

The second therapeutic may be an approved drug for the treatment of prostate cancer, such as Abiraterone Acetate (Zytiga), Bicalutamide, Cabazitaxel, Casodex (Bicalutamide), Degarelix, Docetaxel, Enzalutamide, Goserelin Acetate, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Mitoxantrone Hydrochloride, Prednisone, Provenge (Sipuleucel-T), Radium 223 Dichloride, Sipuleucel-T, Taxotere (Docetaxel), Viadur (Leuprolide Acetate), Xofigo (Radium 223 Dichloride), Xtandi (Enzalutamide) or Zoladex (Goserelin Acetate) (source: National Cancer Institute).

Various qualitative and/or quantitative methods may be used to determine if a subject is resistant, has developed or is susceptible to developing a resistance to treatment. Symptoms that may be associated with resistance include, for example, a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to treatment, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with prostate cancer may include trouble passing or frequent urge to pass urine, painful urination, blood in the urine or sement, nagging pain in the pelvis, back and/or hips. Symptoms associated with lung cancer may include persistent cough, coughing up blood, shortness of breath, wheezing chest pain, loss of appetite, losing weight without trying and fatigue. One skilled in oncology may readily identify symptoms associated with a particular cancer type.

The terms "treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the PSMA binding FN3 domain of the invention may vary according to factors such as the disease state, age, sex, and weight of the individual, and the ability of the PSMA binding FN3 domain of the invention to elicit a desired response in the individual. Exemplary indicators of an effective PSMA binding FN3 domain that may decline or abate in association with resistance include, for example, improved well-being of the patient, decrease or shrinkage of the size of a tumor, arrested or slowed growth of a tumor, and/or absence of metastasis of cancer cells to other locations in the body.

Administration/Pharmaceutical Compositions

The invention provides for pharmaceutical compositions of the FN3 domains specifically binding human PSMA, optionally conjugated to a second molecule of the invention and a pharmaceutically acceptable carrier. For therapeutic use, the FN3 domains of the invention may be prepared as pharmaceutical compositions containing an effective amount of the domain or molecule as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, $21^{st}$ Edition, Troy, D. B. ed., Lipincott Williams and Wilkins, Philadelphia, PA 2006, Part 5, Pharmaceutical Manufacturing pp 691-1092, See especially pp. 958-989.

The mode of administration for therapeutic use of the FN3 domains of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of the FN3 domain of the invention.

The FN3 domains of the invention may be administered to a patient by any suitable route, for example parentally by intravenous (IV) infusion or bolus injection, intramuscularly or subcutaneously or intraperitoneally. IV infusion can be given over as little as 15 minutes, but more often for 30 minutes, 60 minutes, 90 minutes or even 2 or 3 hours. The PSMA binding FN3 domains of the invention may also be injected directly into the site of disease (e.g., the tumor itself). The dose given to a patient having a cancer is sufficient to alleviate or at least partially arrest the disease being treated ("therapeutically effective amount") and may be sometimes 0.1 to 10 mg/kg body weight, for example 1, 2, 3, 4, 5, 6, 7, 8, 9 or 10 mg/kg, but may even higher, for example 15, 20, 30, 40, 50, 60, 70, 80, 90 or 100 mg/kg. A fixed unit dose may also be given, for example, 50, 100, 200, 500 or 1000 mg, or the dose may be based on the patient's surface area, e.g., 400, 300, 250, 200, or 100 $mg/m^2$. Usually between 1 and 8 doses, (e.g., 1, 2, 3, 4, 5, 6, 7 or 8) may be administered to treat cancer, but 10, 12, 20 or more doses may be given. Administration of the FN3 domains of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

For example, a pharmaceutical composition of the FN3 domains of the invention for intravenous infusion may be made up to contain about 200 ml of sterile Ringer's solution, and about 8 mg to about 2400 mg, about 400 mg to about 1600 mg, or about 400 mg to about 800 mg of the PSMA binding FN3 domains for administration to a 80 kg patient. Methods for preparing parenterally administrable compositions are well known and are described in more detail in, for example, "Remington's Pharmaceutical Science", 15th ed., Mack Publishing Company, Easton, PA.

The FN3 domains of the invention may be lyophilized for storage and reconstituted in a suitable carrier prior to use. This technique has been shown to be effective with conventional protein preparations and art-known lyophilization and reconstitution techniques can be employed.

The FN3 domains of the invention may be administered to a subject in a single dose or the administration may be repeated, e.g. after one day, two days, three days, five days, six days, one week, two weeks, three weeks, one month, five weeks, six weeks, seven weeks, two months or three months. The repeated administration can be at the same dose or at a different dose. The administration can be repeated once, twice, three times, four times, five times, six times, seven times, eight times, nine times, ten times, or more.

The FN3 domains of the invention may be administered in combination with a second therapeutic agent simultaneously, sequentially or separately.

The FN3 domain of the invention, optionally in combination with the second therapeutic agent may be administered together with any form of radiation therapy including external beam radiation, intensity modulated radiation therapy (IMRT) and any form of radiosurgery including Gamma Knife® (gamma ray-based radiosurgery), CyberKnife® (X-ray or photon based radiosurgery), Linac, and interstitial radiation (e.g. implanted radioactive seeds, GliaSite™ balloon (intracavity inflatable balloon catheter)), and/or with surgery.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as 20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measurable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.) Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, Md.)

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

While having described the invention in general terms, the embodiments of the invention will be further disclosed in the following examples that should not be construed as limiting the scope of the claims.

Reagents and Constructs:

The extracellular domains of cynomolgus (cyno monkey protein database ref #EHH56646.1, SEQ ID NO: 32) and chimpanzee (UniProt™ protein sequence database) Ref #H2Q3K5, SEQ ID NO: 33) PSMA were cloned into the pUnder expression vector along with a 6His and Avi tag. Proteins were transiently expressed in 293HEK-expi cells. Supernatants were harvested and clarified by centrifugation. The proteins were purified using a two-step purification process: 1) IMAC purification with a HisTrap® HP column (His-tag chromatography column) and 2) size exclusion purification (Superdex® 200, size exclusion chromatography resin) where the elution buffer is DPBS containing $Mg^{2+}$, $Ca^{2+}$, and 0.5 mM $ZnCl_2$ to stabilize PSMA dimerization. Fractions containing the protein of interest were pooled and protein concentration was determined by A280.

The gene encoding *S. aureus* sortase A was produced by DNA2.0® and subcloned into pJexpress401 vector (DNA2.0®) for expression under the T5 promoter. The sortase construct for soluble expression is lacking the N-terminal domain of the natural protein consisting of 25 amino acids since this domain is membrane associated (Ton-That et al., Proc Natl Acad Sci USA 96: 12424-12429, 1999). The sortase was expressed as N-terminal His6-tag (HHHHHH, SEQ ID) NO: 34) followed by a TEV protease site for tag removal (ENLYFQS, SEQ ID NO: 54), resulting in the sortase having the amino acid sequence of SEQ ID NO: 52. The sortase protein used also includes 5 mutations sequence that are reported to increase the catalytic efficiency of the enzyme when compared to the wild type proteins (SEQ ID NO: 53) (Chen et al., Proc Natl Acad Sci USA 108: 11399-11404, 2011). The plasmid was transformed into *E. coli* BL21 Gold cells (Agilent®) for expression. A single colony was picked and grown in Luria Broth bacterial growth medium (Teknova®) supplemented with kanamycin and incubated 18 h at 37° C. 250 RPM. 250 mL of Terrific Broth bacterial growth medium (Teknova®), supplemented with kanamycin, was inoculated from these subcultures and grown at 37° C. for ~4 h while shaking. Protein expression was induced with 1 mM IPTG, and the protein was expressed for 18 h at 30° C. Cells were harvested by centrifugation at 6000 g and stored at −20° C. until purification. The frozen cell pellet was thawed for 30 min at room temperature and suspended in BugBuster® HT protein extraction reagent (EMD Millipore®) supplemented with 1 uL per 30 mL of recombinant lysozyme (EMD Millipore®) at 5 mL per gram of cell paste and incubated for 30 minutes on a shaker at room temperature. The lysate was clarified by centrifugation at 74 600 g for 30 min.

The supernatant was applied onto a gravity column packed with 3 mL of Qiagen® Superflow Ni-NTA nickle-charged resin pre-equilibrated with buffer A (50 mM sodium phosphate buffer, pH 7.0 containing 0.5 M NaCl and 10 mM imidazole). After loading, the column was washed with 100 mL of Buffer A. The protein was eluted with Buffer A supplemented with 250 mM imidazole and loaded on a preparative gel-filtration column, TSKgel® G3000SW (liquid chromatography column) 21.5×600 mm (Tosoh®) equilibrated in PBS (Gibco®). The gel-filtration chromatography was performed at room temperature in PBS at flow rate 10 mL/min using an AKTA-AVANT chromatography system. Purified sortase was then digested with TEV protease to remove the His6 tag. 28 mg of sortase was incubated in 10 mL with 3000 units of AcTEV™ protease (Invitrogen®) in the supplied buffer supplemented with 1 mM DTT for 2 hours at 30° C. The tag-less sortase was purified with Ni-NTA resin. The reaction was exchanged into TBS buffer (50 mM Tris pH 7.5, 150 mM NaCl) using PD-10 columns (desalting column; GE Healthcare®) and applied onto a gravity column packed with 0.5 mL of Qiagen® Superflow Ni-NTA nickle-charged resin pre-equilibrated with buffer A. The flowthrough was collected and the resin was washed with 3 mL of buffer A which was added to the flowthrough. This flowthrough was concentrated to ~0.5 mL in an Amicon® 15 concentrator with 10 kDa cutoff (EMD) Millipore®). Additional TBS buffer was added and the sample was concentrated again (repeated twice) to exchange the buffer to TBS. ⅓rd volume of 40% glycerol was added (final concentration of 10% glycerol), and the sortase was stored at −20° C. for short term use or −80° C. for long term

Example 1

Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

```
Tencon:
LPAPKNLVVSEVTEDSLRLSWTAPDAAFDSFLIQYQESEKVGEAINLTVPG

SERSYDLTGLKPGTEYTVSIYGVKGGHRSNPLSAEFTT (SEQ ID NO

1):
```

Various libraries were generated using the tencon scaffold and various design strategies. In general, libraries TCL1 and TCL2 produced good binders. Generation of TCL1 and TCL2 libraries are described in detail in Int. Pat. Publ. No. WO2014081944A2.

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO: 55). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

TCL1 library (SEQ ID NO: 2)

LPAPKNLVVSEVTEDSLRLSWTAPDAAFDSFLIQYQESEKVGEAINLTVPG

SERSYDLTGLKPGTEYTVSIYGV$X_{7-12}$PLSAEFTT;

wherein $X_1$, $X_2$, $X_3$, $X_4$, $X_5$, $X_6$, $X_7$ is any amino acid; and $X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library (SEQ ID NO: 3)

LPAPKNLVVSEVTEDSLRLSW$X_1X_2X_3X_4X_5X_6X_7X_8$SFLIQYQESEKVGEAI

NLTVPGSERSYDLTGLKPGTEYTVSIYGV$X_9X_{10}X_{11}X_{12}X_{13}$S$X_{14}X_{15}$LSAEF

TT;

wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

TABLE 2

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

```
Stabilized Tencon (Tencon27)
                                        (SEQ ID NO: 4)
LPAPKNLVVSRVTEDSARLSWTAPDAAFDSFLIQYQESEKVGEAIVLTVPG

SERSYDLTGLKPGTEYTVSIYGVKGGHRSNPLSAIFTT
```

```
TCL7 (randomized FG and BC loops)
                                        (SEQ ID NO: 5)
```

LPAPKNLVVSRVTEDSARLSW$X_1X_2X_3X_4X_5X_6X_7X_8X_9$FDSFLIQYQESEKV

GEAIVLTVPGSERSYDLTGLKPGTEYTVSIYGV$X_{10}X_{11}X_{12}X_{13}X_{14}X_{15}X_{16}$ $X_{17}X_{18}X_{19}$SNPLSAIFTT;

wherein $X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ is A, D, E, F, G, H, I, K, L, N, P, Q, R, S, T, V, W or Y; and $X_7$, $X_8$, $X_9$, $X_{17}$, $X_{18}$ and $X_{19}$, is A, D, E, F, G, H, I, K, L, N, P, Q, R, S, T, V, W, Y or deleted.

```
TCL9 (randomized FG loop)
                                        (SEQ ID NO: 6)
LPAPKNLVVSRVTEDSARLSWTAPDAAFDSFLIQYQESEKVGEAIVLTVPG
```

SERSYDLTGLKPGTEYTVSIYGV$X_1X_2X_3X_4X_5X_6X_7X_8X_9X_{10}X_{11}X_{12}$SNPLSA

IFTT;

$X_1$, $X_2$, $X_3$, $X_4$, $X_5$, $X_6$ and $X_7$, is A, D, E, F, G, H, I, K, L, N, P, Q, R, S, T, V, W or Y; and $X_8$, $X_9$, $X_{10}$, $X_{11}$ and $X_{12}$ is A, D, E, F, G, H, I, K, L, N, P, Q, R, S, T, V, W, Y or deleted.

For library construction, DNA fragments encoding randomized BC loops (lengths 6-9 positions) or FG loops (lengths 7-12 positions) were synthesized using Slonomics® protein synthesis technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen®) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 μg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen® spin column. The yield for each sub-library of TCL9 ranged from 32-34 μg.

Construction of FG/BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID No. 13-16) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide endoding for amino acid A17 (130 mer-L17A, SEQ ID No. 17) was produced by PCR using oligos POP2222ext (SEQ ID No. 18) and LS1114 (SEQ ID No. 19). This was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID No. 20) and LS1117 (SEQ ID No. 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen® PCR purification kit. The purified DNA was digested with BsaI-HF and gel purified.

Fragments encoding the FG loop were amplified by PCR using FG7, FG8, FG9, FG10, FG11, and FG12 as templates with oligonucleotides SDG10 (SEQ ID No. 22) and SDG24 (SEQ ID No. 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO: 24) and SDG28 (SEQ ID NO: 25). 7.5 μg of each reaction product were then digested with NotI and cleaned up with a Qiagen® PCR purification column. 5.2 μg of this DNA was ligated to an equal molar amount of RepA DNA fragment (~14 μg) digested with PspOMI and the product amplified by PCR using oligos POP2222.

Example 2

Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in U.S. Pat. Publ. No. US2013/0226834.

TCL14 library (SEQ ID NO: 7):
LPAPKNLVVSRVTEDSARLSWTAPDAAFDSF$X_1$I$X_2$Y$X_3$E$X_4X_5X_6X_7$GEAIV
LTVPGSERSYDLTGLKPGTEY$X_8$V$X_9$I$X_{10}$GVKGG$X_{11}X_{12}$SXDPLSAIFTT;

wherein $X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D, E, F, G, H, I, K, L, N, P, Q, R, S, T, V, W, Y, C or M.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 3. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and 186 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

TCL24 Library
(SEQ ID NO: 8)
LPAPKNLVVSRVTEDSARLSWTAPDAAFDSF$X_1$I$X_2$Y$X_3$E$X_4X_5X_6X_7$GEAI$X_8$
L$X_9$VPGSERSYDLTGLKPGTEY$X_{10}$V$X_{11}$I$X_{12}$GVKGG$X_{13}X_{14}$S$X_{15}$PL$X_{16}$A$X_{17}$
FTT;

wherein $X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$ are A, D, E, F, G, H, I, K, L, N, P, Q, R, S, T, V, Y or W.

TABLE 3

Amino acid frequency (%) at each randomized position for TCL21, TCL23, and TCL24.

| Amino Acid | TCL19 | TCL21 | TCL23 | TCL24 |
|---|---|---|---|---|
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |

TABLE 3-continued

| Amino acid frequency (%) at each randomized position for TCL21, TCL23, and TCL24. | | | | |
|---|---|---|---|---|
| Amino Acid | TCL19 | TCL21 | TCL23 | TCL24 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra® protein library technology (Isogenica®) in order to control amino acid distributions. TCL19, TCL23, and TCL24 gene fragments were generated using Slonomics® technology (MorphoSys®) to control amino acid distributions. PCR was used to amplify each library following initial synthesis followed by ligation to the gene for RepA in order to be used in selections using the CIS-display system (Odegrip et al., Proc Natl Acad Sci USA 101: 2806-2810, 2004) as described above for the loop libraries.

Example 3

Selection of Fibronectin Type III (FN3) Domains that Bind PSMA Plate-Based Selections CIS-display was used to select PSMA binding Centyrins™ from the TCL7, TCL9, TCL19, and TCL21 libraries. For in vitro transcription and translation (ITT), 3 μg of library DNA were incubated at 30° C. with 0.1 mM complete amino acids, 1×S30 premix components, and 15 μL of S30 extract system (Promega®) in a total volume of 50 μL. After 1 hour, 375 μL of blocking solution (1×TBS pH 7.4, 0.01% I-Block™ (protein-based blocking reagent; Life Technologies™, #T2015), 100 μg/mL herring sperm DNA) was added and reactions were incubated on ice for 15 minutes. ITT reactions were incubated with recombinant proteins, chimpanzee (pan 229) or cynomolgus monkey PSMA (pan 230), or cynomolgus monkey PSMA-Fc fusion (pan 231), which were immobilized on anti-human PSMA antibody (Lifespan Bioscience, catalog #LC-C150527) coated 96-well Maxisorb plates. Unbound library members were removed by successive washes with TBST and TBS. After washing, DNA was eluted from the target protein by heating to 85° C. for 10 minutes and amplified by PCR for further rounds of panning. High affinity binders were isolated by successively lowering the concentration of target PSMA during each round from 400 nM to 100 nM and increasing the washing stringency.

Following panning, selected FN3 domains were amplified by PCR, subcloned into a pET vector modified to include a ligase independent cloning site, and transformed into BL21-GOLD (DE3) (Stratagene) cells for soluble expression in *E. coli* using standard molecular biology techniques. A gene sequence encoding a C-terminal poly-histidine tag was added to each FN3 domain to enable purification and detection. Cultures were grown to an optical density of 0.6-0.8 in TB medium supplemented with 100 g/mL carbenicillin in 1-mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen® EMD Biosciences) with shaking at room temperature for 45 minutes.

Bead-Based Selections

Centyrins were also selected using a bead-based capture setup. ITT reactions were prepared as described above and then incubated with biotinylated recombinant proteins, chimpanzee or cynomolgus monkey PSMA. The biotinylated recombinant proteins and the bound library members were captured on neutravidin or streptavidin coated magnetic beads. Unbound library members were removed by successive washes with TBST and TBS. After washing, DNA was eluted from the target protein by heating to 85° C. for 10 minutes and amplified by PCR for further rounds of panning. High affinity binders were isolated by successively lowering the concentration of target PSMA during each round from 400 nM to 100 nM and increasing the washing stringency.

Off-Rate Selections

Outputs from the fifth round of bead-based selection were subjected to four rounds of off-rate selection. After the ITT reactions were incubated with biotinylated recombinant chimpanzee or cynomolgus monkey proteins, the proteins and the bound library members were captured on neutravidin or streptavidin coated magnetic beads, and washed in TBST extensively, the bound complexes were washed in 5 μM cold recombinant PSMA proteins for 1 hour. Then the ITT bound to beads were washed extensively in TBST and TBS before being eluted. The biotinylated target antigen concentration was stepped down from 25 nM in rounds 6 and 7 to 2.5 nM in rounds 8 and 9. Selection outputs from rounds 7 and 9 were subcloned into the modified pET15 vector for expression and screening.

Affinity Maturation Library Selection

An affinity maturation library (TCL25) based on the sequence of clone P229CR9P819-H11 (SEQ ID NO: 40) was generated using Slonomics technology at Morphosys (Munich, Germany) in which positions 23-30 from the BC loop and positions 78-83 from the FG loop were randomized. Maintenance of target binding in the library was achieved by doping nucleotides encoding the parent amino acid (from P229CR9P819-H11) at a target frequency of 65% at each randomized position. The remaining 35% of nucleotides were designed to contain a mixture of codons encoding for an equal probability of all other 20 natural amino acids, with the exception of cysteine and methionine which were not included. Table 4 shows the design of the TCL25 maturation library. In the table, numbers in parenthesis represent the percentage of molecules in the library designed to contain the corresponding amino acid at each position. This doping scheme (65% parent at 14 positions) generates a theoretical distribution of molecules containing mostly 3, 4, 5, 6, or 7 changes as compared to the parent molecule.

TABLE 4

| Position | Parent Amino Acid | Amino Acid Distribution (%) |
|---|---|---|
| 23 | Asp | (2.05), arg (2.05), asn (2.05), asp (65), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 24 | Ile | ala (2.05), arg (2.05), asn (2.05), asp (2.05), gln (2.05), glu (2.05), gly (2.05), his (2.05), ile (65), leu (2.05), lys (2.05), phe (2.05), pro (2.05), ser (2.05), thr (2.05), tyr(2.05), trp (2.05), val (2.05) |
| 25 | Asp | ala (2.05), arg (2.05), asn (2.05), asp (65), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 26 | Glu | ala (2.05), arg (2.05), asn (2.05), asp (2.05), gln (2.05), glu (65), gly (2.05), his (2.05), ile (2.05), leu (2.05), lys (2.05), phe (2.05), pro (2.05), ser (2.05), thr (2.05), tyr(2.05), trp (2.05), val (2.05) |
| 27 | Gln | ala (2.05), arg (2.05), asn (2.05), asp (2.05), gln (65), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 28 | Arg | ala (2.05), arg (65), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 29 | Asp | ala (2.05), arg (2.05), asn (2.05), asp (65), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 30 | Trp | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (65), val (2.05) |
| 78 | Tyr | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(65), trp (2.05), val (2.05) |
| 79 | His | ala (2.05), arg (2.05), asn (2.05), asp (2.05), gln (2.05), glu (2.05), gly (2.05), his (65), ile (2.05), leu (2.05), lys (2.05), phe (2.05), pro (2.05), ser (2.05), thr (2.05), tyr(2.05), trp (2.05), val (2.05) |
| 80 | Val | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (65) |
| 81 | Tyr | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(65), trp (2.05), val (2.05) |
| 82 | Arg | ala (2.05), arg (65), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 83 | Ser | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (65), thr (2.05), tyr(2.05), trp (2.05), val (2.05) |

CIS-display was used to select PSMA binding Centyrins from TCL25 library. The ITT reactions were incubated with biotinylated recombinant proteins, chimpanzee or cyno monkey PSMA. The biotinylated recombinant proteins and the bound library members were captured on neutravidin or streptavidin coated magnetic beads. Unbound library members were removed by successive washes with TBST and TBS. After washing, DNA was eluted from the target protein by heating to 85° C. for 10 minutes and amplified by PCR for further rounds of panning. Centyrin binders were isolated by successively lowering the concentration of target PSMA during each round from 400 nM to 100 nM and increasing the washing stringency.

Outputs from the second round selection were subjected to four rounds of off-rate selection. After the ITT reactions were incubated biotinylated recombinant PSMA proteins, the proteins and the bound library members were captured on neutravidin or streptavidin coated magnetic beads, and washed in TBST extensively, the bound complexes were washed in 5 μM cold recombinant PSMA proteins for 1 hour. Then the ITT bound to beads were washed extensively in TBST and TBS before being eluted. The biotinylated target antigen concentration was stepped down from 25 nM in rounds 3 and 4 to 2.5 nM in rounds 5 and 6. Selection outputs from rounds 7 and 9 were subcloned into the modified pET15 vector for expression and screening.

Biochemical Screening for Centyrins that Bind PSMA

Neutravidin-coated plates were blocked for 1 hour in StartingBlock™ T20 (blocking reagent; Pierce™) and then coated with biotinylated PSMA (using same antigen as in panning) or negative control for 1 hour. Plates were rinsed with TBST and diluted lysate was applied to plates for 1 hour. Following additional rinses, wells were treated with HRP-conjugated anti-Centyrin™ antibody (PAB25) for 1 hour and then assayed with POD (Roche®, peroxidase). Centyrins™ with signals at least 10-fold above background were selected for further analysis.

Size Exclusion Chromatography Analysis

Size exclusion chromatography was used to determine the aggregation state of PSMA binding Centyrins™. Aliquots (10 μL) of each purified Centyrin™ were injected onto a Superdex® 75 5/150 size exclusion column (GE Healthcare®) at a flow rate of 0.3 mL/min in a mobile phase of PBS pH 7.4. Elution from the column was monitored by absorbance at 280 nm. Wild type Tencon was included in each run as a control. Agilent® ChemStation software (Rev. B. 04.02) was used to analyse the elution profiles. Only those proteins with elution profiles similar to that of wild type protein in the same run were considered for further characterization.

High-Throughput Expression, Conjugation and Purification of Centyrins

Isolated clones from unique hits identified by biochemical binding ELISA were combined into a single hit plate for growth in 96-well block plates; clones grew in 1 mL cultures (LB media supplemented with kanamycin for selection) at 37° C. overnight with shaking. For protein expression in 96-block plates, 1 mL TB media supplemented with kanamycin was inoculated with 50 uL of the overnight culture and grown at 37° C. with continual shaking at 300 rpm until OD600=0.6-1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Both positive and negative controls were included in replicate on every plate.

For conjugation to the sortase tag, bacterial pellets were thawed, resuspended and lysed in BugBusterHT® lysis buffer (EMD Millipore®, Catalog #70922) supplemented with recombinant human lysozyme (EMD Millipore®, Catalog #71110). Lysis proceeded at room temperature with gentle agitation, after which the plate was transferred to a 42° C. to precipitate host proteins. Debris was pelleted by centrifugation, and supernatants were transferred to a new block plate for sortase-catalyzed labeling. A master mix containing Gly3-vc-MMAF (Concortis), tag-less SortaseA, and sortase buffer (Tris, sodium chloride, and calcium chloride) was prepared at a 2× concentration and added in equal volume to the lysate supernatants. The labeling reaction proceeded for two hours at room temperature, after which proteins were purified using a Ni-NTA multi-trap HP plate (GE Catalog #28-4009-89). Protein conjugates were recovered by step elution with imidazole-containing elution buffer (50 mM Tris pH7.5, 500 mM NaCl, 250 mM imidazole), filter sterilized and used directly for cell based cytotoxicity assays.

High-Throughput Cytotoxicity Assay of Centyrin-Drug Conjugates 96-well black tissue culture-coated plates (BD/Corning Catalog #353219) were seeded with LNCaP FGC cells (ATCC®, Catalog #CRL-1740) at a density of 10,000 cells/well in assay media (Life Technologies™, Catalog #11835-030) supplemented with 5% fetal bovine serum). Seeded plates were incubated overnight at 37° C. with 5% $CO_2$ to allow for cell attachment. Twenty-four hours later, CDCs were diluted in assay media (1:100, 1:300, 1:1000, or 1:3000) and applied directly to LNCaP cells. LNCaP cells then incubated at 37° C., 5% $CO_2$ for 66-72 hours. Cell toxicity was assessed using CellTiter-Glo® viability reagent (Promega®, Catalog #G7571); 100 μL prepared reagent was added directly to treated wells and incubated for ten minutes with gentle shaking, protected from light. Luminescence was measured using a SpectraMax® M5 plate reader. Values were normalized to untreated controls and selected for further analysis if more than 50% toxicity was achieved.

Example 4

Characterization of Anti-PSMA Centyrins

Large-Scale Expression and Purification

Gene sequences encoding Centyrin™ mutants were discovered through panning and cloned into the pET15b vector for expression under the T7 promoter or produced by DNA2.0® and subcloned into pJexpress401 vector (DNA2.0®) for expression under the T5 promoter. The resulting plasmids were transformed into *E. coli* BL21 Gold cells (Agilent®) or BL21DE3 Gold cells (Agilent®) for expression. A single colony was picked and grown in Luria Broth (Teknova®) supplemented with kanamycin and incubated 18 h at 37° C. 250 RPM. One liter Terrific Broth (Teknova®), supplemented with kanamycin, was inoculated from these subcultures and grown at 37° C. for 4 h while shaking. Protein expression was induced with 1 mM IPTG, once the optical density at the absorption of 600 nm reached 1.0. The protein was expressed for 4 h at 37° C. or 18 h at 30° C. Cells were harvested by centrifugation at 6000 g and stored at −20 C until purification. The frozen cell pellet (~15-25 g) was thawed for 30 min at room temperature and suspended in BugBuster® HT protein extraction reagent (EMD Millipore®) supplemented with 0.2 mg/mL recombinant lysozyme (Sigma) at 5 mL per gram of cell paste and incubated for 1 h on a shaker at room temperature. The lysate was clarified by centrifugation at 74 600 g for 25 min. The supernatant was applied onto a 5 mL Qiagen® Ni-NTA (nickle-charged resin) cartridge immersed in ice at a flow rate of 4 mL/min using an AKTA AVANT chromatography system. All other Ni-NTA chromatography steps were performed at flow rate 5 mL/min. The Ni-NTA column was equilibrated in 25.0 mL of 50 mM Tris-HCl buffer, pH 7.0 containing 0.5 M NaCl and 10 mM imidazole (Buffer A). After loading, the column was washed with 100 mL of Buffer A, followed by 100 mL of 50 mM Tris-HCl buffer, pH 7.0 containing 10 mM imidazole, 1% CHAPS and 1% n-octyl-ß-D-glucopyranoside detergents, and 100 mL Buffer A. The protein was eluted with Buffer A supplemented with 250 mM imidazole and loaded on a preparative gel-filtration column, TSKgel® G3000SW liquid chromatography column 21.5×600 mm (Tosoh®) equilibrated in PBS (Gibco®). The gel-filtration chromatography was performed at room temperature in PBS at flow rate 10 mL/min using an AKTA-AVANT chromatography system.

Determination of Thermal Stability

Thermal stability was measured by capillary DSC. Each sample was diluted in PBS pH 7.4 to a concentration of 1 mg/ml. Melting temperatures were measured for these samples using a VP-DSC instrument equipped with an autosampler (MicroCal, LLC). Samples were heated from 10 to 95° C. or 100° C. at a rate of 1° C. per minute. A buffer only scan was completed between each sample scan in order to calculate a baseline for integration. Data were fit to a two-state unfolding model following subtraction of the buffer only signal. Reversibility of thermal denaturation was determined by repeating the scan for each sample without removing it from the cell.

Selective Cytotoxicity of Anti-PSMA Centyrin Drug Conjugates on PSMA+ Cells

Centyrins™ were conjugated to vc-MMAF through either cysteine-maleimide chemistry (Brinkley, Bioconjugate Chemistry 3: 2-13, 1992) or using the sortase reaction described above. Cytotoxicity of Centyrin™-vcMMAF conjugates was assessed in LNCaP, VCAP, MDA-PC-2B, and PC3 cells in vitro. Cells were plated in 96-well black plates for 24 h and then treated with variable doses of Centyrin™-vcMMAF conjugates. Cells were allowed to incubate with Centyrin™ drug conjugates (CDCs) for 66-72 h 66-72 hours. CellTiter-Glo® was used to assess toxicity, as described above. Luminescence values were imported into Excel, from which they were copied and pasted into Prism® software for graphical analysis. Data were transformed using X=Log(x), then analyzed using nonlinear regression, applying a 3-parameter model to determine $IC_{50}$.

Table 6 summarizes the unique hits identified through panning, spanning multiple sequence families. Centyrins exhibited thermal stabilities between 55° to 85° C. and were cytotoxic to LNCaP cells when conjugated to vcMMAF, with $IC_{50}$ values from 22.6-0.38 nM.

Example 4

Characterization of Anti-PSMA Centyrins

Large-Scale Expression and Purification

Gene sequences encoding Centyrin™ mutants were discovered through panning and cloned into the pET15b vector for expression under the T7 promoter or produced by DNA2.0® and subcloned into pJexpress401 vector (DNA2.0®) for expression under the T5 promoter. The resulting plasmids were transformed into *E. coli* BL21 Gold cells (Agilent®) or BL21DE3 Gold cells (Agilent®) for expression. A single colony was picked and grown in Luria Broth (Teknova®) supplemented with kanamycin and incubated 18 h at 37° C. 250 RPM. One liter Terrific Broth (Teknova®), supplemented with kanamycin, was inoculated from these subcultures and grown at 37° C. for 4 h while shaking. Protein expression was induced with 1 mM IPTG, once the optical density at the absorption of 600 nm reached 1.0. The protein was expressed for 4 h at 37° C. or 18 h at 30° C. Cells were harvested by centrifugation at 6000 g and stored at −20 C until purification. The frozen cell pellet (~15-25 g) was thawed for 30 min at room temperature and suspended in BugBuster® HT protein extraction reagent (EMD Millipore®) supplemented with 0.2 mg/mL recombinant lysozyme (Sigma) at 5 mL per gram of cell paste and incubated for 1 h on a shaker at room temperature. The lysate was clarified by centrifugation at 74 600 g for 25 min. The supernatant was applied onto a 5 mL Qiagen® Ni-NTA cartridge (nickle-charged resin) immersed in ice at a flow rate of 4 mL/min using an AKTA AVANT chromatography system. All other Ni-NTA chromatography steps were performed at flow rate 5 mL/min. The Ni-NTA column was equilibrated in 25.0 mL of 50 mM Tris-HCl buffer, pH 7.0 containing 0.5 M NaCl and 10 mM imidazole (Buffer A). After loading, the column was washed with 100 mL, of Buffer A, followed by 100 mL of 50 mM Tris-HCl buffer, pH7.0 containing 10 mM imidazole, 1% CHAPS and 1% n-octyl-β-D-glucopyranoside detergents, and 100 mL Buffer A. The protein was eluted with Buffer A supplemented with 250 mM imidazole and loaded on a preparative gel-filtration column, TSKgel® G3000SW 21.5×600 mm liquid chromatography column (Tosoh®) equilibrated in PBS (Gibco®). The gel-filtration chromatography was performed at room temperature in PBS at flow rate 10 mL/min using an AKTA-AVANT chromatography system.

Determination of Thermal Stability

Thermal stability was measured by capillary DSC. Each sample was diluted in PBS pH 7.4 to a concentration of 1 mg/ml. Melting temperatures were measured for these samples using a VP-DSC instrument equipped with an autosampler (MicroCal, LLC). Samples were heated from 10 to 95° C. or 100° C. at a rate of 1° C. per minute. A buffer only scan was completed between each sample scan in order to calculate a baseline for integration. Data were fit to a two-state unfolding model following subtraction of the buffer only signal. Reversibility of thermal denaturation was determined by repeating the scan for each sample without removing it from the cell.

Selective Cytotoxicity of Anti-PSMA Centyrin Drug Conjugates on PSMA+ Cells

Centyrins™ were conjugated to vc-MMAF through either cysteine-maleimide chemistry (Brinkley, Bioconjugate Chemistry 3: 2-13, 1992) or using the sortase reaction described above. Cytotoxicity of Centyrin™-veMMAF conjugates was assessed in LNCaP, VCAP, MDA-PC-2B, and PC3 cells in vitro. Cells were plated in 96-well black plates for 24 hours and then treated with variable doses of Centyrin™-vcMMAF conjugates. Cells were allowed to incubate with Centyrin™ drug conjugates (CDCs) for 66-72 hours. CellTiter-Glo® was used to assess toxicity, as described above. Luminescence values were imported into Excel, from which they were copied and pasted into Prism® software for graphical analysis. Data were transformed using X=Log(x), then analyzed using nonlinear regression, applying a 3-parameter model to determine $IC_{50}$.

Table 5 summarizes the unique hits identified through panning, spanning multiple sequence families. Centyrins exhibited thermal stabilities between 55° to 85° C. and were cytotoxic to LNCaP cells when conjugated to vcMMAF, with $IC_{50}$ values from 22.6-0.38 nM. Table 6, 7 and 8 shows the BC, C, CD, F and FG loop amino acid sequences of select clones. Table 9 shows the amino acid sequences of the dines.

TABLE 5

| Clone ID | SEQ ID NO: | Antigen species | LNCaP $IC_{50}$ (nM) | Tm (° C.) |
|---|---|---|---|---|
| P229CR5P819_H11 | 40 | Chimp | 20.7 | 78.1 |
| P258AR6P1071_G03 | 35 | Cyno | 5.8 | 83.1 |
| P258AR6P1070_A05 | 36 | Cyno | 4.6 | 83 |
| P258AR6P1071_F04 | 37 | Cyno | 5.4 | 80.8 |
| P258AR6P1070_F09 | 38 | Cyno | 0.9 | 79.8 |
| P258AR6P1071_D02 | 39 | Cyno | 0.8 | 78.5 |
| P234CR9_H01 | 46 | Cyno | 22.6 | 74.1 |
| P234CR9_A7 | 45 | Cyno | 8.8 | ND |
| P233FR9_H10 | 41 | Chimp | 0.4 | 65.5 |
| P233FR9P1001_D9 | 44 | Chimp | 1.4 | 58.1 |
| P233FR9P1001_B5-5 | 42 | Chimp | 0.5 | 65 |
| P233FR9P1001_H3-1 | 43 | Chimp | 0.4 | 64.5 |

TABLE 6

| Clone ID | | BC loop | | C loop | |
|---|---|---|---|---|---|
| Clone ID | SEQ ID NO: | Sequence | SEQ ID NO: | Sequence | SEQ ID NO: |
| P229CR5P819_H11 | 40 | DIDEQRDW | 56 | FDSFLIQYQE | 63 |
| P258AR6P1071_G03 | 35 | DIDEQRDW | 56 | FDSFLIQYQE | 63 |
| P258AR6P1070_A05 | 36 | TIDEQRDW | 57 | FDSFLIQYQE | 63 |
| P258AR6P1071_F04 | 37 | VIDEQRDW | 58 | FDSFLIQYQE | 63 |
| P258AR6P1070_F09 | 38 | TIDEQRDW | 57 | FESFLIQYQE | 64 |
| P258AR6P1071_D02 | 39 | AIDEQRDW | 59 | FESFLIQYQE | 64 |

TABLE 6-continued

| Clone ID | SEQ ID NO: | BC loop Sequence | SEQ ID NO: | C loop Sequence | SEQ ID NO: |
|---|---|---|---|---|---|
| P234CR9_H01 | 46 | EWWVIPGD | 60 | FDSFLIQYQE | 63 |
| P234CR9_A7 | 45 | GEQFTI | 61 | FDSFLIQYQE | 63 |
| P233FR9_H10 | 41 | TAPDAA | 62 | FDSFAIGYWE | 65 |
| P233FR9P1001_D9 | 44 | TAPDAA | 62 | FDSFPIGYWE | 66 |
| P233FR9P1001_B5-5 | 42 | TAPDAA | 62 | FDSFTIGYWE | 67 |
| P233FR9P1001_H3-1 | 43 | TAPDAA | 62 | FDSFPIGYWE | 66 |

TABLE 7

| Clone ID | SEQ ID NO: | CD loop Sequence | SEQ ID NO: | F loop Sequence | SEQ ID NO: |
|---|---|---|---|---|---|
| P229CR5P819_H11 | 40 | SEKVGE | 68 | TEYTVSIYGV | 70 |
| P258AR6P1071_G03 | 35 | SEKVGE | 68 | TEYTVSIYGV | 70 |
| P258AR6P1070_A05 | 36 | SEKVGE | 68 | TEYTVSIYGV | 70 |
| P258AR6P1071_F04 | 37 | SEKVGE | 68 | TEYTVSIYGV | 70 |
| P258AR6P1070_F09 | 38 | SEKVGE | 68 | TEYTVSIYGV | 70 |
| P258AR6P1071_D02 | 39 | SEKVGE | 68 | TEYTVSIYGV | 70 |
| P234CR9_H01 | 46 | SEKVGE | 68 | TEYTVSIYGV | 70 |
| P234CR9_A7 | 45 | SEKVGE | 68 | TEYTVSIYG | 71 |
| P233FR9_H10 | 41 | WDDDGE | 69 | TEYPVYIAGV | 72 |
| P233FR9P1001_D9 | 44 | WDDDGE | 69 | TEYWVYIAGV | 73 |

TABLE 7-continued

| Clone ID | SEQ ID NO: | CD loop Sequence | SEQ ID NO: | F loop Sequence | SEQ ID NO: |
|---|---|---|---|---|---|
| P233FR9P1001_B5-5 | 42 | WDDDGE | 69 | TEYPVYIAGV | 72 |
| P233FR9P1001_H3-1 | 43 | WDDDGE | 69 | TEYHVYIAGV | 74 |

TABLE 8

| Clone ID | SEQ ID NO: | FG loop Sequence | SEQ ID NO: |
|---|---|---|---|
| P229CR5P819_H11 | 40 | YHVYRSSN | 75 |
| P258AR6P1071_G03 | 35 | YHVYRSN | 76 |
| P258AR6P1070_A05 | 36 | YHVYRSN | 76 |
| P258AR6P1071_F04 | 37 | YHVYRSN | 76 |
| P258AR6P1070_F09 | 38 | YHVYRSN | 76 |
| P258AR6P1071_D02 | 39 | YHVYRSN | 76 |
| P234CR9_H01 | 46 | VNSGQWNDTSN | 77 |
| P234CR9_A7 | 45 | ASGYEWFHAFGSSN | 78 |
| P233FR9_H10 | 41 | KGGQWSF | 79 |
| P233FR9P1001_D9 | 44 | KGGQWSF | 79 |
| P233FR9P1001_B5-5 | 42 | KGGQWSF | 79 |
| P233FR9P1001_H3-1 | 43 | KGGQWSF | 79 |

TABLE 9

| Clone ID | SEQ ID NO: | Clone Sequence |
|---|---|---|
| P229CR5P819_H11 | 40 | LPAPKNLVVSRVTEDSARLSWDIDEQRDWFDSFLIQYQESEKVGEAIVLTVPGSERSYDLTGLKPGTEYTVSIYGVYHVYRSSNPLSAIFTT |
| P258AR6P1071_G03 | 35 | LPAPKNLVVSRVTEDSARLSWDIDEQRDWFDSFLIQYQESEKVGEAIVLTVPGSERSYDLTGLKPGTEYTVSIYGVYHVYRSNPLSAIFTT |
| P258AR6P1070_A05 | 36 | LPAPKNLVVSRVTEDSARLSWTIDEQRDWFDSFLIQYQESEKVGEAIVLTVPGSERSYDLTGLKPGTEYTVSIYGVYHVYRSNPLSAIFTT |
| P258AR6P1071_F04 | 37 | LPAPKNLVVSRVTEDSARLSWVIDEQRDWFDSFLIQYQESEKVGEAIVLTVPGSERSYDLTGLKPGTEYTVSIYGVYHVYRSNPLSAIFTT |
| P258AR6P1070_F09 | 38 | LPAPKNLVVSRVTEDSARLSWTIDEQRDWFESFLIQYQESEKVGEAIVLTVPGSERSYDLTGLKPGTEYTVSIYGVYHVYRSNPLSAIFTT |

TABLE 9-continued

| Clone | | |
|---|---|---|
| Clone ID | SEQ ID NO: | Sequence |
| P258AR6P1071_D02 | 39 | LPAPKNLVVSRVTEDSARLSWAIDEQRDWFESFLIQYQESEKVGEAIVLTVPGSERSYDLTGLKPGTEYTVSIYGVYHVYRSNPLSAIFTT |
| P234CR9_H01 | 46 | LPAPKNLVVSRVTEDSARLSWEWWVIPGDFDSFLIQYQESEKVGEAIVLTVPGSERSYDLTGLKPGTEYTVSIYGVVNSGQWNDTSNPLSAIFTT |
| P234CR9_A7 | 45 | LPAPKNLVVSRVTEDSARLSWGEQFTIFDSFLIQYQESEKVGEAIVLTVPGSERSYDLTGLKPGTEYTVSIYGASGYEWFHAFGSSNPLSAIFTT |
| P233FR9_H10 | 41 | LPAPKNLVVSRVTEDSARLSWTAPDAAFDSFAIGYWEWDDDGEAIVLTVPGSERSYDLTGLKPGTEYPVYIAGVKGGQWSFPLSAIFTT |
| P233FR9P1001_D9 | 44 | LPAPKNLVVSRVTEDSARLSWTAPDAAFDSFPIGYWEWDDDGEAIVLTVPGSERSYDLTGLKPGTEYWVYIAGVKGGQWSFPLSAIFTT |
| P233FR9P1001_B5-5 | 42 | LPAPKNLVVSRVTEDSARLSWTAPDAAFDSFTIGYWEWDDDGEAIVLTVPGSERSYDLTGLKPGTEYPVYIAGVKGGQWSFPLSAIFTT |
| P233FR9P1001_H3-1 | 43 | LPAPKNLVVSRVTEDSARLSWTAPDAAFDSFPIGYWEWDDDGEAIVLTVPGSERSYDLTGLKPGTEYHVYIAGVKGGQWSFPLSAIFTT |

Select centyrin drug conjugates were tested across a panel of cell lines. Table 10 shows the $IC_{50}$ values for several centyrins conjugated to vcMMAF. Data represent averages between one and nine curve fits. Data are presented as average±SEM. CDCs were most potent in LNCaP cells, a line known to express high levels of PSMA. CDCs were also active in MDA-PCA-2B and VCAP cells, prostate cancer lines with lower levels of PSMA. No activity was observed in PC3 cells, a PSMA negative cell line, demonstrating selectivity.

TABLE 10

| | | Cytotoxicity Assays of Centyrin-Drug-Conjugates | | | |
|---|---|---|---|---|---|
| Clone | SEQ ID NO: | LNCaP cells $IC_{50}$ (nM) | MDA-PCA-2B cells $IC_{50}$ (nM) | VCAP cells $IC_{50}$ (nM) | PC3 cells $IC_{50}$ (nM) |
| P233FR9P1001-H3-1 | 43 | 0.4 | 4.6 ± 1.2 | 15.2 ± 1.0 | >500 |
| P234CR9_H01 | 46 | 22.6 | 150.8 ± 4.4 | 401.0 ± 130.0 | >500 |
| P233FR9_H10 | 41 | 0.5 ± 0.1 | 5.8 ± 2.3 | 25.9 ± 15.0 | >500 |
| P229CR5P819_H11 | 40 | 9.3 ± 1.9 | 106.8 ± 13.6 | 231.0 ± 38.0 | >500 |

Example 5

Engineering of Anti-PSMA Centyrins Cysteine Scan

Genes encoding anti-PSMA Centyrin, P233FR9_10 with cysteine residues introduced at various positions in the protein were obtained from DNA2.0 and used to express and purify proteins as described above. The resulting entyrins were evaluated for thermal stability (with and without vcMMAF conjugate) and LNCaP cytotoxicity, as described above. Results are summarized in Table 11.

TABLE 11

| Clone ID | SEQ ID NO: | Cysteine location* | Thermal stability (NEM capped) | Thermal Stability (vcMMAF conjugated) | LNCaP cytotoxicity ($IC_{50}$; nM) |
|---|---|---|---|---|---|
| P233FR9_H10(c-term) | 47 | c-terminal | TBD | TBD | ND |
| P233FR9_H10(K62C) | 51 | K62 | 56.91 | 54.03 | 0.69 |
| P233FR9_H10(R11C) | 50 | R11 | 65.72 | 63.58 | 0.40 |
| P233FR9_H10(E53C) | 49 | E53 | 66.75 | 65.98 | 0.66 |

*Residue numbering according to SEQ ID NO: 41

Example 6

Imaging Biodistribution of Untargeted Centyrins

A Centyrin™ with no specific binding to a target antigen engineered to contain a cysteine at position 62 was conjugated to DOTA and then a zirconium-89 radioisotope at IsoTherapeutics Group®, LLC (Angleton, TX.). Castrated male NSG mice (Jackson Laboratories) were anesthetized with 1.5% isoflurane and imaged in a Siemens® Inveon® microPET/CT. Mice were administered approximately 0.2 mCi Centyrin™ (SEQ ID NO: 51) via tail vein injection (made up to a 1 mg/kg dose with cold Centyrin™) and imaged continuously for the first 60 minutes, and then at 3, 6 and 24 hrs post injection of the Centyrin™.

Three-dimensional PET images were reconstructed using a 2D ordered-subsets expectation maximization algorithm (Siemens Healthcare, Knoxville, TN) into a 768×768×512 tomographic volume, with voxel size 0.107 mm×0.107 mm×0.107 mm. Images were processed and analyzed using PMOD v3.0 software (PMOD Technologies, Zurich, Switzerland). A cylinder of known activity was scanned in the PET scanner to provide a cross-calibration between injected dose measured by the dose calibrator, and counts per voxel in the PET images. Each PET image was co-registered to the CT image, to provide anatomical reference, using PMOD image fusion software. Regions of interest (ROI) were drawn around every 4th section for each tissue being analyzed. Mean counts per voxel were derived, and converted Percentage injected dose per gram of body weight, and using the correction factor derived from the calibration cylinder of known activity. All measures of radioactivity were corrected for decay, using the known half-life of Zr-89 (78.41 hours).

FIG. 1 shows the tissue distribution of radiolabeled FN3 domain over time. Rapid accumulation in the kidney and bladder is observed, with only limited accumulation in the liver, suggesting that Centyrins are cleared through the kidneys.

Example 7

Crystal Structure of Anti-PSMA P233FR9-H10 in Complex with Cyno PSMA

The His-tagged P233FR9-H10 centyrin (called herein as H10 centyrin) was expressed in *E. coli* and purified using affinity and size-exclusion chromatography. The centyrin was received in dPBS, pH 7.2.

The cynomolgus PSMA extracellular domain as a C-terminal fusion to the huIgG1 Fc domain was expressed in GnTT cells and purified by affinity and size-exclusion chromatography. The fusion protein was received in dPBS, 0.5 mM $ZnCl_2$, pH 7.2. Then, the Fc domain was removed with a Prescission protease treatment followed by affinity and size-exclusion chromatography. The isolated cynomolgus PSMA (cynoPSMA) extracellular domain was stored in dPBS, 0.5 mM $ZnCl_2$, pH 7.2.

The H10 centyrin/cynoPSMA complex was prepared by mixing cynoPSMA with H10 centyrin at a molar ratio of 1:3 (excess centyrin) while dialyzing for 48 h at 4° C. against 20 mM Hepes pH 7.0, 0.5 mM $ZnCl_2$. The complex was then eluted from a monoS column with a gradient of 48-68 mM NaCl, 20 mM Hepes pH 7.5, 10% glycerol and concentrated to 3.4 mg/mL. Crystals suitable for X-diffraction were obtained from 25% PEG 3 kDa, 0.2 M $NH_4Cl$, 0.1 M Na Acetate pH 4.5 using the sitting drop vapor-diffusion method at 20° C.

For X-ray data collection, the crystal was soaked for a few seconds in a cryo-protectant solution containing mother liquor supplemented with 20% glycerol, and then frozen in liquid nitrogen. X-ray diffraction data were collected with a Dectris Pilatus 6M Pixel Array detector at the beamline 17-ID of the Advanced Photon Source (APS) at Argonne National Laboratory. Diffraction data were processed with the program HKL2000 (Otwinowski & Minor, 1997). X-ray data statistics are given in Table 12.

The structure was solved by molecular replacement (MR) with Phaser (Read, 2001). The search models for MR were the crystal structures of human PSMA (PDB code 2C6G) and the structure of P114AR7P94-A3 W33A centyrin. The structures were refined with PHENIX (Adams et al, 2004) and model adjustments were carried out using COOT (Emsley & Cowtan, 2004). All other crystallographic calculations were performed with the CCP4 suite of programs (CCP4, 1994). All molecular graphics were generated with PyMol (DeLano, 2002). The structure refinement statistics are given in Table 12.

TABLE 12

| | PS42 |
|---|---|
| Crystal data | |
| Crystallization solution | |
| 0.1M Buffer | Acetate pH 4.5 |
| Precipitant | 25% PEG 3 kDa |
| Additive | 0.2M $NH_4Cl$ |
| Space group | $P2_12_12$ |
| Complex/asym. unit | 2 |
| Unit cell | |
| a (Å) | 84.0 |
| b (Å) | 109.9 |
| c (Å) | 261.6 |
| $V_m$ ($Å^3$/Da) | 3.32 |
| Solvent content (%) | 63 |
| X-ray data* | |
| Resolution (Å) | 50.00-2.80 |
| High Resolution Shell (Å) | (2.85-2.80) |
| Measured reflections | 335,467 |

TABLE 12-continued

| | PS42 |
|---|---|
| Unique reflections | 57,166 |
| Completeness (%) | 93.2 (69.3) |
| Redundancy | 5.9 (4.4) |
| Rsym (%) | 25.1 (64.1) |
| <I/σ> | 6.4 (1.6) |
| Refinement | |
| Resolution (Å) | 40.0-2.8 |
| Number of reflections | 57,063 |
| Number of all atoms | 12,330 |
| Number of waters | 8 |
| Rfactor (%) | 25.14 |
| Rfree (%) | 31.28 |
| RMSD | |
| bond lengths (Å) | 0.003 |
| bond angles (°) | 0.998 |
| Average B-factor (Å$^2$) | 78.9 |
| Ramachandran Plot | |
| favored region (%) | 94.9 |
| allowed region (%) | 4.8 |
| outliers (%) | 0.3 |

*Values for high resolution shell are in parenthesis.

The structure of the homodimeric cynoPSMA includes residues 57-750, corresponding to the protease (residues 57-116 and 352-590), apical (residues 117-351) and helical (residues 591-750) domains, and eight of eleven possible N-linked glycans (in Asn-76, -121, -140, -195, -459, -476, -613, and -638) per dimer subunit. The cynoPSMA active site is located at the interface between the three domains and it contains two zinc atoms coordinated by histidine (H377 and H553) and glutamate/aspartate (D387, catalytic E424, E425, and D453) residues and a water molecule. The H10 centyrin (SEQ ID NO: 41) structure contains residues 2-92. H10 residues are numbered sequentially according to SEQ ID NO: 41. cynoPSMA residues are numbered according to the full length cyno PSMA sequence of SEQ ID NO: 141. The mature cynoPSMA (without signal peptide) starts at residue 44 of SEQ ID NO: 141.

Figure 2A:
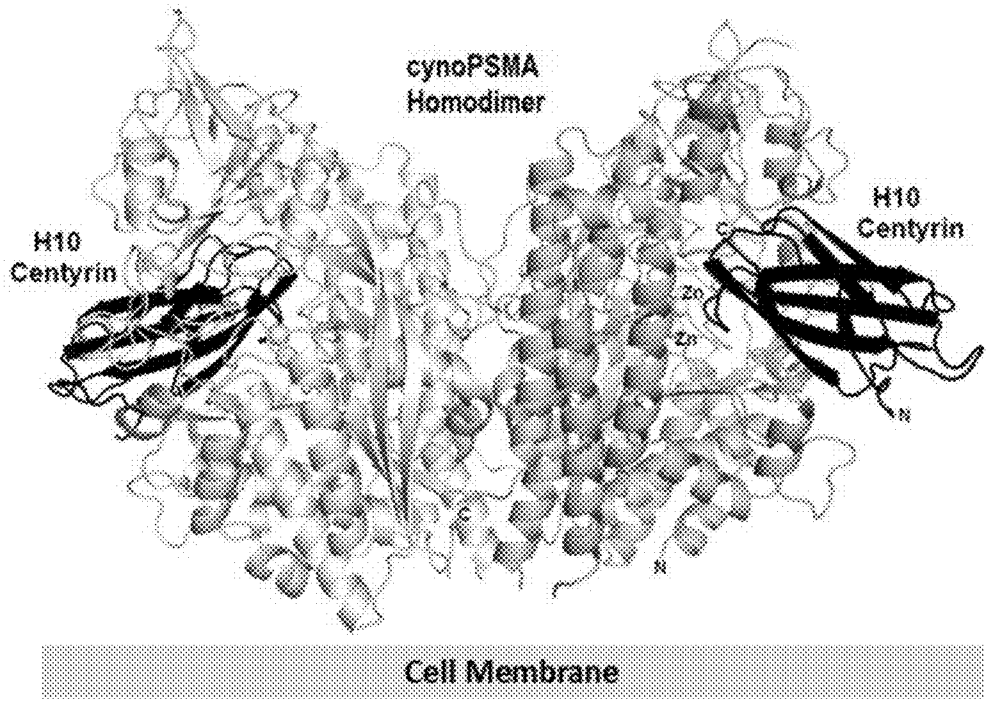
FIG. 2A shows the overall crystal structure of the P233FR9_H10 PSMA binding FN3 domain (H10) in complex with cynomolgous PSMA dimer, showing that H10 binds to the region near the PSMA active site. The zinc atoms (Zn) indicate the location of the PSMA active site. The N- and C-terminus of PSMA and H10 molecules are indicated for one of the complexes. The approximate location of the cell membrane is indicated.

There is one cynoPSMA homodimer in the asymmetric unit with one H10 centyrin bound to each PSMA subunit (FIG. 2A). The two centyrin/PSMA complexes are structurally very similar as indicated by the root mean square deviation (r.m.s.d.) of 0.72 Å for the superposition of all equivalent atoms in the PSMA subunits. Also, there is a high degree of structural similarity between human and cynomolgus PSMA and absence of large conformational changes induced by the centyrin binding, as indicated by a r.m.s.d of 0.5 Å for the Cα atom superposition between the cynoPSMA molecule in the centyrin complex and unbound human PSMA (PDB code 2OOT, structure at 1.6 Å resolution). An interesting feature is that the loop region 541-547 is visible only in the cynomolgus protein due to stabilization of the loop conformation through interactions with the centyrin.

The centyrin/PSMA combining site is well defined by the $2F_{obs}$-$F_{calc}$ electron density map, which allows reliable positioning of the binding residues. Only the interactions between the B and C chains (PSMA and centyrin chains, respectively) are described in the next section.

The H10 centyrin binds to a region near the PSMA active site (FIG. 2A) and covers a cynoPSMA area of about 1,170 Å$^2$. Specifically, the centyrin recognizes cynoPSMA residues in the protease (Y460, F488, K499-P502, P504, R511, K514, N540-E542, and N544-F546), apical (residue R181), and helical (residues K610, N613, and 1614) domains as shown in FIGS. 3 and 4.

Figure 2B:
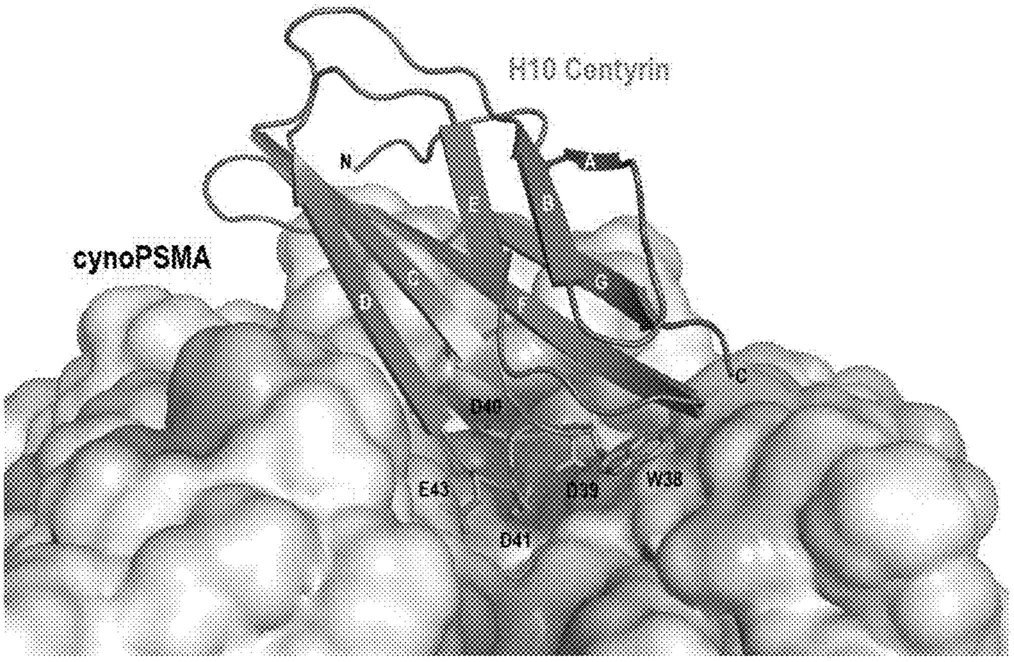
FIG. 2B shows the crystal structure of the H10 FN3 domain in complex with cynomolgous PSMA. The A, B, C, D, E, F and G beta strands in the H10 FN3 domain are shown. The negatively charged residues in the CD loop of H10 (residues W38, D39, D40, D41 and E43) that inserts into the positively charged entrance of the PSMA active site are shown. H10 residue numbering according to SEQ ID NO: 41.
Figure 2C:
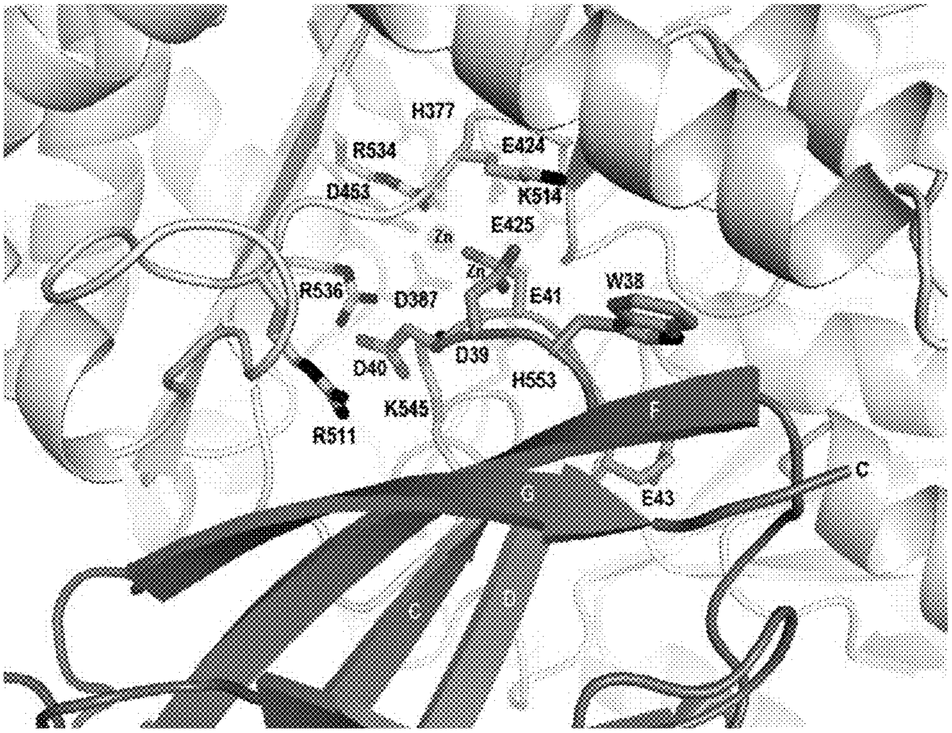
FIG. 2C shows the crystal structure of the H10 FN3 domain in complex with cynomolgous PSMA. The H10 contact residues W38, D39, D40, D41 and E43 are shown in the Figure. Some of the cyno PSMA residues that contact H10 (R511, K514 and K545), coordinate the zinc atoms (H377, D387, E424, E425, D453, and H553) or compose the active site cavity (R536 and R534) are shown. H10 beta strands C, D, F and G are marked in the Figure. H10 and cynomolgous PSMA residue numbering is according to SEQ ID NO: 41 and 141, respectively.

The face of the centyrin four-stranded β-sheet packs onto the PSMA surface with the CD loop deeply inserted into the active site entrance (FIGS. 2B and 2C). Specifically, the H10 centyrin residues involved in PSMA binding are located in the C (A32 and G34), D (V46), F (G64, P68, Y70, and A72), and G (S84-I86) β-strands and the CD (W36, W38-D41, E43, and A44) and FG loops (W79, F81, and P82). Residues D39, D40, D41, and E43 confer a negative charge to the centyrin CD loop and these residues are inserted into the ~20 Å deep, positively charged, funnel that leads to the zinc ions in the active site, likely blocking substrate entrance into the funnel and PSMA enzymatic activity (FIGS. 2B and 2C). However, the centyrin does not interact directly with the zinc ions or their coordinating residues.

Figure 3A:
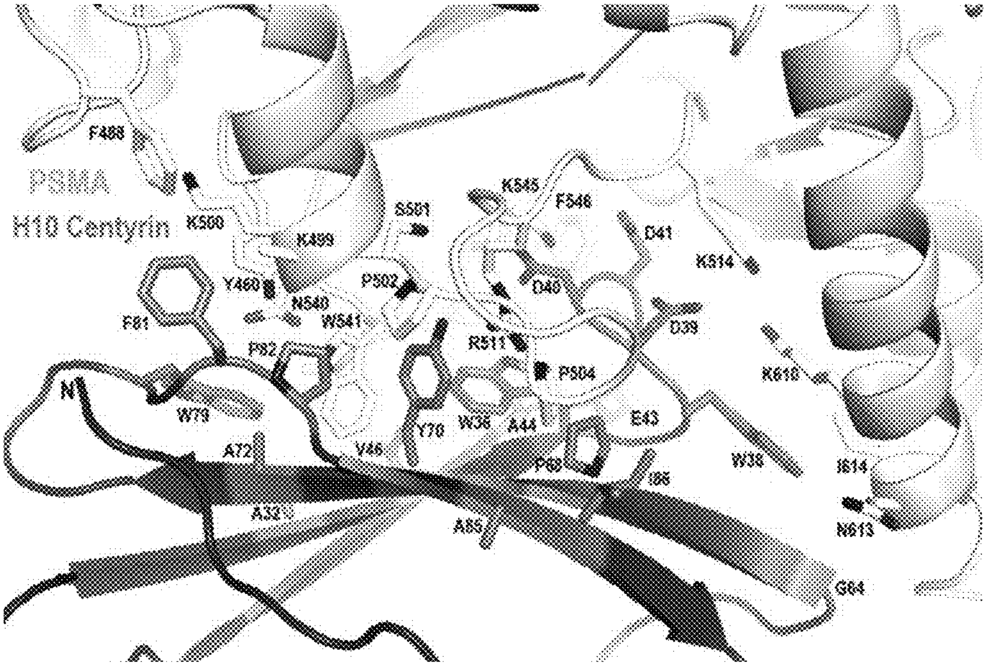
FIG. 3A shows a close view of the crystal structure combining site between the H10 FN3 domain and cynomolgous PSMA. The H10 FN3 domain contact residues A32, W36, W38-D41, E43, A44, V46, G64, P68, Y70, A72, W79, F81, P82, A85, and 186 are shown. The cyno PSMA contact residues Y460, K499-P502, P504, R511, K514, N540, W541, K545, F546, F488, K610, N613, and 1614 are shown. H10 and cynomolgous PSMA residue numbering is according to SEQ ID NO: 41 and 141, respectively.
Figure 3B:
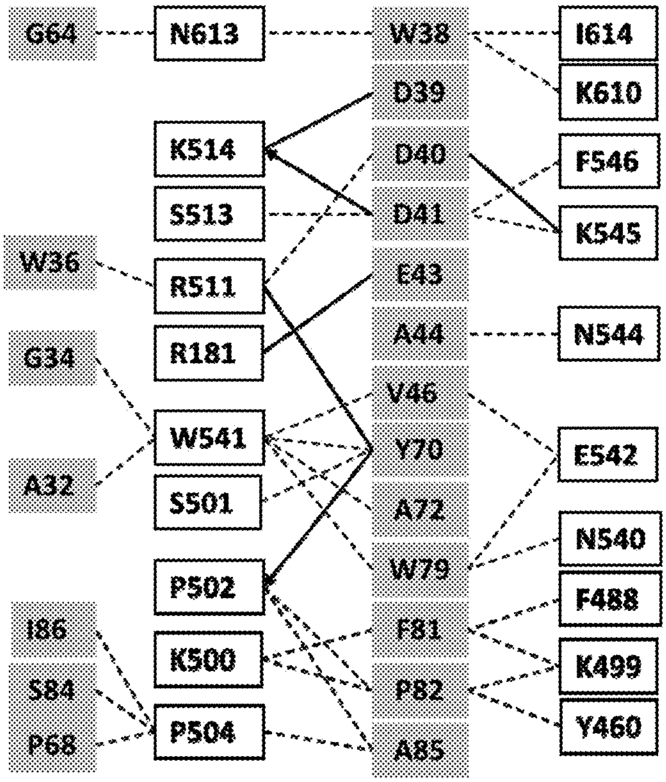
FIG. 3B shows an interaction map between the H10 FN3 domain and cynomolgous PSMA contact residues. A distance cut-off of 4 Å was used to define the contact residues. Centyrin and cyno PSMA residues are shown in gray and white boxes, respectively, van der Waals interactions are shown as dashed lines, and H-bonds are solid lines with arrows indicating backbone H bonds and pointing to the backbone atoms. Residue numbering is according to SEQ ID NO: 41 (H10) and SEQ ID NO: 141 (cyno PSMA).

Conserved PSMA residues W541, Y460, F488, P502 and P504 form an aromatic cluster across the combing site with centyrin residues W36, P68, Y70, W79, F81, and P82 (FIG. 3A). Conserved R511 is in a central location of the combining site and H bonds Y70, a central residue of the centyrin four-stranded β-sheet. FIG. 3B shows a cartoon of the paratope and epitope residues.

Human and cynomolgus PSMA are 97% identical, and, except for a S613N change, all residues interacting with H10 are conserved between the two species (FIG. 4). The S613N change results in N613 glycosylation in cynoPSMA and the gain of van der Waals contacts between the carbohydrate and centyrin residues E66, 186, T88 (F and G β-strands) that will not be present in the human enzyme.

Centyrin Residues for Conjugation

Figure 5:
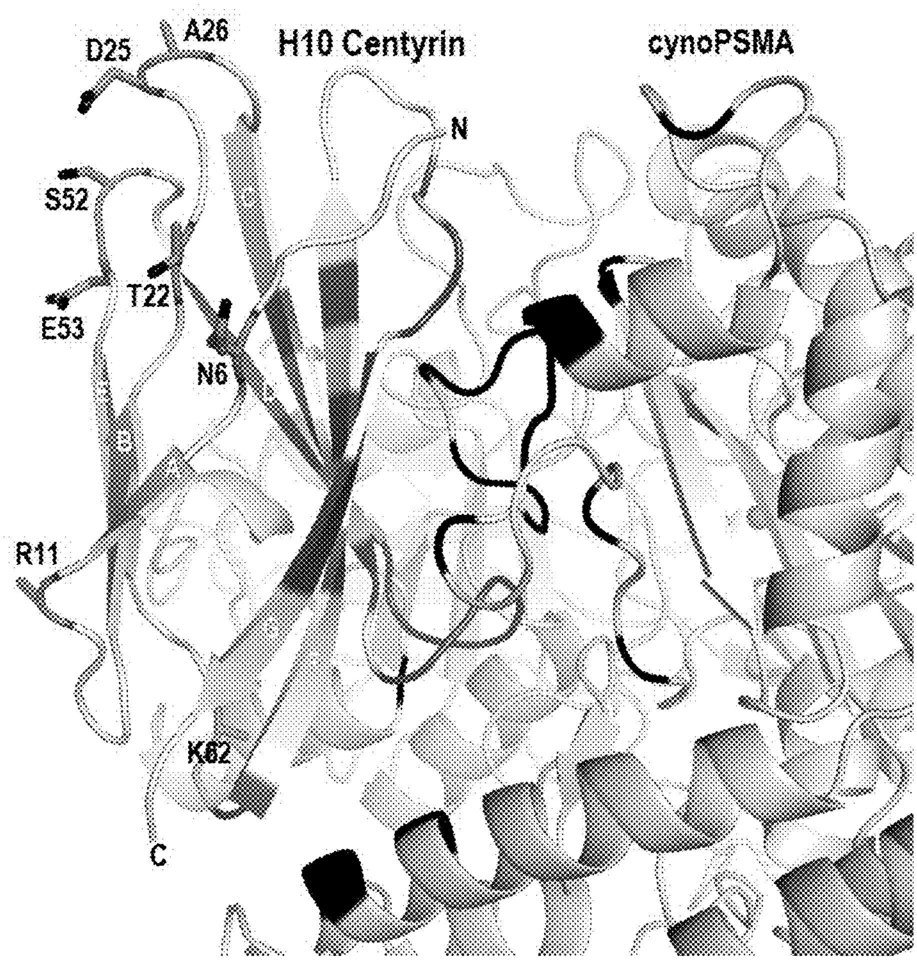
FIG. 5 shows the location of H10 centyrin residue N6, R11, T22, D25, A26, S52, E53, K62, and the N- and C-terminus, which are possible sites for chemical conjugation, in the crystal structure of H10 bound to cynomolgous PSMA. The centyrin/PSMA contacting regions are shown in black. H10 beta strands C, D, F and G are marked in the Figure. Residue numbering according to SEQ ID NO: 41 (H10).

Various H10 centyrin residues outside the combining site can be modified for conjugation of small molecules (toxic payloads) without disrupting PSMA binding or centyrin fold. Cysteines were already placed and conjugated to payloads at the C-terminus (after the His-tag) and at positions R11, E53, and K62 and all of these variants demonstrated similarly potent cytotoxicity. In addition, residues T22, D25, and A26 in the BC loop, terminal residue N6, and S52 in the DE loop are potentially good sites for mutagenesis followed by chemical conjugation (FIG. 5). These solvent exposed residues are away from the centyrin/PSMA interface and located in structurally flexible regions.

Furthermore, both N- and C-terminal regions are free for fusions with other protein domains. The N-terminus is oriented towards the PSMA protease domain and reachable with a fusion linker, while the also accessible C-terminus goes towards the PSMA helical domain. The optimal linker length to the centyrin fusion partner will depend on the structure of the fusion partner and location of its binding site on the target molecule.

Mechanism of Action

The H10 centyrin is a candidate for targeted delivery of payloads (toxic small molecules, nucleic acid, etc.) into prostate cancer cells due to internalization of the centyrin/PSMA complex. Furthermore, the H10 centyrin is a candidate for redirection of immune cells to prostate cancer cells when in a multispecific format.

H10 centyrin is likely to also inhibit the enzymatic activity of PSMA, which may contribute to decreased cell fitness and survival. The centyrin/cynoPSMA structure shows the centyrin bound to the entrance of the active site, which might prevent substrate interaction with PSMA through steric occlusion and direct competition for the binding site.

Example 8

Generation of Additional Anti-PSMA Centyrin Variants

Select anti-PSMA centyrins were further engineered to improve properties of the parental centyrins. Which FN3 domains binding to PSMA were generated using libraries described above, and tested for their binding to PSMA.

TABLE 13 shows the amino acid sequences of the generated molecules.

| Clone ID | SEQ ID NO: | Sequence |
|---|---|---|
| P258AR6P1071_D02_v1 | 75 | LPAPKNLVVSRVTEDSARLSWAADEQRDWFESFLIQYQESEKVGEAIVLTVPGSCRSYDLTGLKPGTEYTVSIYGVYHVYRSNPLSAIFTT |
| P258AR6P1071_D02_v2 | 76 | LPAPKNLVVSRVTEDSARLSWAIAEQRDWFESFLIQYQESEKVGEAIVLTVPGSCRSYDLTGLKPGTEYTVSIYGVYHVYRSNPLSAIFTT |
| P258AR6P1071_D02_v3 | 77 | LPAPKNLVVSRVTEDSARLSWAIDAQRDWFESFLIQYQESEKVGEAIVLTVPGSCRSYDLTGLKPGTEYTVSIYGVYHVYRSNPLSAIFTT |
| P258AR6P1071_D02_v4 | 78 | LPAPKNLVVSRVTEDSARLSWAIDEARDWFESFLIQYQESEKVGEAIVLTVPGSCRSYDLTGLKPGTEYTVSIYGVYHVYRSNPLSAIFTT |
| P258AR6P1071_D02_v5 | 79 | LPAPKNLVVSRVTEDSARLSWAIDEQADWFESFLIQYQESEKVGEAIVLTVPGSCRSYDLTGLKPGTEYTVSIYGVYHVYRSNPLSAIFTT |
| P258AR6P1071_D02_v6 | 80 | LPAPKNLVVSRVTEDSARLSWAIDEQRAWFESFLIQYQESEKVGEAIVLTVPGSCRSYDLTGLKPGTEYTVSIYGVYHVYRSNPLSAIFTT |
| P258AR6P1071_D02_v7 | 81 | LPAPKNLVVSRVTEDSARLSWAIDEQRDAFESFLIQYQESEKVGEAIVLTVPGSCRSYDLTGLKPGTEYTVSIYGVYHVYRSNPLSAIFTT |
| P258AR6P1071_D02_v8 | 82 | LPAPKNLVVSRVTEDSARLSWAIDEQRDWFESFLIQYQESEKVGEAIVLTVPGSCRSYDLTGLKPGTEYTVSIYGVAHVYRSNPLSAIFTT |
| P258AR6P1071_D02_v9 | 83 | LPAPKNLVVSRVTEDSARLSWAIDEQRDWFESFLIQYQESEKVGEAIVLTVPGSCRSYDLTGLKPGTEYTVSIYGVYAVYRSNPLSAIFTT |
| P258AR6P1071_D02_v10 | 84 | LPAPKNLVVSRVTEDSARLSWAIDEQRDWFESFLIQYQESEKVGEAIVLTVPGSCRSYDLTGLKPGTEYTVSIYGVYHAYRSNPLSAIFTT |
| P258AR6P1071_D02_v11 | 85 | LPAPKNLVVSRVTEDSARLSWAIDEQRDWFESFLIQYQESEKVGEAIVLTVPGSCRSYDLTGLKPGTEYTVSIYGVYHVARSNPLSAIFTT |
| P258AR6P1071_D02_v12 | 86 | LPAPKNLVVSRVTEDSARLSWAIDEQRDWFESFLIQYQESEKVGEAIVLTVPGSCRSYDLTGLKPGTEYTVSIYGVYHVYASNPLSAIFTT |
| P258AR6P1071_D02_v13 | 87 | LPAPKNLVVSRVTEDSARLSWAIDEQRDWFASFLIQYQESEKVGEAIVLTVPGSCRSYDLTGLKPGTEYTVSIYGVYHVYRSNPLSAIFTT |
| P258AR6P1071_D02_v14 | 88 | LPAPKNLVVSRVTEDSARLSWDIDEQRDWFESFLIQYQESEKVGEAIVLTVPGSCRSYDLTGLKPGTEYTVSIYGVYHVYRSNPLSAIFTT |
| P258AR6P1071_D02_v15 | 89 | LPAPKNLVVSRVTEDSARLSWAIDEQRDWFDSFLIQYQESEKVGEAIVLTVPGSCRSYDLTGLKPGTEYTVSIYGVYHVYRSNPLSAIFTT |
| P258AR6P1071_D02_v16 | 90 | LPAPKNLVVSRVTEDSARLSWAIDEQRDWFESFLIQYQESEKVGEAIVLTVPGSCRSYDLTGLKPGTEYTVSIYGVYHVYRSSNPLSAIFTT |
| P258AR6P1071_D02_v17 | 91 | LPAPKNLVVSRVTEDSARLSWDIDEQRDWFDSFLIQYQESEKVGEAIVLTVPGSCRSYDLTGLKPGTEYTVSIYGVYHVYRSNPLSAIFTT |
| P258AR6P1071_D02_v18 | 92 | LPAPKNLVVSRVTEDSARLSWDIDEQRDWFESFLIQYQESEKVGEAIVLTVPGSCRSYDLTGLKPGTEYTVSIYGVYHVYRSSNPLSAIFTT |

-continued

TABLE 13 shows the amino acid sequences of the generated molecules.

| Clone ID | SEQ ID NO: | Sequence |
|---|---|---|
| P258AR6P1071_D02_v19 | 93 | LPAPKNLVVSRVTEDSARLSWAIDEQRDWFDSFLIQYQESEKVGEAIVLTVPGSCRSYDLTGLKPGTEYTVSIYGVYHVYRSSNPLSAIFTT |
| P233FR9_H10_v1 | 94 | LPAPKNLVVSRVTEDSARLSWTAPDAAFDSFAIGYWEWDDDGEAIVLTVPGSCRSYDLTGLKPGTEYRVYIAGVKGGQWSFPLSAIFTT |
| P233FR9_H10_v2 | 95 | LPAPKNLVVSRVTEDSARLSWTAPDAAFDSFAIGYWEWDDDGEAIVLTVPGSCRSYDLTGLKPGTEYKVYIAGVKGGQWSFPLSAIFTT |
| P233FR9_H10_v3 | 96 | LPAPKNLVVSRVTEDSARLSWTAPDAAFDSFAIGYWEWDDDGEAIVLTVPGSCRSYDLTGLKPGTEYEVYIAGVKGGQWSFPLSAIFTT |
| P233FR9_H10_v4 | 97 | LPAPKNLVVSRVTEDSARLSWTAPDAAFDSFAIGYWEWDDDGEAIVLTVPGSCRSYDLTGLKPGTEYHVYIAGVKGGQWSFPLSAIFTT |
| P233FR9_H10_v5 | 98 | LPAPKNLVVSRVTEDSARLSWTAPDAAFDSFAIGYWEWDDDGEAIVLTVPGSCRSYDLTGLKPGTEYDVYIAGVKGGQWSFPLSAIFTT |
| P233FR9_H10_v6 | 99 | LPAPKNLVVSRVTEDSARLSWTAPDAAFDSFAIGYWEWDDDGEAIVLTVPGSCRSYDLTGLKPGTEYAVYIAGVKGGQWSFPLSAIFTT |
| P233FR9_H10_v7 | 100 | LPAPKNLVVSRVTEDSARLSWTAPDAAFDSFAIGYWEWDDDGEAIVLTVPGSCRSYDLTGLKPGTEYGVYIAGVKGGQWSFPLSAIFTT |
| P233FR9_H10_v8 | 101 | LPAPKNLVVSRVTEDSARLSWTAPDAAFDSFAIGYWEWDDDGEAIVLTVPGSCRSYDLTGLKPGTEYVVYIAGVKGGQWSFPLSAIFTT |
| P233FR9_H10_v9 | 102 | LPAPKNLVVSRVTEDSARLSWTAPDAAFDSFAIGYWEWDDDGEAIVLTVPGSCRSYDLTGLKPGTEYLVYIAGVKGGQWSFPLSAIFTT |
| P233FR9_H10_v10 | 103 | LPAPKNLVVSRVTEDSARLSWTAPDAAFDSFAIGYWEWDDDGEAIVLTVPGSCRSYDLTGLKPGTEYIVYIAGVKGGQWSFPLSAIFTT |
| P233FR9_H10_v11 | 104 | LPAPKNLVVSRVTEDSARLSWTAPDAAFDSFAIGYWEWDDDGEAIVLTVPGSCRSYDLTGLKPGTEYFVYIAGVKGGQWSFPLSAIFTT |
| P233FR9_H10_v12 | 105 | LPAPKNLVVSRVTEDSARLSWTAPDAAFDSFAIGYWEWDDDGEAIVLTVPGSCRSYDLTGLKPGTEYWVYIAGVKGGQWSFPLSAIFTT |
| P233FR9_H10_v13 | 106 | LPAPKNLVVSRVTEDSARLSWTAPDAAFDSFAIGYWEWDDDGEAIVLTVPGSCRSYDLTGLKPGTEYNVYIAGVKGGQWSFPLSAIFTT |
| P233FR9_H10_v14 | 107 | LPAPKNLVVSRVTEDSARLSWTAPDAAFDSFAIGYWEWDDDGEAIVLTVPGSCRSYDLTGLKPGTEYQVYIAGVKGGQWSFPLSAIFTT |
| P233FR9_H10_v15 | 108 | LPAPKNLVVSRVTEDSARLSWTAPDAAFDSFAIGYWEWDDDGEAIVLTVPGSCRSYDLTGLKPGTEYSVYIAGVKGGQWSFPLSAIFTT |
| P233FR9_H10_v16 | 109 | LPAPKNLVVSRVTEDSARLSWTAPDAAFDSFAIGYWEWDDDGEAIVLTVPGSCRSYDLTGLKPGTEYTVYIAGVKGGQWSFPLSAIFTT |
| P233FR9_H10_v17 | 110 | LPAPKNLVVSRVTEDSARLSWTAPDAAFDSFAIGYWEWDDDGEAIVLTVPGSCRSYDLTGLKPGTEYYVYIAGVKGGQWSFPLSAIFTT |

-continued

TABLE 13 shows the amino acid sequences of the generated molecules.

| Clone ID | SEQ ID NO: | Sequence |
|---|---|---|
| P233FR9_H10_v18 | 111 | LPAPKNLVVSRVTEDSARLSWTAPDAAFDSFAIAYWE WDDDGEAIVLTVPGSCRSYDLTGLKPGTEYPVYIAGV KGGQWSFPLSAIFTT |
| P233FR9_H10_v19 | 112 | LPAPKNLVVSRVTEDSARLSWTAPDAAFDSFAISYWE WDDDGEAIVLTVPGSCRSYDLTGLKPGTEYPVYIAGV KGGQWSFPLSAIFTT |
| P233FR9_H10_v20 | 113 | LPAPKNLVVSRVTEDSARLSWTAPDAAFDSFAIGYWE WDTDGEAIVLTVPGSCRSYDLTGLKPGTEYPVYIAGV KGGQWSFPLSAIFTT |
| P233FR9_H10_v21 | 114 | LPAPKNLVVSRVTEDSARLSWTAPDAAFDSFAIGYWE WDSDGEAIVLTVPGSCRSYDLTGLKPGTEYPVYIAGV KGGQWSFPLSAIFTT |
| P233FR9_H10_v22 | 115 | LPAPKNLVVSRVTEDSARLSWTAPDAAFDSFAIGYYE WDDDGEAIVLTVPGSCRSYDLTGLKPGTEYPVYIAGV KGGQWSFPLSAIFTT |
| P233FR9_H10_v23 | 116 | LPAPKNLVVSRVTEDSARLSWTAPDAAFDSFAIGYFE WDDDGEAIVLTVPGSCRSYDLTGLKPGTEYPVYIAGV KGGQWSFPLSAIFTT |
| P233FR9_H10_v24 | 117 | LPAPKNLVVSRVTEDSARLSWTAPDAAFDSFAIGYLE WDDDGEAIVLTVPGSCRSYDLTGLKPGTEYPVYIAGV KGGQWSFPLSAIFTT |
| P233FR9_H10_v25 | 118 | LPAPKNLVVSRVTEDSARLSWTAPDAAFDSFAIGYWE YDDDGEAIVLTVPGSCRSYDLTGLKPGTEYPVYIAGVK GGQWSFPLSAIFTT |
| P233FR9_H10_v26 | 119 | LPAPKNLVVSRVTEDSARLSWTAPDAAFDSFAIGYWE FDDDGEAIVLTVPGSCRSYDLTGLKPGTEYPVYIAGVK GGQWSFPLSAIFTT |
| P233FR9_H10_v27 | 120 | LPAPKNLVVSRVTEDSARLSWTAPDAAFDSFAIGYWE LDDDGEAIVLTVPGSCRSYDLTGLKPGTEYPVYIAGVK GGQWSFPLSAIFTT |
| P233FR9_H10_v28 | 121 | LPAPKNLVVSRVTEDSARLSWTAPDAAFDSFAIGYWE WDDDGEAIVLTVPGSCRSYDLTGLKPGTEYPVYIAGV KGGQYSFPLSAIFTT |
| P233FR9_H10_v29 | 122 | LPAPKNLVVSRVTEDSARLSWTAPDAAFDSFAIGYWE WDDDGEAIVLTVPGSCRSYDLTGLKPGTEYPVYIAGV KGGQFSFPLSAIFTT |
| P233FR9_H10_v30 | 123 | LPAPKNLVVSRVTEDSARLSWTAPDAAFDSFAIGYWE WDDDGEAIVLTVPGSCRSYDLTGLKPGTEYPVYIAGV KGGQLSFPLSAIFTT |
| P233FR9P1001-H3-1_v1 | 124 | LPAPKNLVVSRVTEDSARLSWTAPDAAFDSFRIGYWE WDDDGEAIVLTVPGSCRSYDLTGLKPGTEYHVYIAGV KGGQWSFPLSAIFTT |
| P233FR9P1001-H3-1_v2 | 125 | LPAPKNLVVSRVTEDSARLSWTAPDAAFDSFKIGYWE WDDDGEAIVLTVPGSCRSYDLTGLKPGTEYHVYIAGV KGGQWSFPLSAIFTT |
| P233FR9P1001-H3-1_v3 | 126 | LPAPKNLVVSRVTEDSARLSWTAPDAAFDSFEIGYWE WDDDGEAIVLTVPGSCRSYDLTGLKPGTEYHVYIAGV KGGQWSFPLSAIFTT |
| P233FR9P1001-H3-1_v4 | 127 | LPAPKNLVVSRVTEDSARLSWTAPDAAFDSFHIGYWE WDDDGEAIVLTVPGSCRSYDLTGLKPGTEYHVYIAGV KGGQWSFPLSAIFTT |
| P233FR9P1001-H3-1_v5 | 128 | LPAPKNLVVSRVTEDSARLSWTAPDAAFDSFDIGYWE WDDDGEAIVLTVPGSCRSYDLTGLKPGTEYHVYIAGV KGGQWSFPLSAIFTT |

-continued

TABLE 13 shows the amino acid sequences of the generated molecules.

| Clone ID | SEQ ID NO: | Sequence |
|---|---|---|
| P233FR9P1001-H3-1_v6 | 129 | LPAPKNLVVSRVTEDSARLSWTAPDAAFDSFAIGYWE WDDDGEAIVLTVPGSCRSYDLTGLKPGTEYHVYIAGV KGGQWSFPLSAIFTT |
| P233FR9P1001-H3-1_v7 | 130 | LPAPKNLVVSRVTEDSARLSWTAPDAAFDSFGIGYWE WDDDGEAIVLTVPGSCRSYDLTGLKPGTEYHVYIAGV KGGQWSFPLSAIFTT |
| P233FR9P1001-H3-1_v8 | 131 | LPAPKNLVVSRVTEDSARLSWTAPDAAFDSFVIGYWE WDDDGEAIVLTVPGSCRSYDLTGLKPGTEYHVYIAGV KGGQWSFPLSAIFTT |
| P233FR9P1001-H3-1_v9 | 132 | LPAPKNLVVSRVTEDSARLSWTAPDAAFDSFLIGYWE WDDDGEAIVLTVPGSCRSYDLTGLKPGTEYHVYIAGV KGGQWSFPLSAIFTT |
| P233FR9P1001-H3-1_v10 | 133 | LPAPKNLVVSRVTEDSARLSWTAPDAAFDSFIIGYWE WDDDGEAIVLTVPGSCRSYDLTGLKPGTEYHVYIAGV KGGQWSFPLSAIFTT |
| P233FR9P1001-H3-1_v11 | 134 | LPAPKNLVVSRVTEDSARLSWTAPDAAFDSFFIGYWE WDDDGEAIVLTVPGSCRSYDLTGLKPGTEYHVYIAGV KGGQWSFPLSAIFTT |
| P233FR9P1001-H3-1_v12 | 135 | LPAPKNLVVSRVTEDSARLSWTAPDAAFDSFWIGYWE WDDDGEAIVLTVPGSCRSYDLTGLKPGTEYHVYIAGV KGGQWSFPLSAIFTT |
| P233FR9P1001-H3-1_v13 | 136 | LPAPKNLVVSRVTEDSARLSWTAPDAAFDSFNIGYWE WDDDGEAIVLTVPGSCRSYDLTGLKPGTEYHVYIAGV KGGQWSFPLSAIFTT |
| P233FR9P1001-H3-1_v14 | 137 | LPAPKNLVVSRVTEDSARLSWTAPDAAFDSFQIGYWE WDDDGEAIVLTVPGSCRSYDLTGLKPGTEYHVYIAGV KGGQWSFPLSAIFTT |
| P233FR9P1001-H3-1_v15 | 138 | LPAPKNLVVSRVTEDSARLSWTAPDAAFDSFSIGYWE WDDDGEAIVLTVPGSCRSYDLTGLKPGTEYHVYIAGV KGGQWSFPLSAIFTT |
| P233FR9P1001-H3-1_v16 | 139 | LPAPKNLVVSRVTEDSARLSWTAPDAAFDSFTIGYWE WDDDGEAIVLTVPGSCRSYDLTGLKPGTEYHVYIAGV KGGQWSFPLSAIFTT |
| P233FR9P1001-H3-1_v17 | 140 | LPAPKNLVVSRVTEDSARLSWTAPDAAFDSFYIGYWE WDDDGEAIVLTVPGSCRSYDLTGLKPGTEYHVYIAGV KGGQWSFPLSAIFTT |

Example 9

Detection of PSMA Expression on Tumor Cells Using Anti PSMA Centyrin Conjugated to Fluorescent Dye This example shows the detection of PSMA present on cells with anti-PSMA Centyrin™ conjugated to a fluorescent dye. C-terminally His-tagged anti-PSMA Centyrin™ P233FR9_H10 (SEQ ID NO: 49) with a free cysteine at amino acid 53 was conjugated to R-phycoerythrin (PE) (Prozyme® catalog #PB31). The PE was activated using sulfo-SMCC (Pierce™ catalog #22122) for 60 min, and activated PE was separated from free sulfo-SMCC by gel-filtration chromatography using Sephadex® G25 (a gel-filtration resin) and PBS/EDTA buffer. The Centyrin™ was reduced using TCEP (Sigma, cat. #646547) for 30 min. The reduced Centyrin™ was separated from free TCEP by gel-filtration chromatography using Sephadex® G25 and PBS/EDTA buffer. The activated R-PE was covalently coupled to the reduced Centyrin™ for 90 min followed by quenching with N-Ethylmaleimide (Sigma catalog #04260) for 20 min. The "PE-conjugated Centyrin™" was purified by size-exclusion chromatography (SEC) using a Tosoh® TSKgel® G3000SW liquid chromatography column in 100 mM sodium phosphate, 100 mM sodium sulfate, 0.05% sodium azide, pH 6.5 on an AKTA explorer FPLC (General Electric™).

The PE-conjugated Centyrin™ was tested for sensitivity and specificity using PSMA positive and negative cell lines by flow cytometry and CELLSEARCH® Circulating Tumor Cell (CTC) assay. The following prostate cell lines were purchased from ATCC® and used to validate the specificity of the anti-PSMA Centyrin™: LNCaP (high PSMA expression), 22Rv1 (low PSMA expression) and PC3 (no PSMA expression).

Detection of PSMA on Cell Lines by Flow Cytometry

Figure 6:
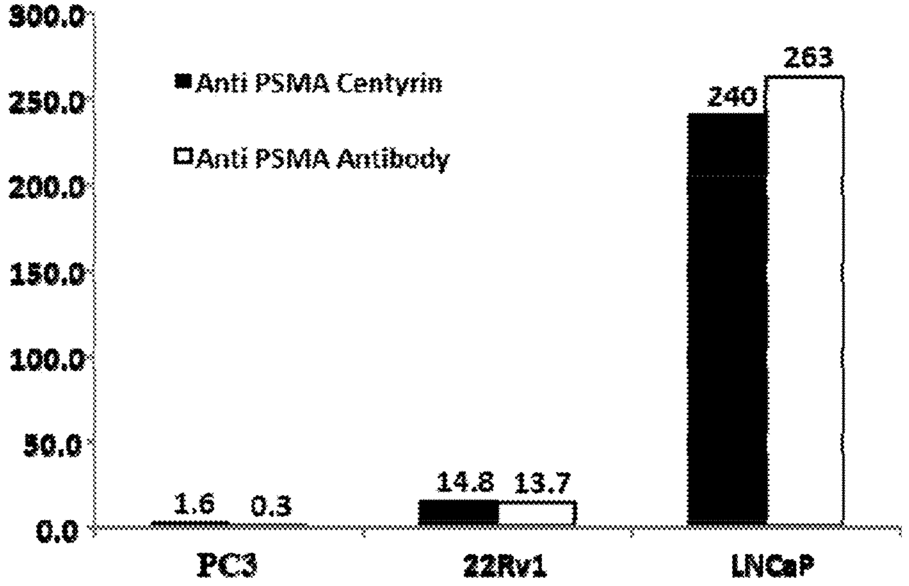
FIG. 6 shows the comparison of mean fluorescence intensity (MFI) of different tumor cell lines stained with anti PSMA centyrin-PE (black) and anti PSMA antibody-PE (white).

Prostate cell lines were harvested using standard cell culture procedures. The cells (~30,000) were stained in 0.1 mL of PBS containing 1% bovine serum albumin (BSA) with PE-conjugated Centyrin™ for 20 minutes. PE-conjugated anti-PSMA antibody from BioLegend® (clone LNI-17 catalog #342504) was used as a positive control. After the incubation, 3 mL of PBS/BSA buffer was added and unbound PE conjugate was removed by centrifugation at 800 g for 5 minutes. The supernatant was aspirated and the cells were resuspended in 0.3 mL of PBS/BSA. The samples were analyzed by BD FACSCalibur™ clinical cell analyzer. The mean fluorescent intensity (MFI) of PSMA staining from each cell line was determined and compared to MFI with anti-PSMA antibody. The MFI is directly related to PSMA expression level with higher MFI from high PSMA expressing cell line. FIG. 6 shows the MFI values from different cell lines detected with PE-conjugated Centyrin™ in comparison to MFI values with PE-conjugated anti-PSMA antibody.

The results show that a PE-conjugated Centyrin binds to PSMA positive cell lines and does not bind nonspecifically to PSMA negative cells. The MFI is higher with high PSMA expressing cell line (LNCaP) compared to low MFI with low PSMA expressing cell line (22Rv1) as expected. The MFI with PSMA negative cell line (PC3) is close to the background signal. In addition, the performance of PE-conjugated Centyrin E in binding to different cell lines is similar to anti-PSMA antibody-PE, as similar MFI values were obtained with both centyrin and antibody conjugates. This example shows that PE-conjugated Centyrin shows sensitivity and specificity in the detection of PSMA on tumor cells.

Detection of PSMA by Circulating Tumor Cell Assay

The above results were further confirmed by testing PE-conjugated Centyrin™ via a CELLSEARCH® assay to detect and enumerate circulating tumor cells (CTCs) from 7.5 mL of blood. Circulating tumor cell enumeration using the CELLSEARCH® (Veridex™ LLC, Raritan, N.J., USA) was carried out according to the manufacturer's protocol and training. The CELLSEARCH® assay uses anti-EpCAM conjugated to ferrofluid magnetic particles to capture and anti-cytokeratin specific to cytokeratins 8, 18 and 19 conjugated to fluorescein to visualize CTCs. The CELLSEARCH® assay uses CELLTRACKS® AUTOPREP® for sample preparation and CELLTRACKS® ANALYZER II® (CTA II) for the analysis. The CTA II is a four color semi-automated fluorescent microscope and uses 3 colors to identify and enumerate CTCs. The fourth color on CTA II is available to phenotype CTCs with additional markers of interest. In this example, tissue cultured tumor cells were spiked into normal blood to mimic CTCs in blood. Approximately 500 tumor cells (LNCaP, 22Rv1, PC3-9 or SKBR3 cells) were spiked into 7.5 mL of normal donor blood collected in a CELLSAVE Preservation Tube™ (Janssen Diagnostics). The breast cancer cell line (SKBR3) was also used as PSMA negative cell line. The samples were processed on the AUTOPREP® using CELLSEARCH® CXC kit and PE-conjugated Centyrin™ as a marker. The AUTOPREP® sample preparation system enriches tumor cells by capturing tumor cells using anti-EpCAM ferrofluid. The CTC enriched samples were stained with a nucleic acid dye (DAPI) to identify nucleated cells, anti-cytokeratin antibody conjugated to fluorescein isothiocyanate (FITC) to identify tumor cells, and anti-leukocyte antibody conjugated to allophycocyanin (APC) to identify leukocytes. The sample was processed to a final volume of 0.32 ml, and was transferred to a sample chamber while inside the MagNest® cell presentation device. The MagNest® device presents the magnetically labeled cells for analysis by the CELLTRACKS® ANALYZER II®. The samples were analyzed using CTA II to enumerate CTCs and detect PSMA on CTCs. The analyzer automatically analyzes samples and presents candidate tumor cells which are positive for DAPI and cytokeratin as thumbnail images for the review. The results from tumor cells stained with PE-conjugated Centyrin™ in CELLSEARCH® assay are shown in FIG. 7. The images show CTCs stained with the PE-conjugated Centyrin™ in the columns labeled PSMA-PE.

Figure 7A:
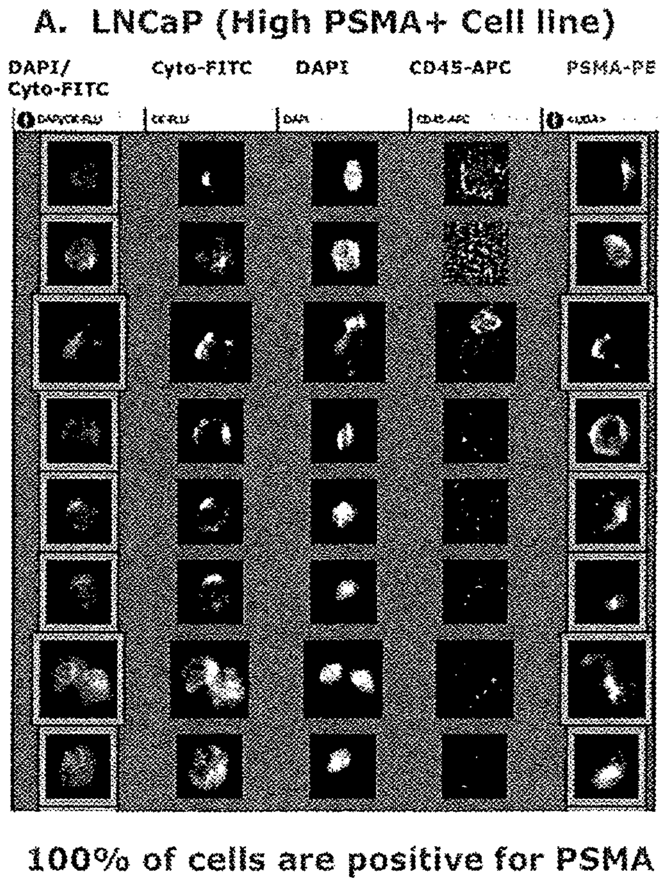
FIG. 7A shows a series of the CELLTRACKS ANALYZER II® fluorescence analyzer) browser images of LNCaP cells stained with DAPI, anti-cytokeratin-FITC, anti-CD45-APC and anti-PSMA Centyrin™ (FN3 domain polypeptide)-PE. The thumbnail images show, from right to left, PSMA-PE staining, CD45-APC signal, DAPI stained nuclei, Cytokeratin-FITC reactivity, and finally an overlay of the Cytokeratin-FITC & DAPI staining. A cell must have a nucleus, express cytokeratin and be negative for CD45 to be counted as a CTC. The CTC must have a positive signal for PSMA to be scored as PSMA positive CTC.
Figure 7B:
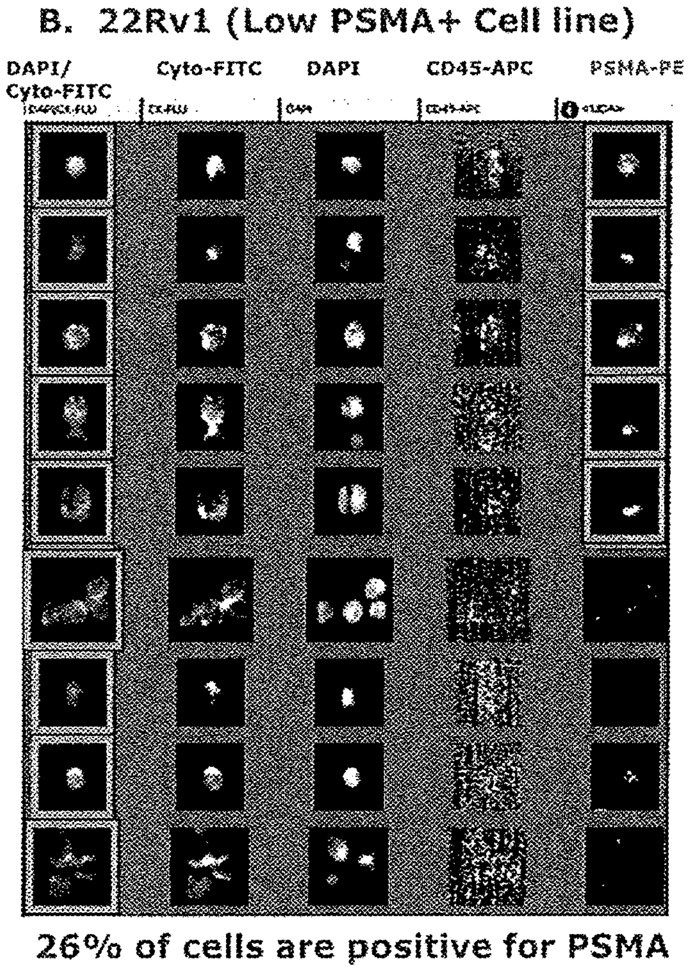
FIG. 7B shows a series of the CELLTRACKS ANALYZER II® (fluorescence analyzer) browser images of 22Rv1 cells stained with DAPI, anti-cytokeratin-FITC, anti-CD45-APC and anti-PSMA Centyrin™-PE The thumbnail images show, from right to left, PSMA-PE staining, CD45-APC signal, DAPI stained nuclei, Cytokeratin-FITC reactivity, and finally an overlay of the Cytokeratin-FITC & DAPI staining. A cell must have a nucleus, express cytokeratin and be negative for CD45 to be counted as a CTC. The CTC must have a positive signal for PSMA to be scored as PSMA positive CTC.
Figure 7C:
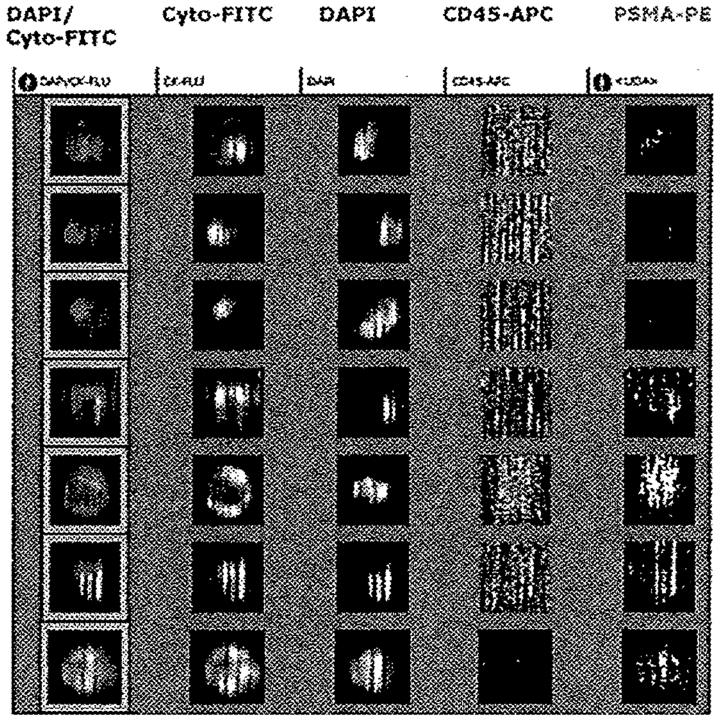
FIG. 7C shows a series of the CELLTRACKS ANALYZER II® (fluorescence analyzer) browser images of PC3 cells stained with DAPI, anti-cytokeratin-FITC, anti-CD45-APC anti-CD45-APC and anti PSMA centyrin-PE anti-PSMA Centyrin™-PE. The thumbnail images show, from right to left, PSMA-PE staining, CD45-APC signal, DAPI stained nuclei, Cytokeratin-FITC reactivity, and finally an overlay of the Cytokeratin-FITC & DAPI staining. A cell must have a nucleus, express cytokeratin and be negative for CD45 to be counted as a CTC. The CTC must have a positive signal for PSMA to be scored as PSMA positive CTC.
Figure 7D:
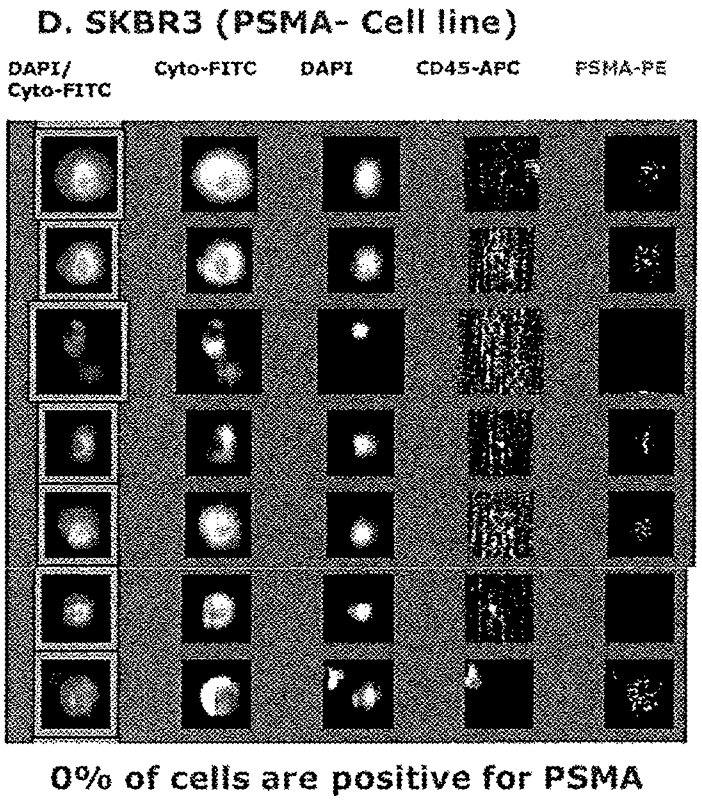
FIG. 7D shows a series of the CELLTRACKS ANALYZER II® (fluorescence analyzer) browser images of SKBR3 cells stained with DAPI, anti-cytokeratin-FITC, anti-CD45-APC and anti-PSMA Centyrin™-PE. The thumbnail images show, from right to left, PSMA-PE staining, CD45-APC signal, DAPI stained nuclei, Cytokeratin-FITC reactivity, and finally an overlay of the Cytokeratin-FITC & DAPI staining. A cell must have a nucleus, express cytokeratin and be negative for CD45 to be counted as a CTC. The CTC must have a positive signal for PSMA to be scored as PSMA positive CTC.

FIG. 7A shows the expression of PSMA on LNCaP tumor cells and 100% of these cells are positive for PSMA. Low PSMA expressing cell line (22Rv1) is 26% positive for PSMA (FIG. 7B). On the other hand, PSMA negative cell lines (PC3-9 and SKBR3) are negative for PSMA (FIGS. 7C and 7D). These results are consistent with flow cytometry results. This example shows that anti PSMA centyrin can be used to detect PSMA expression on CTCs and further confirms the sensitivity and specificity of anti PSMA centyrin.

Sequences

SEQ ID No. 1 = Original Tencon Sequence
LPAPKNLVVSEVTEDSLRLSWTAPDAAFDSFLIQYQESEKVGEAINLTVPGSERSYDLTGLKPGTEYTVSIY

GVKGGHRSNPLSAEFTT

SEQ ID No. 2 = TCL1 library
LPAPKNLVVSEVTEDSLRLSWTAPDAAFDSFLIQYQESEKVGEAINLTVPGSERSYDLTGLKPGTEYTVSIY GV(X)$_{7-12}$PLSAEFTT;
wherein $X_1$, $X_2$, $X_3$, $X_4$, $X_5$, $X_6$, $X_7$ is any amino acid; and $X_8$, $X_9$, $X_{10}$, $X_{11}$ and $X_{12}$ are any amino acid or deleted SEQ ID No. 3 = TCL2 library
LPAPKNLVVSEVTEDSLRLSW$X_1X_2X_3X_4X_5X_6X_7X_8$SFLIQYQESEKVGEAINLTVPGSERSYDLTGLKPGTEY TVSIYGV$X_9X_{10}X_{11}A_{12}X_{13}$S$X_{14}X_{15}$LSAEFTT;
wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

-continued $X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

SEQ ID No. 4 = Stabilized Tencon
LPAPKNLVVSRVTEDSARLSWTAPDAAFDSFLIQYQESEKVGEAIVLTVPGSERSYDLTGLKPGTEYTVSIY

GVKGGHRSNPLSAIFTT

SEQ ID No. 5 = TCL7 (FG and BC loops)
LPAPKNLVVSRVTEDSARLSW$X_1X_2X_3X_4X_5X_6X_7X_8X_9$FDSFLIQYQESEKVGEAIVLTVPGSERSYDLTGLKPG TEYTVSIYGV$X_{10}X_{11}X_{12}X_{13}X_{14}X_{15}X_{16}X_{17}X_{18}X_{19}$SNPLSAIFTT;
wherein $X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ are A, D, E, F, G, H, I, K, L, N, P, Q, R, S, T, V, W or Y;
and $X_7$, $X_8$, $X_9$, $X_{17}$, $X_{18}$ and $X_{19}$, are A, D, E, F, G, H, I, K, L, N, P, Q, R, S, T, V, W, Y or deleted SEQ ID No. 6 = TCL9 (FG loop)
LPAPKNLVVSRVTEDSARLSWTAPDAAFDSFLIQYQESEKVGEAIVLTVPGSERSYDLTGLKPGTEYTVSIY GV $X_1X_2X_3X_4X_5X_6X_7X_8X_9X_{10}X_{11}X_{12}$SNPLSAIFTT;
wherein $X_1$, $X_2$, $X_3$, $X_4$, $X_5$, $X_6$ and $X_7$, is A, D, E, F, G, H, I, K, L, N, P, Q, R, S, T, V, W or Y; and $X_8$, $X_9$, $X_{10}$, $X_{11}$ and $X_{12}$ is A, D, E, F, G, H, I, K, L, N, P, Q, R, S, T, V, W, Y or deleted.

TCL14 library (SEQ ID NO: 7):
LPAPKNLVVSRVTEDSARLSWTAPDAAFDSF$X_1$I$X_2$Y$X_3$E$X_4X_5X_6X_7$GEAIVLTVPGSERSYDLTGLKPGTEY$X_8$ V$X_9$I$X_{10}$GVKGG$X_{11}X_{12}$S$X_{13}$PLSAIFTT;
wherein $X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D, E, F, G, H, I, K, L, N, P, Q, R, S, T, V, W,Y, C or M.

TCL24 Library (SEQ ID NO: 8)
LPAPKNLVVSRVTEDSARLSWTAPDAAFDSF$X_1$I$X_2$Y$X_3$E$X_4X_5X_6X_7$GEAI$X_8$L$X_9$VPGSERSYDLTGLKPGTEY $X_{10}$V$X_{11}$I$X_{12}$GVKGG$X_{13}X_{14}$S$X_{15}$PL$X_{16}$A$X_{17}$FTT;
wherein $X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$ are A, D, E, F, G, H, I, K, L, N, P, Q, R, S, T, V, Y or W.

SEQ ID No. 9 = Sloning-FOR
GTGACACGGCGGTTAGAAC

SEQ ID No. 10 = Sloning-REV
GCCTTTGGGAAGCTTCTAAG

-continued

SEQ ID No. 11 = POP2250
CGGCGGTTAGAACGCGGCTACAATTAATAC

SEQ ID No. 12 = DigLigRev
CATGATTACGCCAAGCTCAGAA

SEQ ID No. 13 = BC9
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTGAAGTTACCGAAGACTCTCTGCGTCTGTCTTGGNNNNNNN

NNNNNNNNNNNNNNNNNNNNTTYGACTCTTTCCTGATCCAGTACCAGGAATCTGAAAAAGTTGGTGA

AGCGATCAACCTGACCGTTCCGGGTTCTGAACGTTCTTACGACCTGACCGGTCTGAAACCGGGTACCG

AATACACCGTTTCTATCTACGGTGTTCTTAGAAGCTTCCCAAAGGC

SEQ ID No. 14 = BC8
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTGAAGTTACCGAAGACTCTCTGCGTCTGTCTTGGNNNNNNN

NNNNNNNNNNNNNNNNNTTYGACTCTTTCCTGATCCAGTACCAGGAATCTGAAAAAGTTGGTGAAGC

GATCAACCTGACCGTTCCGGGTTCTGAACGTTCTTACGACCTGACCGGTCTGAAACCGGGTACCGAAT

ACACCGTTTCTATCTACGGTGTTCTTAGAAGCTTCCCAAAGGC

SEQ ID No. 15 = BC7
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTGAAGTTACCGAAGACTCTCTGCGTCTGTCTTGGNNNNNNN

NNNNNNNNNNNNNNTTYGACTCTTTCCTGATCCAGTACCAGGAATCTGAAAAAGTTGGTGAAGCGAT

CAACCTGACCGTTCCGGGTTCTGAACGTTCTTACGACCTGACCGGTCTGAAACCGGGTACCGAATACA

CCGTTTCTATCTACGGTGTTCTTAGAAGCTTCCCAAAGGC

SEQ ID No. 16 = BC6
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTGAAGTTACCGAAGACTCTCTGCGTCTGTCTTGGNNNNNNN

NNNNNNNNNNNTTYGACTCTTTCCTGATCCAGTACCAGGAATCTGAAAAAGTTGGTGAAGCGATCAAC

CTGACCGTTCCGGGTTCTGAACGTTCTTACGACCTGACCGGTCTGAAACCGGGTACCGAATACACCGTT

TCTATCTACGGTGTTCTTAGAAGCTTCCCAAAGGC

SEQ ID No. 17 = 130mer-L17A
CGGCGGTTAGAACGCGGCTACAATTAATACATAACCCCATCCCCCTGTTGACAATTAATCATCGGCTC

GTATAATGTGTGGAATTGTGAGCGGATAACAATTTCACACAGGAAACAGGATCTACCATGCTG

SEQ ID No. 18 = POP222ext
CGG CGG TTA GAA CGC GGC TAC AAT TAA TAC

SEQ ID No. 19 = LS1114
CCA AGA CAG ACG GGC AGA GTC TTC GGT AAC GCG AGA AAC AAC CAG GTT TTT CGG CGC CGG

CAG CAT GGT AGA TCC TGT TTC

SEQ ID No. 20 = LS1115
CCG AAG ACT CTG CCC GTC TGT CTT GG

SEQ ID No. 21 = LS1117
CAG TGG TCT CAC GGA TTC CTG GTA CTG GAT CAG GAA AGA GTC GAA

SEQ ID No. 22 = SDG10
CATGCGGTCTCTTCCGAAAAAGTTGGTGAAGCGATCGTCCTGACCGTTCCGGGT

-continued

SEQ ID No. 23 = SDG24
GGTGGTGAAGATCGCAGACAGCGGGTTAG

SEQ ID No. 24 = POP2222
CGGCGGTTAGAACGCGGCTAC

SEQ ID No. 25 = SDG28
AAGATCAGTTGCGGCCGCTAGACTAGAACCGCTGCCACCGCCGGTGGTGAAGATCGCAGAC

SEQ ID No. 26 = FG12
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTCGCGTTACCGAAGACTCTGCGCGTCTGTCTTGGACCGCGCC

GGACGCGGCGTTCGACTCTTTCCTGATCCAGTACCAGGAATCTGAAAAAGTTGGTGAAGCGATCGTGC

TGACCGTTCCGGGTTCTGAACGTTCTTACGACCTGACCGGTCTGAAACCGGGTACCGAATACACCGTTT

CTATCTACGGTGTTNNNNNNNNNNNNNNNNNNNNNNNNNNNNNNNNNNNNTCTAACCCGCTGTCTGC

GATCTTCACCACCGGCGGTCACCATCACCATCACCATGGCAGCGGTTCTAGTCTAGCGGCCGCAACTG

ATCTTGGC

SEQ ID No. 27 = FG11
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTCGCGTTACCGAAGACTCTGCGCGTCTGTCTTGGACCGCGCC

GGACGCGGCGTTCGACTCTTTCCTGATCCAGTACCAGGAATCTGAAAAAGTTGGTGAAGCGATCGTGC

TGACCGTTCCGGGTTCTGAACGTTCTTACGACCTGACCGGTCTGAAACCGGGTACCGAATACACCGTTT

CTATCTACGGTGTTNNNNNNNNNNNNNNNNNNNNNNNNNNNNNNNNNTCTAACCCGCTGTCTGCGAT

CTTCACCACCGGCGGTCACCATCACCATCACCATGGCAGCGGTTCTAGTCTAGCGGCCGCAACTGATC

TTGGC

SEQ ID No. 28 = FG10
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTCGCGTTACCGAAGACTCTGCGCGTCTGTCTTGGACCGCGCC

GGACGCGGCGTTCGACTCTTTCCTGATCCAGTACCAGGAATCTGAAAAAGTTGGTGAAGCGATCGTGC

TGACCGTTCCGGGTTCTGAACGTTCTTACGACCTGACCGGTCTGAAACCGGGTACCGAATACACCGTTT

CTATCTACGGTGTTNNNNNNNNNNNNNNNNNNNNNNNNNNNNNNTCTAACCCGCTGTCTGCGATCTT

CACCACCGGCGGTCACCATCACCATCACCATGGCAGCGGTTCTAGTCTAGCGGCCGCAACTGATCTTG

GC

SEQ ID No. 29 = FG9
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTCGCGTTACCGAAGACTCTGCGCGTCTGTCTTGGACCGCGCC

GGACGCGGCGTTCGACTCTTTCCTGATCCAGTACCAGGAATCTGAAAAAGTTGGTGAAGCGATCGTGC

TGACCGTTCCGGGTTCTGAACGTTCTTACGACCTGACCGGTCTGAAACCGGGTACCGAATACACCGTTT

CTATCTACGGTGTTNNNNNNNNNNNNNNNNNNNNNNNNNNNTCTAACCCGCTGTCTGCGATCTTCACC

ACCGGCGGTCACCATCACCATCACCATGGCAGCGGTTCTAGTCTAGCGGCCGCAACTGATCTTG

GC

SEQ ID No. 30 = FG8
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

-continued

GCCGGCGCCGAAAAACCTGGTTGTTTCTCGCGTTACCGAAGACTCTGCGCGTCTGTCTTGGACCGCGCC

GGACGCGGCGTTCGACTCTTTCCTGATCCAGTACCAGGAATCTGAAAAAGTTGGTGAAGCGATCGTGC

TGACCGTTCCGGGTTCTGAACGTTCTTACGACCTGACCGGTCTGAAACCGGGTACCGAATACACCGTTT

CTATCTACGGTGTTNNNNNNNNNNNNNNNNNNNNNNNNNNTCTAACCCGCTGTCTGCGATCTTCACCACC

GGCGGTCACCATCACCATCACCATGGCAGCGGTTCTAGTCTAGCGGCCGCAACTGATCTTGGC

SEQ ID No. 31 = FG7
GTGACACGGCGGTTAGAACGCGGCTACAATTAATACATAACCCCATCCCCCTGTTGACAATTAATCAT

CGGCTCGTATAATGTGTGGAATTGTGAGCGGATAACAATTTCACACAGGAAACAGGATCTACCATGCT

GCCGGCGCCGAAAAACCTGGTTGTTTCTCGCGTTACCGAAGACTCTGCGCGTCTGTCTTGGACCGCGCC

GGACGCGGCGTTCGACTCTTTCCTGATCCAGTACCAGGAATCTGAAAAAGTTGGTGAAGCGATCGTGC

TGACCGTTCCGGGTTCTGAACGTTCTTACGACCTGACCGGTCTGAAACCGGGTACCGAATACACCGTTT

CTATCTACGGTGTTNNNNNNNNNNNNNNNNNNNNNNNTCTAACCCGCTGTCTGCGATCTTCACCACCGGC

GGTCACCATCACCATCACCATGGCAGCGGTTCTAGTCTAGCGGCCGCAACTGATCTTGGC

SEQ ID No. 32 = PSMW1 (N'-AviTag-HisTag-GS-Cyno PSMA_ECD)
KSSSEATNITPKHNMKAFLDELKAENIKKFLHNFTQIPHLAGTEQNFQLAKQIQSQWKEFGLDSVELTHYD

VLLSYPNKTHPNYISIINEDGNEIFNTSLFEPPPAGYENVSDIVPPFSAFSPQGMPEGDLVYVNYARIEDFFKL

ERDMKINCSGKIVIARYGKVFRGNKVKNAQLAGATGVILYSDPDDYFAPGVKSYPDGWNLPGGGVQRGNI

LNLNGAGDPLTPGYPANEYAYRRGMAEAVGLPSIPVHPIGYYDAQKLLEKMGGSASPDSSWRGSLKVPYN

VGPGFTGNFSTQKVKMHIHSTSEVTRIYNVIGTLRGAVEPDRYVILGGHRDSWVFGGIDPQSGAAVVHEIV

RSFGMLKKEGWRPRRTILFASWDAEEFGLLGSTEWAEENSRLLQERGVAYINADSSIEGNYTLRVDCTPLM

YSLVYNLTKELESPDEGFEGKSLYESWTKKSPSPEFSGMPRISKLGSGNDFEVFFQRLGIASGRARYTKNWE

TNKFSSYPLYHSVYETYELVEKFYDPMFKYHLTVAQVRGGMVFELANSVVLPFDCRDYAVVLRKYADKI

YNISMKHPQEMKTYSVSFDSLFSAVKNFIEIASKFSERLRDFDKSNPILLRMMNDQLMFLERAFIDPLGLPD

RPFYRHVIYAPSSHNKYAGESFPGIYDALFDIESKVDPSQAWGEVKRQISIATFTVQAAAETLSEVA

SEQ ID No. 33 = PSMW8 (N'-AviTag-HisTag-GS-Chimp PSMA_ECD)
KSSNEATNITPKHNMKAFLDELKAENIKKFLYNFTQIPHLAGTEQNFQLAKQIQSQWKEFGLDSVELAHYD

VLLSYPNKTHPNYISIINEDGNEIFNTSLFEPPPPGYENVLDIVPPFSAFSPQGMPEGDLVYVNYARTEDFFKL

ERDMKINCSGKIVIARYGKVFRGNKVKNAQLAGAKGVILYSDPADYFAPGVKSYPDGWNLPGGGVQRGNI

LNLNGAGDPLTPGYPANEYAYRHGIAEAVGLPSIPVHPIGYYDAQKLLEKMGGSAPPDSSWRGSLKVPYN

VGPGFTGNFSTQKVKMHIHSTNEVTRIYNVIGTLRGAVEPDRYVILGGHRDSWVFGGIDPQSGAAVVHEIV

RSFGTLKKEGWRPRRTILFASWDAEEFGLLGSTEWAEENSRLLQERGVAYINADSSIEGNYTLRVDCTPLM

YSLVYNLTKELKSPDEGFEGKSLYESWTKKSPSPEFSGMPRISKLGSGNDFEVFFQRLGIASGRARYTKNWE

TNKFSGYPLYHSVYETYELVEKFYDPMFKYHLTVAQVRGGMVFELANSIVLPFDCRDYAVVLRKYADKIY

NISMKHPQEMKTYSVSFDSLFSAVKNFIEIASKFTERLQDFDKSNPILLRMMNDQLMFLERAFIDPLGLPDR

PFYRHVIYAPSSHNKYAGESFPGIYDALFDIESKVDPSKAWGDVKRQISVAAFTVQAAAETLSEVA

SEQ ID NO: 34: hexahistidine tag
HHHHHH

SEQ ID No. 35 = P258AR6P1071_G03
LPAPKNLVVSRVTEDSARLSWDIDEQRDWFDSFLIQYQESEKVGEAIVLTVPGSERSYDLTGLKPGIEYTVS

IYGVYHVYRSNPLSAIFTT

SEQ ID No. 36 = P258AR6P1070_A05
LPAPKNLVVSRVTEDSARLSWTIDEQRDWFDSFLIQYQESEKVGEAIVLTVPGSERSYDLTGLKPGIEYTVS

IYGVYHVYRSNPLSAIFTT

-continued

SEQ ID No. 37 = P258AR6P1071_F04
LPAPKNLVVSRVTEDSARLSWVIDEQRDWFDSFLIQYQESEKVGEAIVLTVPGSERSYDLTGLKPGIEYTVS

IYGVYHVYRSNPLSAIFTT

SEQ ID No. 38 = P258AR6P1070_F09
LPAPKNLVVSRVTEDSARLSWTIDEQRDWFESFLIQYQESEKVGEAIVLTVPGSERSYDLTGLKPGTEYTVSI

YGVYHVYRSNPLSAIFTT

SEQ ID No. 39 = P258AR6P1071_D02
LPAPKNLVVSRVTEDSARLSWAIDEQRDWFESFLIQYQESEKVGEAIVLTVPGSERSYDLTGLKPGTEYTVS

IYGVYHVYRSNPLSAIFTT

SEQ ID No. 40 = P229CR5P819_H11
LPAPKNLVVSRVTEDSARLSWDIDEQRDWFDSFLIQYQESEKVGEAIVLTVPGSERSYDLTGLKPGIEYTVS

IYGVYHVYRS SNPL SAIFTT

SEQ ID No. 41 = P233FR9_H10
LPAPKNLVVSRVTEDSARLSWTAPDAAFDSFAIGYWEWDDDGEAIVLTVPGSERSYDLTGLKPGTEYPVYI

AGVKGGQWSFPLSAIFTT

SEQ ID No. 42 = P233FR9P1001_B5-5
LPAPKNLVVSRVTEDSARLSWTAPDAAFDSFTIGYWEWDDDGEAIVLTVPGSERSYDLTGLKPGTEYPVYI

AGVKGGQWSFPLSAIFTT

SEQ ID No. 43 = P233FR9P1001_H3-1
LPAPKNLVVSRVTEDSARLSWTAPDAAFDSFPIGYWEWDDDGEAIVLTVPGSERSYDLTGLKPGTEYHVYI

AGVKGGQWSFPLSAIFTT

SEQ ID No. 44 = P233FR9P1001_D9
LPAPKNLVVSRVTEDSARLSWTAPDAAFDSFPIGYWEWDDDGEAIVLTVPGSERSYDLTGLKPGTEYWVYI

AGVKGGQWSFPLSAIFTT

SEQ ID No. 45 = P234CR9_A07
LPAPKNLVVSRVTEDSARLSWGEQFTIFDSFLIQYQESEKVGEAIVLTVPGSERSYDLTGLKPG1EYTVSIYG

ASGYEWFHAFGSSNPLSAIFTT

SEQ ID No. 46 = P234CR9_H01
LPAPKNLVVSRVTEDSARLSWEWWVIPGDFDSFLIQYQESEKVGEAIVLTVPGSERSYDLTGLKPGTEYTVS

IYGVVNSGQWNDTSNPLSAIFTT

SEQ ID No. 47 = P233FR9_H10 (cterm cys)
LPAPKNLVVSRVTEDSARLSWTAPDAAFDSFAIGYWEWDDDGEAIVLTVPGSERSYDLTGLKPGTEYPVYI

AGVKGGQWSFPLSAIFTTC

SEQ ID No. 48 = P233FR9_H10 (K62C)
LPAPKNLVVSRVTEDSARLSWTAPDAAFDSFAIGYWEWDDDGEAIVLTVPGSERSYDLTGLCPGTEYPVYI

AGVKGGQWSFPLSAIFTT

SEQ ID No. 49 = P233FR9_H10 (E53C)
LPAPKNLVVSRVTEDSARLSWTAPDAAFDSFAIGYWEWDDDGEAIVLTVPGSCRSYDLTGLKPGTEYPVYI

AGVKGGQWSFPLSAIFTT

SEQ ID No. 50 = P233FR9_H10 (R11C)
LPAPKNLVVSCVTEDSARLSWTAPDAAFDSFAIGYWEWDDDGEAIVLTVPGSERSYDLTGLKPGTEYPVYI

AGVKGGQWSFPLSAIFTT

SEQ ID No. 51 = untargeted Centyrin (K62C)
LPAPKNLVVSEVTEDSARLSWTAPDAAFDSFLIQYQESEKVGEAIVLTVPGSERSYDLTGLCPGTEYTVSIY

GVKGGHRSNPLSAIFTTGGHHHHHH

SEQ ID No. 52 = Sortase A
MSHHHHHHSSGENLYFQSKPHIDNYLHDKDKDEKIEQYDKNVKEQASKDKKQQAKPQIPKDKSKVAGYIE

IPDADIKEPVYPGPATREQLNRGVSFAEENESLDDQNISIAGHTFIDRPNYQFTNLKAAKKGSMVYFKVGNE

TRKYKMTSIRNVKPTAVEVLDEQKGKDKQLTLITCDDYNEETGVWETRKIFVATEVK

-continued

SEQ ID No. 53 = tagless Sortase A
SKPHIDNYLHDKDKDEKIEQYDKNVKEQASKDKKQQAKPQIPKDKSKVAGYIEIPDADIKEPVYPGPATRE

QLNRGVSFAEENESLDDQNISIAGHTFIDRPNYQFTNLKAAKKGSMVYFKVGNETRKYKMTSIRNVKPTAV

EVLDEQKGKDKQLTLITCDDYNEETGVWETRKIFVATEVK

SEQ ID NO: 54 TEV protease cleavage site
ENLYFQS

SEQ ID NO: 55 FG loop of Tencon
KGGHRSN

SEQ ID NO: 56 BC loop
DIDEQRDW

SEQ iD nO: 57 BC loop
TIDEQRDW

SEQ iD NO: 58 BC loop
VIDEQRDW

SEQ ID NO: 59 BC loop
AIDEQRDW

SEQ ID NO: 60 BC loop
EWWVIPGD

SEQ ID NO: 61 BC loop
GEQFTI

SEQ ID NO: 62 BC loop
TAPDAA

SEQ ID NO: 63 C loop
FDSFLIQYQE

SEQ ID NO: 64 C loop
FESFLIQYQE

SEQ ID NO: 65 C loop
FDSFAIGYWE

SEQ ID NO: 66 C loop
FDSFPIGYWE

SEQ ID NO: 67 C loop
FDSFTIGYWE

SEQ ID NO: 68 CD loop
SEKVGE

SEQ ID NO: 69 CD loop
WDDDGE

SEQ ID NO: 70 F loop
TEYTVSIYGV

SEQ ID NO: 71 F loop
TEYTVSIYG

SEQ ID NO: 72 F loop
TEYPVYIAGV

SEQ ID NO: 73 F loop
TEYWVYIAGV

SEQ ID NO: 74 F loop
TEYHVYIAGV

SEQ ID NOs: 75-140 are above in the tables

SEQ ID NO: 141 full length cynoPSMA
MWNLLHETDSAVATARRPRWLCAGALVLAGGFFLLGFLFGWFIKSSSEATNITPKHNMKAFLDELKAENI

KKFLHNFTQIPHLAGTEQNFQLAKQIQSQWKEFGLDSVELTHYDVLLSYPNKTHPNYISIINEDGNEIFNTSL

FEPPPAGYENVSDIVPPFSAFSPQGMPEGDLVYVNYARTEDFFKLERDMKINCSGKIVIARYGKVFRGNKVK

NAQLAGATGVILYSDPDDYFAPGVKSYPDGWNLPGGGVQRGNILNLNGAGDPLTPGYPANEYAYRRGMA

-continued

EAVGLPSIPVHPIGYYDAQKLLEKMGGSASPDSSWRGSLKVPYNVGPGFTGNFSTQKVKMHIHSTSEVTRI

YNVIGTLRGAVEPDRYVILGGHRDSWVFGGIDPQSGAAVVHEIVRSFGMLKKEGWRPRRTILFASWDAEEF

GLLGSTEWAEENSRLLQERGVAYINADSSIEGNYTLRVDCTPLMYSLVYNLTKELESPDEGFEGKSLYESW

TKKSPSPEFSGMPRISKLGSGNDFEVFFQRLGIASGRARYTKNWETNKFSSYPLYHSVYETYELVEKFYDPM

FKYHLTVAQVRGGMVFELANSVVLPFDCRDYAVVLRKYADKIYNISMKHPQEMKTYSVSFDSLFSAVKNF

TEIASKFSERLRDFDKSNPILLRMMNDQLMFLERAFIDPLGLPDRPFYRHVIYAPSSHNKY

>142 linker
AEAAAKEAAAKEAAAKEAAAKEAAAKAAA

>143 human PSMA ECD
KSSNEATNITPKHNMKAFLDELKAENIKKFLYNFTQIPHLAGTEQNFQLAKQIQSQWKEFGLDSVELAHYD

VLLSYPNKTHPNYISTINEDGNEIFNTSLFEPPPPGYENVSDIVPPFSAFSPQGMPEGDLVYVNYART

EDFFKLERDMKINCSGKIVIARYGKVFRGNKVKNAQLAGAKGVILYSDPADYFAPGVKSYPDGW

NLPGGGVQRGNILNLNGAGDPLTPGYPANEYAYRRGIAEAVGLPSIPVHPIGYYDAQKLLEKMGG

SAPPDSSWRGSLKVPYNVGPGFTGNFSTQKVKMHIHSTNEVTRIYNVIGTLRGAVEPDRYVILGGH

RDSWVFGGIDPQSGAAVVHEIVRSFGTLKKEGWRPRRTILFASWDAEEFGLLGSTEWAEENSRLL

QERGVAYINADSSIEGNYTLRVDCTPLMYSLVHNLTKELKSPDEGFEGKSLYESWTKKSPSPEFSG

MPRISKLGSGNDFEVFFQRLGIASGRARYTKNWETNKFSGYPLYHSVYETYELVEKFYDPMFKYH

LTVAQVRGGMVFELANSIVLPFDCRDYAVVLRKYADKIYSISMKHPQEMKTYSVSFDSLFSAVKN

FTEIASKFSERLQDFDKSNPIVLRMMNDQLMFLERAFIDPLGLPDRPFYRHVIYAPSSHNKYAGESF

PGIYDALFDIESKVDPSKAWGEVKRQIYVAAFTVQAAAETLSEVA

>144 human FL PSMA with signal sequence
MWNLLHETDSAVATARRPRWLCAGALVLAGGFFLLGFLFGWFIKSSNEATNITPKHNMKAFLDELKAENI

KKFLYNFTQIPHLAGTEQNFQLAKQIQSQWKEFGLDSVELAHYDVLLSYPNKTHPNYISIINEDGNE

IFNTSLFEPPPPGYENVSDIVPPFSAFSPQGMPEGDLVYVNYARTEDFFKLERDMKINCSGKIVIARY

GKVFRGNKVKNAQLAGAKGVILYSDPADYFAPGVKSYPDGWNLPGGGVQRGNILNLNGAGDPL

TPGYPANEYAYRRGIAEAVGLPSIPVHPIGYYDAQKLLEKMGGSAPPDSSWRGSLKVPYNVGPGF

TGNFSTQKVKMHIHSTNEVTRIYNVIGTLRGAVEPDRYVILGGHRDSWVFGGIDPQSGAAVVHEIV

RSFGTLKKEGWRPRRTILFASWDAEEFGLLGSTEWAEENSRLLQERGVAYINADSSIEGNYTLRVD

CTPLMYSLVHNLTKELKSPDEGFEGKSLYESWTKKSPSPEFSGMPRISKLGSGNDFEVFFQRLGIAS

GRARYTKNWETNKFSGYPLYHSVYETYELVEKFYDPMFKYHLTVAQVRGGMVFELANSIVLPFD

CRDYAVVLRKYADKIYSISMKHPQEMKTYSVSFDSLFSAVKNFTEIASKFSERLQDFDKSNPIVLR

MMNDQLMFLERAFIDPLGLPDRPFYRHVIYAPSSHNKYAGESFPGIYDALFDIESKVDPSKAWGEV

KRQIYVAAFTVQAAAETLSEVA

>145 3rd FN3 domain of tenascin C
DAPSQIEVKDVTDTTALITWFKPLAEIDGIELTYGIKDVPGDRTTIDLTEDENQYSIGNLKPDTEYEVSLISRR

GDMSSNPAKETFTT

>146 Fibcon
LDAPTDLQVTNVTDTSITVSWTPPSATITGYRITYTPSNGPGEPKELTVPPSSTSVTITGLTPGVEYVVSLYAL

KDNQESPPLVGTQTT

>147 10$^{th}$ FN3 domain of fibronectin
VSDVPRDLEVVAATPTSLLISWDAPAVTVRYYRITYGETGGNSPVQEFTVPGSKSTATISGLKPGVDYTITV

YAVTGRGDSPASSKPISINYRT

-continued

>148
GSGS

>149
GGGSGGGS

>150
GGGGSGGGGSGGGGSGGGGSGGGGS

>151
APAP

>152
APAPAPAPAP

>153
APAPAPAPAPAPAPAPAPAP

>154
APAPAPAPAPAPAPAPAPAPAPAPAPAPAPAPAPAPAPAP

>155 Albumin variant
DAHKSEVAHRFKDLGEENFKALVLIAFAQYLQQSPFEDHVKLVNEV1EFAKTCVADESAENCDKSLHTLF

GDKLCTVATLRETYGEMADCCAKQEPERNECFLQHKDDNPNLPRLVRPEVDVMCTAFHDNEETF

LKKYLYEIARRHPYFYAPELLFFAKRYKAAFTECCQAADKAACLLPKLDELRDEGKASSAKQRLK

CASLQKFGERAFKAWAVARLSQRFPKAEFAEVSKLVTDLTKVHTECCHGDLLECADDRADLAKY

ICENQDSISSKLKECCEKPLLEKSHCIAEVENDEMPADLPSLAADFVESKDVCKNYAEAKDVFLGM

FLYEYARRHPDYSVVLLLRLAKTYETTLEKCCAAADPHECYAKVFDEFKPLVEEPQNLIKQNCELF

EQLGEYKFQNALLVRYTKKVPQVSTPTLVEVSRNLGKVGSKCCKHPEAKRMPCAEDYLSVVLNQ

LCVLHEKTPVSDRVTKCCTESLVNRRPCFSALEVDETYVPKEFNAETFTFHADICTLSEKERQIKKQ

TALVELVKHKPKATKEQLKAVMDDFAAFVEKCCKADDKETCFAEEGKKLVAASQAALGL

>156 cDNA H10
CTGCCAGCCCCGAAGAATTTGGTCGTTTCCCGTGTCACTGAGGACTCTGCACGTCTGAGCTGGACCGC

ACCGGACGCGGCGTTCGACAGCTTTGCAATCGGCTACTGGGAGTGGGATGATGACGGCGAGGCCATTG

TGCTGACCGTTCCGGGTAGCGAGCGCAGCTACGATCTGACCGGTCTGAAGCCGGGTACGGAATATCCG

GTGTATATTGCGGGCGTGAAGGGTGGCCAGTGGAGCTTCCCGCTGAGCGCGATCTTTACCACC

>157 cDNA P258AR6P1071_D02
CTGCCGGCTCCGAAAAACCTGGTCGTTTCCCGTGTCACTGAAGATTCTGCACGCTTGAGCTGGGCGATC

GACGAGCAGCGTGACTGGTTTGAGAGCTTCCTGATTCAGTATCAAGAATCGGAAAAAGTTGGCGAGGC

CATCGTGCTGACCGTTCCGGGTAGCGAGCGCAGCTATGATCTGACGGGTCTGAAGCCAGGCACCGAGT

ATACGGTGAGCATTTACGGTGTCTACCATGTGTACCGTAGCAATCCGCTGAGCGCGATCTTCACCACC

>158 cDNA
P233FR9P1001_H3-1
CTGCCAGCCCCGAAAAACTTAGTTGTCTCCCGCGTGACCGAAGATTCTGCTCGTCTGAGCTGGACTGC

ACCGGACGCGGCGTTCGACAGCTTTCCGATTGGCTACTGGGAGTGGGATGATGACGGTGAAGCGATCG

TGCTGACCGTTCCGGGTAGCGAGCGTAGCTATGACCTGACGGGTTTGAAACCTGGTACCGAGTATCAC

GTTTACATTGCGGGCGTCAAGGGTGGCCAGTGGTCGTTCCCGCTGAGCGCAATCTTTACGACC

>159 PSMA epitope
KKSPSPEFSGMPRISK

>160 PSMA epitope
NWETNKF

What is claimed:

1. An anti-human prostate specific membrane antigen (PSMA) binding polypeptide comprising the amino acid sequence of SEQ ID NO: 88 and optionally an additional methionine at the N-terminus.

2. The polypeptide of claim 1 conjugated to at least one second molecule.

3. The polypeptide of claim 2, wherein said at least one second molecule is a cytotoxic agent, a detectable label, polyethylene glycol, or a nucleic acid.

4. The polypeptide of claim 3, wherein the cytotoxic agent is auristatin, monomethyl auristatin phenylalanine, dolostatin, a chemotherapeutic agent, a drug, a growth inhibitory agent, a toxin, or a radioactive isotope.

5. The polypeptide of claim 3, wherein the detectable label is a radioactive isotope, a magnetic bead, a metallic bead, a colloidal particle, a fluorescent dye, an electron-dense reagent, an enzyme, biotin, digoxigenin, or a hapten.

6. The polypeptide of claim 2, wherein said at least one second molecule is a serum albumin polypeptide, an antibody that specifically binds to a serum albumin polypeptide, or an immunoglobulin Fc region.

7. A polynucleotide comprising a nucleotide sequence encoding the polypeptide of claim 1.

8. A vector comprising the polynucleotide of claim 7.

9. An isolated host cell comprising the vector of claim 8.

10. A method of producing a polypeptide comprising the amino acid sequence of SEQ ID NO: 88 and optionally an additional methionine at the N-terminus, said method comprising culturing the host cell of claim 9 under conditions such that the polypeptide is expressed and optionally purifying the polypeptide.

11. A composition comprising the polypeptide of claim 1 and a pharmaceutically acceptable carrier.

12. A diagnostic kit comprising the polypeptide of claim 1.

13. A diagnostic agent comprising the polypeptide of claim 1.

14. A method of detecting a human PSMA polypeptide comprising SEQ ID NO: 144 in a biological sample, said method comprising contacting a biological sample with an anti-human PSMA binding polypeptide according to claim 1 and detecting any resulting complexes comprising the human PSMA polypeptide and said anti-human PSMA binding polypeptide.

* * * * *